(12) United States Patent
Gangakhedkar et al.

(10) Patent No.: US 8,785,443 B2
(45) Date of Patent: Jul. 22, 2014

(54) METHODS OF USING PRODRUGS OF METHYL HYDROGEN FUMARATE AND PHARMACEUTICAL COMPOSITIONS THEREOF

(75) Inventors: Archana Gangakhedkar, San Jose, CA (US); Xuedong Dai, San Jose, CA (US); Noa Zerangue, Belmont, CA (US); Peter A. Virsik, Portola Valley, CA (US)

(73) Assignee: XenoPort, Inc., Santa Clara, CA (US)

( * ) Notice: Subject to any disclaimer, the term of this patent is extended or adjusted under 35 U.S.C. 154(b) by 5 days.

(21) Appl. No.: 13/274,284

(22) Filed: Oct. 14, 2011

(65) Prior Publication Data
US 2012/0095003 A1 Apr. 19, 2012

Related U.S. Application Data

(62) Division of application No. 12/544,133, filed on Aug. 19, 2009, now Pat. No. 8,148,414.

(60) Provisional application No. 61/090,163, filed on Aug. 19, 2008.

(51) Int. Cl.
| A61K 31/421 | (2006.01) |
| A61K 31/5375 | (2006.01) |
| A61K 31/225 | (2006.01) |
| A61K 31/4965 | (2006.01) |

(52) U.S. Cl.
USPC ........ 514/237.5; 514/547; 514/548; 514/363; 514/507; 514/478; 514/479; 514/255.01; 514/376; 514/423; 514/458; 514/263.36

(58) Field of Classification Search
USPC .......................... 514/547, 376, 237.5, 255.01
See application file for complete search history.

(56) References Cited

U.S. PATENT DOCUMENTS

| 3,336,364 A | 8/1967 | Dill |
| 4,851,439 A | 7/1989 | Speiser et al. |
| 4,959,389 A | 9/1990 | Speiser et al. |
| 5,073,641 A | 12/1991 | Bundgaard et al. |
| 5,149,695 A | 9/1992 | Speiser et al. |
| 5,424,332 A | 6/1995 | Speiser et al. |
| 5,451,667 A | 9/1995 | Speiser et al. |
| 5,534,250 A | 7/1996 | Klaveness et al. |
| 6,130,248 A | 10/2000 | Nudelman et al. |
| 6,277,882 B1 | 8/2001 | Joshi et al. |
| 6,355,676 B1 | 3/2002 | Joshi et al. |
| 6,359,003 B1 | 3/2002 | Joshi et al. |
| 6,436,992 B1 | 8/2002 | Joshi et al. |
| 6,509,376 B1 | 1/2003 | Joshi et al. |
| 6,858,750 B2 | 2/2005 | Joshi et al. |
| 7,157,423 B2 | 1/2007 | Joshi et al. |
| 7,320,999 B2 | 1/2008 | Joshi et al. |
| 7,432,240 B2 | 10/2008 | Joshi et al. |
| 7,612,110 B2 | 11/2009 | Joshi et al. |
| 7,619,001 B2 | 11/2009 | Joshi et al. |
| 7,638,118 B2 | 12/2009 | Flachsmann et al. |
| 7,790,916 B2 | 9/2010 | Joshi et al. |
| 7,803,840 B2 | 9/2010 | Joshi et al. |
| 7,915,310 B2 | 3/2011 | Joshi et al. |
| 8,148,414 B2 | 4/2012 | Gangakhedkar et al. |
| 2003/0018072 A1 | 1/2003 | Joshi et al. |
| 2004/0054001 A1 | 3/2004 | Joshi et al. |
| 2004/0102525 A1 | 5/2004 | Kozachuk |
| 2005/0096369 A1 | 5/2005 | Hoang |
| 2005/0148664 A1 | 7/2005 | Joshi et al. |
| 2006/0205659 A1 | 9/2006 | Joshi et al. |
| 2007/0027076 A1 | 2/2007 | Joshi et al. |
| 2007/0213300 A1 | 9/2007 | Liu et al. |
| 2007/0248663 A1 | 10/2007 | Joshi et al. |
| 2007/0253902 A1 | 11/2007 | Lobb et al. |
| 2008/0004344 A1 | 1/2008 | Nilsson et al. |
| 2008/0089861 A1 | 4/2008 | Went et al. |
| 2008/0227847 A1 | 9/2008 | Nilsson et al. |
| 2008/0233185 A1 | 9/2008 | Joshi et al. |
| 2008/0299196 A1 | 12/2008 | Nilsson et al. |
| 2008/0300217 A1 | 12/2008 | Nilsson |
| 2009/0011986 A1 | 1/2009 | Joshi et al. |
| 2009/0181085 A1 | 7/2009 | Joshi et al. |
| 2009/0182047 A1 | 7/2009 | Joshi et al. |
| 2009/0304790 A1 | 12/2009 | Nilsson et al. |
| 2010/0130607 A1 | 5/2010 | Gold |
| 2010/0144651 A1 | 6/2010 | Nilsson et al. |
| 2011/0112196 A1 | 5/2011 | Lukashev |
| 2011/0124615 A1 | 5/2011 | Joshi et al. |
| 2012/0034274 A1 | 2/2012 | Nilsson et al. |

FOREIGN PATENT DOCUMENTS

| CN | 101774913 A | 7/2010 |
| GB | 2 285 805 A | 7/1995 |
| PL | 153592 | 10/1991 |
| WO | WO 96/36613 A1 | 11/1996 |
| WO | WO 98/29114 | 7/1998 |

(Continued)

OTHER PUBLICATIONS

Schafer et al. Drug Discovery Today, 2008, 13 (21/22), 913-916.*
Horig et al. Journal of Translational Medicine 2004, 2(44), 1-8.*
Altmeyer et al., Antipsoriatic effect of fumaric acid derivatives, J. Amer. Acad. Derm. (1994), 30(6): 977-981.
Ashe, Learning and memory in transgenic mice modeling Alzheimer's disease. *Learning & Memory* (2001), 8, 301-308.
Atreya et al., NF-κB in inflammatory bowel disease. *J Intern Med* (2008), 263, 591-596.
Author Unknown, BG 00012, BG 12/oral fumarate, FAG-201, second-generation fumarate derivative—Fumapharm/Biogen Idec, *Drugs RD* (2005), 6(4): 229-230.
Bardgett et al., NMDA receptor blockade and hippocampal neuronal loss impair fear conditioning and position habit reversal in C57B1/6 mice. *Brain Res Bull* (2003), 60, 131-142.

(Continued)

*Primary Examiner* — Yong Chu
(74) *Attorney, Agent, or Firm* — Poisinelli PC

(57) ABSTRACT

Prodrugs of methyl hydrogen fumarate, pharmaceutical compositions comprising prodrugs of methyl hydrogen fumarate, and methods of using prodrugs of methyl hydrogen fumarate and pharmaceutical compositions thereof for treating diseases such as psoriasis, asthma, multiple sclerosis, inflammatory bowel disease, and arthritis are disclosed.

42 Claims, No Drawings

(56) References Cited

FOREIGN PATENT DOCUMENTS

| | | |
|---|---|---|
| WO | WO 98/29114 A1 | 7/1998 |
| WO | WO 98/52549 A2 | 11/1998 |
| WO | WO 99/49858 A1 | 10/1999 |
| WO | WO 99/51191 A1 | 10/1999 |
| WO | WO 99/62973 A1 | 12/1999 |
| WO | WO 00/10560 A1 | 3/2000 |
| WO | WO 00/12072 A2 | 3/2000 |
| WO | WO 02/055063 A2 | 7/2002 |
| WO | WO 02/055066 A1 | 7/2002 |
| WO | WO 02/055067 A3 | 7/2002 |
| WO | WO 03/087174 A2 | 10/2003 |
| WO | WO 2005/023241 A1 | 3/2005 |
| WO | WO 2005/027899 A1 | 3/2005 |
| WO | WO 2006/037342 A2 | 4/2006 |
| WO | WO 2006/050730 A1 | 5/2006 |
| WO | WO 2006/122652 A2 | 11/2006 |
| WO | WO 2007/006307 A2 | 1/2007 |
| WO | WO 2007/006308 A2 | 1/2007 |
| WO | WO 2007/042034 A1 | 4/2007 |
| WO | WO 2007/042035 A2 | 4/2007 |
| WO | WO 2008/096271 A2 | 8/2008 |
| WO | WO 2008/097596 A2 | 8/2008 |
| WO | WO 2010/079221 A1 | 7/2010 |
| WO | WO 2010/126605 A1 | 11/2010 |

OTHER PUBLICATIONS

Barnes, Mediators of chronic obstructive pulmonary disease. *Pharmacological Reviews* (2004), 56(4), 515-548.

Behari et al., Baseline characteristics of a subpopulation of Indian patients enrolled in two phase 3 trials for oral BG-12 in relapsing-remitting multiple sclerosis, $62^{nd}$ Ann Mtg. Amer. Acad. Neurol. (2010), poster, 2 pages.

Bhagavathula et al., 7-Chloro-5-(4-hydroxyphenyl)-1-methyl-3-(naphthalen-2-ylmethyl)-4,5-dihydro-1H-benzo[b][1,4]diazepin-2(3H)-one (Bz-423), a benzodiazepine, suppresses keratinocyte proliferation and has antipsoriatic activity in the human skin-severe, combined immunodeficient mouse transplant model. *J Pharmacol Expt'l Therapeutics* (2008), 324(3), 938-947.

Blandini, et al., Glutamate and Parkinson's disease. *Mol. Neurobiol.* (1996), 12(1), 73-94.

Brewer et al., Fumaric acid esters in the management of severe psoriasis, *Clin. Exper. Dermatol.* (2007), 32: 246-249.

Bundgaard et al., Esters of N,N-Disubstituted 2-Hydroxyacetamides as a Novel Highly Biolabile Prodrug Type for Carboxylic Acid Agents, *J. Med. Chem.* (1987), 30(3): 451-454.

Bundgaard et al., Glycolamide esters as a novel biolabile prodrug type for non-steroidal anti-inflammatory carboxylic acid drugs, *Int. J. Pharm.* (1988) 43: 101-110.

Cavarra et al., Effects of cigarette smoke in mice with different levels of $\alpha_1$-proteinase inhibitor and sensitivity to oxidants. *Am J Respir Crit Care Med* (2001), 164, 886-890.

Cockcroft et al., Bronchial reactivity to inhaled histamine: a method and clinical survey. *Clin Allergy* (1977), 7, 235-243.

D'Acquisto et al., Inhibition of nuclear factor kappa B (NF-κB): an emerging theme in anti-inflammatory therapies. *Molecular Interventions* (2002), 2(1), 22-35.

de Jong et al., Selective stimulation of T helper 2 cytokine responses by the anti-psoriasis agent monomethylfunarate, *Eur. J. Immunol.* (1996), 26: 2067-2074.

Ellrichmann et al., Efficacy of fumaric acid esters in the R6/2 and YAC128 models of Huntington's disease, *PLOS One* (2011), 6(1): 11 pages.

Eugster et al., Superantigen overcomes resistance of IL-6 deficient mice towards MOG-induced EAE by a TNFR1 controlled pathway. *Eur J Immunol* (2001), 31, 2302-2312.

European Commission Health & Consumer Protection Directorate-General, Report of the scientific committee on animal nutrition on the safety of fumaric acid, adopted Jan. 22, 2003: 18 pages.

Feinstein et al., Anti-inflammatory and prometabolic effects of BG-12 in glial cells, $26^{th}$ *Congress Eur. Cmtee. Treat. Res. Mult Soler.* (2010), poster: 1 page.

Fox et al., Baseline characteristics of patients in a randomized, multicenter, placebo-controlled and active comparator trial evaluating efficacy and safety of BG-12 in relapsing-remitting multiple sclerosis: the CONFIRM trial, $62^{nd}$ Ann Mtg. Amer. Acad. Neurol. (2010), poster, 2 pages.

Frycak et al., Evidence of covalent interaction of fumaric acid esters with sulfhydryl groups in peptides, *J. Mass. Spectrom.* (2005), 40: 1309-1318.

Gadad et al., Synthesis, spectral studies and anti-inflammatory activity of glycolamide esters of niflumic acid as potential prodrugs, *Arzneim Forsch Drug Res.* (2002), 52(11): 817-821.

Gesser et al., Dimethylfumarate specifically inhibits the mitogen and stress-activated kinases 1 and 2 (MSK1/2): Possible role for its antipsoriatic effect. *J Investigative Dermatology* (2007), 127, 2129-2137.

Goke et al., Effect of a Specific Serine Protease Inhibitor on the Rat Pancreas: Systemic Administration of Camostate and Exocrine Pancreatic Secretion, *Digestion* (1984) 30: 171-178.

Gold et al., Baseline characteristics of patients in the DEFINE trial: a randomized, multicenter, double blind, placebo-controlled, phase 3 study of BG-12 in relapsing-remitting multiple sclerosis, $62^{nd}$ Ann Mtg. Amer. Acad. Neurol. (2010), poster, 2 pages.

Grigorian et al., Control of T-cell mediated autoimmunity by metabolite flux to N-glycan biosynthesis, *J. Bio. Chem.* (2007), 282(27): 20027-20035.

Gurney et al., Motor neuron degeneration in mice that express a human Cu,Zn superoxide dismutase mutation. *Science* (1994), 264, 1772-1775.

Hanson et al., Nicotinic acid- and monomethyl funarate-induced flushing involves GPR109A expressed by keratinocytes and COX-2-dependent prostanoid formation in mice, *J. Clin. Invest.* (2010), 120(8): 2910-2919.

Hiraku et al., Absorption and Excretion of Camostat Orally Administered to Male Rabbit and Healthy Subject, *Iyakuhin Kenkyu* (1982) 13(3): 756-765.

Hoefnagel et al., Long-term safety aspects of systemic therapy with fumaric acid esters in severe psoriasis. *Br J Dermatology* (2003), 149, 363-369.

Hoxtermann et al., Fumaric acid esters suppress peripheral CD4- and CD8-positive lymphocytes in psoriasis, *Dermatology* (1998), 196: 223-230.

Invitation to Pay Additional Fees and Partial International Search, issued on Mar. 3, 2010, in PCT Application No. PCT/US2009/054349 (3 pages).

Iyer et al., Synthesis of iodoalkylacylates and their use in the preparation of S-alkyl phosphorothiolates. *Synth Commun* (1995), 25(18), 2739-2749.

Jennings, Squamous cell carcinoma as a complication of fumaric acid ester immunosuppression, *J. Eur. Acad. Dermatol. Venereol.* (2009), DOI: 10.1111/j.1468-3083.2009.03234.x, 1 page.

Jurjus et al., Animal models of inflammatory bowel disease. *J Pharmacol Toxicol Methods* (2004), 50, 81-92.

Kappos et al., Efficacy and safety of oral fumarate in patients relapsing-remitting multiple sclerosis: a multicentre, randomised, double-blind, placebo controlled phase IIb study, *Lancet* (2008), 372: 1463-1472.

Kamimura et al., "Stereoselective formation of optically active 2-oxy-1,3-oxazolidin-4-ones from chiral O-acylmandelamides or lactamides", *Tetrahedron* 58, 2002, 8763-8770.

Khan et al., Synthesis and biological evaluation of glycolamide esters as potential prodrugs of some non-steroidal anti-inflammatory drugs, *Ind. J. Chem.* (2002) 41 B: 2172-2175.

Lee et al., Spotlight on fumarates, *Int. MS J.* (2008), 15: 12-18.

Lehmann et al., Fumaric acid esters are potent immunosuppressants: inhibition of acute and chronic rejection in rat kidney transplantation models by methyl hydrogen fumarate. *Arch Dermatol Res* (2002), 294, 399-404.

Lehmann et al., Dimethylfumarate induces immunosuppression via glutathione depletion and subsequent induction of heme oxygenase 1. *J Investigative Dermatology* (2007), 127, 835-845.

(56) References Cited

OTHER PUBLICATIONS

Linker et al., Identification and development of new therapeutics for multiple sclerosis, *Treds. Pharm. Sci.* (2008), DOI 10.1016/j.tips.2008.07.012, 8 pages.

Linker et al., Fumaric acid esters exert neuroprotective effects in neuroinflammation via activation of the Nrf2 antioxidant pathway, *Brain* (2011), 134: 678-692.

Litjens e al., Monomethylfumarate affects polarization of monocyte-derived dendritic cells resulting in down-regulated Th1 lymphocyte responses, *Eur. J. Immunol.* (2004), 34: 565-575.

Litjens et al., Pharmacokinetics of oral fumarates in healthy subjects, *Br. J. Clin. Pharmacol.* (2004), 58(4): 429-432.

Litjens et al., Effects of monomethylfumarate on dendritic cell differentiation, *Br. J. Dermatol.* (2006), 154: 211-217.

Loewe et al., Dimethylfumarate inhibits TNF-induced nuclear entry of NF-κB/p65 in human endothelial cells. *J Immunology* (2002), 168, 4781-4787.

Loewe et al., Dimethylfumarate impairs melanoma growth in metastasis, *Cancer Res.* (2006), 66(24): 11888-11896.

Lopez-Diego et al., Novel therapeutic strategies for multiple sclerosis—a multifaceted adversary, *Nat. Review. Drug Disc.* (2008), 7:909-925.

Lukashev et al., Activation of Nrf2 and modulation of disease by BG00012 (dimethyl fumarate) suggest a dual cytoprotective and anti-inflammatory mechanism of action, $62^{nd}$ *Ann Mtg. Amer. Acad. Neurol.* (2010), poster, 4 pages.

Mandhane, et al., Adenosine $A_2$ receptors modulate haloperidol-induced catalepsy in rats. *Eur. J. Pharmacol* (1997), 328, 135-141.

Martin, Molecular basis of the neurodegenerative disorders. *N. Engl J Med* (1999), 340(25), 1970-1980.

Martorana et al., Roflumilast fully prevents emphysema in mice chronically exposed to cigarette smoke. *Am J Respir Crit Care Med* (2005), 172, 848-853.

Menter et al., Guidelines of care for the management of psoriasis and psoriatic arthritis, *J. Am. Acad. Dermatol.* (2009), doi:10.1016/j.jaad.2009.03.027, 35 pages.

Mosmann et al., TH1 and TH2 cells: different patterns of lymphokine secretion lead to different functional properties, *Ann. Rev. Immunol.* (1989), 7: 145-73.

Mrowietz et al., Treatment of psoriasis with fumaric acid esters: results of a prospective multicentre study, *Br. J. Dermatol.* (1998), 138: 456-460.

Mrowietz et al., Treatment of severe psoriasis with fumaric acid esters: scientific background and guidelines for therapeutic use. *Br J Dermatology* (1999), 141, 424-429.

Mrowietz et al., Dimethylfumarate for psoriasis: more than a dietary curiosity. *Trends Mol Med* (2005), 11(1), 43-48.

Mrowietz et al., Treatment of psoriasis with fumaric acid esters (Fumaderm®), JDDG (2007), DOI: 10.1111/j.1610-0387.2007.06346.x, 2 pages.

Murakami et al., Suppression of a dextran sodium sulfate-induced colitis in mice by zerumbone, a subtropical ginger sesquiterpene, and nimesulide: separately and in combination. *Biochemical Pharmacol* (2003), 66, 1253-1261.

Naldi et al., Psoriasis (chronic plaque), *Clin. Evid.* (2009), 1(1706): 50 pages.

Neymotin et al., Neuroprotective effect of Nrf2/AFE activators, CDDO ethylamide and CDDO trifluoroethylamide, in a mouse model of amyotrophic lateral sclerosis, *Free Rad. Bio. Med* (2011), 51: 88-96.

Nibbering et al., Intracellular signalling by binding sites for the antipsoriatic agent monomethylfumarate on human granulocytes, *Br. J. Dermatol.* (1997), 137: 65-75.

Nielsen et al., Glycolamide esters as biolabile prodrugs of carboxylic acid agents: synthesis, stability, bioconversion, and physicochemical properties. *J Pharmaceutical Sciences* (1988), 77(4), 285-298.

Offermans, The nicotinic acid receptor GPR109A (HM74A or Puma-G) as a new therapeutic agent, Trends Pharm. Sci. (2006), 27(7): 384-390.

Peeters et al., Fumaric acid therapy for psoriatic arthritis. A randomized, double-blind, placebo-controlled study, Br. J. Rheumatol. (1992), 31(7): 502-504.

Rantanen, The cause of the Chinese sofa/chair dermatitis epidemic is likely to be contact allergy to dimethylfumarate, a novel potent contact sensitizer, Br. J. Dermatol. (2008), 159: 218-221.

Reddingius, Bioanalysis and pharmacokinetics of fumarates in humans, Ph.D. dissertation Eth No. 12199, Swiss Fed. Inst. Tech. Zurich (1997), 82 pages.

Reich et al., Efficacy and safety of fumaric acid esters in the long-term treatment of psoriasis—a retrospective study (FUTURE), JDDG (2009), DOI: 10.1111/j.1610-0387.2009.07120.x, 8 pages.

Richman et al., Nicotinic acid receptor agonists differentially activate downstream effectors, J. Bio. Chem. (2007), 282(25): 18028-18036.

Roll et al., Use of fumaric acid esters in psoriasis, *Indian J. Dermatol. Ven. Lep.* (2007), 73: 133-137.

Rostami-Yazdi et al., Detection of metabolites of fumaric acid esters in human urine: implications for their mode of action, *J. Invest. Dermatol.* (2008), doi:10.1038/jid.2008.197, 3 pages.

Rostami-Yazdi et al., Pharmacokinetics of antipsoriatic fumaric acid esters in psoriasis patients, *Arch. Dermatol. Res.* (2010), 302: 531-538.

Rowland et al., Amyotrophic lateral sclerosis. *N. Engl J Med* (2001), 344(22), 1688-1700.

Rubant et al., Dimethylfumarate reduces leukocyte rolling in vivo through modulation of adhesion molecule expression, *J. Invest. Dermatol.* (2007), 128: 326-331.

Schilling et al., Fumaric acid esters are effective in chronic experimental autoimmune encephalomyelitis and suppress macrophage infiltration. *Clin Experimental Immunology* (2006), 145, 101-107.

Schimrigk et al., Oral fumaric acid esters for the treatment of active multiple sclerosis: an open-label, baseline-controlled pilot study. *Eur J Neurology* (2006), 13, 604-610.

Seder et al., Acquisition of lymphokine-producing phenotype by CD4+ T-cells, *Ann. Rev. Immunol.* (1994), 12: 635-73.

Sharma et al., Distal effect on mass spectral fragmentations of glycolamide esters of 6-methoxy-2-naphthylacetic acid (6-MNA) and the crystal structure of N,N'-dimethyl-glycolamide ester of 6-MNA, *Ind. J. Chem.* (2004) 43B: 1758-1764.

Soelberg Sorensen et al., Oral fumarate for relapsing-remitting multiple sclerosis, *Lancet* (2008), 372: 1447-1448.

Spencer et al., Induction of glutathione transferases and NAD(P)H: quinone reductase by fumaric acid derivatives in rodent cells and tissues, *Cancer Res.* (1990), 50: 7871-7875.

Stoof et al., The antipsoriatic drug dimethylfumarate strongly suppresses chemokine production in human keratinocytes and peripheral blood mononuclear cells, *Br. J. Dermatol.* (2001), 144: 1114-1120.

Tabruyn et al., NF-κB: a new player in angiostatic therapy. *Angiogenesis* (2008), 11, 101-106.

Talath et al., Stability studies of some glycolamide ester prodrugs of niflumic acid in aqueous buffers and human plasma by HPLC with UV detection, *Arz. Forsch Drug Res.* (2006), 56(9): 631-639.

Talath et al., Synthesis, stability studies, anti-inflammatory activity and ulcerogenicity of morpholinoalkyl ester prodrugs of niflumic acid, *Arz. Forsch Drug Res.* (2006), 56(11): 744-752.

Tang et al., The psoriasis drug monomethylfumarate is a potent nicotinic acid receptor agonist, *Biochem. Biophys. Res. Comm.* (2008), doi:10.1016/j.bbrc.2008.08.041, 4 pages.

Thomson et al., FK 506: a novel immunosuppressant for treatment of autoimmune disease: rationale and preliminary clinical experience at the University of Pittsburgh, *Springer Semin. Immunopathol.* (1993), 14(4): 323-344.

Tracey et al., Tumor necrosis factor antagonist mechanisms of action: a comprehensive review. *Pharmacology & Therapeutics* (2008), 117, 244-279.

Treumer et al., Dimethylfumarate is a potent inducer of apoptosis in human T cells. *J Invest Dermatol* (2003), 121, 1383-1388.

Van Schoor et al., Effect of inhaled fluticasone on bronchial responsiveness to neurokinin A in asthma. *Eur Respir J* (2002), 19, 997-1002.

Vandermeeren et al., Dimethylfumarate is an inhibitor of cytokine-induced E-selectin, VCAM-1, and ICAM-1 expression in human endothelial cells. *Biochem Biophys Res Commun* (1997), 234, 19-23.

(56) References Cited

OTHER PUBLICATIONS

Villegas et al., A new flavonoid derivative, dosmalfate, attenuates the development of dextran sulphate sodium-induced colitis in mice. *Int'l Immunopharmacol* (2003), 3, 1731-1741.
Virley, Developing therapeutics for the treatment of multiple sclerosis. *NeuroRx* (2005), 2, 638-649.
Wadhwa et al., Glycolamide esters of 6-methoxy-2-naphthylacetic acid as potential prodrugs—Synthetic and spectral studies, *Ind. J. Chem.* (1995), 34B: 408-415.
Wain et al., Treatment of severe, recalcitrant, chronic plaque psoriasis with fumaric acid esters: a prospective study, *Br. J. Dermatol.* (2009), DOI 10.1111/j.1365-2133.2009.09267.x, 8 pages.
Wakkee et al., Drug evaluation: BG-12, an immunomodulary dimethylfumarate, *Curr. Opin. Invest. Drug.* (2007), 8(11): 955-962.
Weber et al., Synthesis, In Vitro Skin Permeation Studies, and PLS-Analysis of New Naproxen Derivatives, *Pharm. Res.* (2001) 18(5): 600-607.
Weber et al., Treatment of disseminated granuloma annulare with low-dose fumaric acid, *Acta Derm. Venereol.* (2009), 89: 295-298.
Werdenberg et al., Presystemic metabolism and intestinal absorption of antipsoriatic fumaric acid esters, *Biopharm. Drug. Dispos.* (2003), 24: 259-273.
Wingerchuk et al., Multiple sclerosis: current pathophysiological concepts. *Lab Invest* (2001), 81(3), 263-281.
Woodworth et al., Oral BG-12 in combination with interferon beta or glatiramer acetate: pharmacokinetics, safety and tolerability, *26th Congress Eur. Cmtee. Treat. Res. Mult. Scler.* (2010), poster: 1 page.
Woodworth et al., Pharmacokinetics of oral BG-12 alone compared with BG-12 and interferon β-1a or glatiramer acetate administered together, studied in healthy volunteers, *62nd Ann Mtg. Amer. Acad. Neurol.* (2010), poster, 2 pages.
Wustrow et al., Comparison of the efficacy and tolerability of a novel methyl hydrogenfumarate prodrug with dimethylfumarate in rodent EAE and GI irritation models, XenoPort, Inc. (2010), poster: 1 page.
Xenoport, Inc., XenoPort announces presentation of preclinical data for novel fumarate analog XP23829 at ECTRIMS, Press Release dated Oct. 13, 2010, 3 pages.
Yang et al., Neuroprotective effects of the triterpenoid, CDDO methyl amide, a potent inducer of Nrf2-mediated transcription, *PLOS One* (2009), 4(6) doi:10.1371/journal.pone.0005757: 13 pages.
Yazdi et al., Fumaric acid esters. *Clinics Dermatology* (2008), 26, 522-526.
Zhu et al., Inhibition of dendritic cell differentiation by fumaric acid esters, *J. Invest. Dermatol.* (2001), 116: 203-208.
Gogas et al., Comparison of the efficacy and tolerability of a novel methyl hydrogen fumarate prodrug with dimethyl fumarate in rodent EAE and GI irritation models, XenoPort, Inc.; $26^{th}$ Congress of the European Committee for Treatment and Research in Multiple Sclerosis (ECTRIMS), 2010 (Poster #671) (1 page).
Horig et al., From bench to clinic and back: Perspective on the $1^{st}$ IQPC Translational Research conference, *J. Transl. Med.* (2004), 2(44), 8 pages.
Hurd et al., "Vinylation and the Formation of Acylals", J. Am. Chem. Soc. (1956), 78, p. 104-6.
Schafer et al., Failure is an option: learning from unsuccessful proof-of-concept trials, *Drug Discovery Today* (2008), 13(21/22), pp. 913-916.
Thing et al., "Prolonged Naproxen Joint Residence Time After Intra-Articular Injection of Lipophilic Solutions Comprising a Naproxen Glycolamide Ester Prodrug in the Rat", Int. J. Pharm. (2013), 451, pp. 34-40.
Wu et al., "Regulatory perspectives of Type II prodrug development and time-dependent toxicity management: Nonclinical Pharm/Tox analysis and the role of comparative toxicology," *Toxicology* (2007), 236, pp. 1-6.
Preliminary amendment filed Oct. 14, 2011, U.S. Appl. No. 13/274,282, 6 pages.
Non-final Office Action dated May 14, 2013, U.S. Appl. No. 13/274,282, 11 pages.
Response to Non-final Office Action filed Aug. 14, 2013, U.S. Appl. No. 13/274,282, 14 pages.
Invitation to Pay Additional Fees and Partial International Search Report dated Mar. 3, 2010, PCT Application No. PCT/US2009/054349, 3 pages.
Notice of Allowance dated Oct. 1, 2013, U.S. Appl. No. 13/274,282, 9 pages.

* cited by examiner

METHODS OF USING PRODRUGS OF METHYL HYDROGEN FUMARATE AND PHARMACEUTICAL COMPOSITIONS THEREOF

CROSS REFERENCE TO RELATED APPLICATIONS

This application is a divisional application of U.S. patent application Ser. No. 12/544,133 filed Aug. 19, 2009, now U.S. Pat. No. 8,148,414, which claims the benefit under 35 U.S.C. §119(e) of U.S. Provisional Application Ser. No. 61/090,163 filed Aug. 19, 2008, both of which are hereby incorporated by reference in their entirety.

SEQUENCE LISTING

A Sequence Listing submitted in computer readable form (CRF) is hereby incorporated by reference. The CRF file is named P190481 US04_ST25.txt, was created on Dec. 27, 2011, and contains 1 kilobyte.

FIELD

Disclosed herein are prodrugs of methyl hydrogen fumarate, pharmaceutical compositions comprising prodrugs of methyl hydrogen fumarate, and methods of using prodrugs of methyl hydrogen fumarate and pharmaceutical compositions thereof for treating diseases such as psoriasis, asthma, multiple sclerosis, inflammatory bowel disease, and arthritis.

BACKGROUND

Fumaric acid esters (FAEs) are approved in Germany for the treatment of psoriasis, are being evaluated in the United States for the treatment of psoriasis and multiple sclerosis, and have been proposed for use in treating a wide range of immunological, autoimmune, and inflammatory diseases and conditions.

FAEs and other fumaric acid derivatives have been proposed for use in treating a wide-variety of diseases and conditions involving immunological, autoimmune, and/or inflammatory processes including psoriasis (Joshi and Strebel, WO 1999/49858; U.S. Pat. No. 6,277,882; Mrowietz and Asadullah, *Trends Mol Med* 2005, 111(1), 43-48; and Yazdi and Mrowietz, *Clinics Dermatology* 2008, 26, 522-526); asthma and chronic obstructive pulmonary diseases (Joshi et al., WO 2005/023241 and US 2007/0027076); cardiac insufficiency including left ventricular insufficiency, myocardial infarction and angina pectoris (Joshi et al., WO 2005/023241; Joshi et al., US 2007/0027076); mitochondrial and neurodegenerative diseases such as Parkinson's disease, Alzheimer's disease, Huntington's disease, retinopathia pigmentosa and mitochondrial encephalomyopathy (Joshi and Strebel, WO 2002/055063, US 2006/0205659, U.S. Pat. No. 6,509,376, U.S. Pat. No. 6,858,750, and U.S. Pat. No. 7,157,423); transplantation (Joshi and Strebel, WO 2002/055063, US 2006/0205659, U.S. Pat. No. 6,359,003, U.S. Pat. No. 6,509,376, and U.S. Pat. No. 7,157,423; and Lehmann et al., *Arch Dermatol Res* 2002, 294, 399-404); autoimmune diseases (Joshi and Strebel, WO 2002/055063, U.S. Pat. No. 6,509,376, U.S. Pat. No. 7,157,423, and US 2006/0205659) including multiple sclerosis (MS) (Joshi and Strebel, WO 1998/52549 and U.S. Pat. No. 6,436,992; Went and Lieberburg, US 2008/0089896; Schimrigk et al., *Eur J Neurology* 2006, 13, 604-610; and Schilling et al., *Clin Experimental Immunology* 2006, 145, 101-107); ischemia and reperfusion injury (Joshi et al., US 2007/0027076); AGE-induced genome damage (Heidland, WO 2005/027899); inflammatory bowel diseases such as Crohn's disease and ulcerative colitis; arthritis; and others (Nilsson et al., WO 2006/037342 and Nilsson and Muller, WO 2007/042034).

The mechanism of action of fumaric acid esters is believed to be mediated by pathways associated with the immunological response. For example, FAEs invoke a shift from a Th1 to Th2 immune response, favorably altering the cytokine profile; inhibit cytokine-induced expression of adhesion molecules such as VCAM-1, ICAM-1 and E-selectin, thereby reducing immune cell extravasation; and deplete lymphocytes through apoptotic mechanisms (Lehmann et al., *J Investigative Dermatology* 2007, 127, 835-845; Gesser et al., *J Investigative Dermatology* 2007, 127, 2129-2137; Vandermeeren et al., *Biochm Biophys Res Commun* 1997, 234, 19-23; and Treumer et al., *J Invest Dermatol* 2003, 121, 1383-1388).

Recent studies suggest that FAEs are inhibitors of NF-κB activation, a transcription factor that regulates the inducible expression of proinflammatory mediators (D'Acquisto et al., *Molecular Interventions* 2002, 2(1), 22-35). Accordingly, FAEs have been proposed for use in treating NF-κB mediated diseases (Joshi et al., WO 2002/055066; and Joshi and Strebel, WO 2002/055063, US 2006/0205659, U.S. Pat. No. 7,157,423 and U.S. Pat. No. 6,509,376) Inhibitors of NF-κB activation have also been shown to be useful in angiostatic therapy (Tabruyn and Griffioen, Angiogenesis 2008, 11, 101-106), inflammatory bowel disease (Atreya et al., *J Intern Med* 2008, 263(6), 591-6); and in animal models of diseases involving inflammation including neutrophilic alveolitis, asthma, hepatitis, inflammatory bowel disease, neurodegeneration, ischemia/reperfusion, septic shock, glomerulonephritis, and rheumatoid arthritis (D'Acquisto et al., *Molecular Interventions* 2002, 2(1), 22-35).

Studies also suggest that NF-κB inhibition by FAEs may be mediated by interaction with tumor necrosis factor (TNF) signaling. Dimethyl fumarate inhibits TNF-induced tissue factor mRNA and protein expression and TNF-induced DNA binding of NF-κB proteins, and inhibits the TNF-induced nuclear entry of activated NF-κB proteins thereby inhibiting inflammatory gene activation (Loewe et al., *J Immunology* 2002, 168, 4781-4787). TNF signaling pathways are implicated in the pathogenesis of immune-mediated inflammatory diseases such as rheumatoid arthritis, Crohn's disease, psoriasis, psoriatic arthritis, juvenile idiopathic arthritis, and ankylosing spondylitis (Tracey et al., *Pharmacology & Therapetuics* 2008, 117, 244-279).

Fumaderm®, an enteric coated tablet containing a salt mixture of monoethyl fumarate and dimethylfumarate (DMF) (2) which is rapidly hydrolyzed to monomethyl fumarate (MHF) (1), regarded as the main bioactive metabolite, was approved in Germany in 1994 for the treatment of psoriasis.

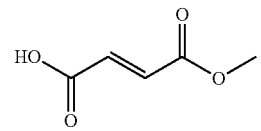

(1)

-continued

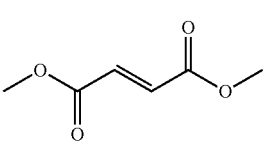
(2)

Fumaderm® is dosed TID with 1-2 grams/day administered for the treatment of psoriasis. Fumaderm® exhibits a high degree of interpatient variability with respect to drug absorption and food strongly reduces bioavailability. Absorption is thought to occur in the small intestine with peak levels achieved 5-6 hours after oral administration. Significant side effects occur in 70-90% of patients (Brewer and Rogers, *Clin Expt'l Dermatology* 2007, 32, 246-49; and Hoefnagel et al., *Br J Dermatology* 2003, 149, 363-369). Side effects of current FAE therapy include gastrointestinal upset including nausea, vomiting, and diarrhea; transient flushing of the skin. Also, DMF exhibits poor aqueous solubility.

Fumaric acid derivatives (Joshi and Strebel, WO 2002/055063, US 2006/0205659, and U.S. Pat. No. 7,157,423 (amide compounds and protein-fumarate conjugates); Joshi et al., WO 2002/055066 and Joshi and Strebel, U.S. Pat. No. 6,355,676 (mono and dialkyl esters); Joshi and Strebel, WO 2003/087174 (carbocyclic and oxacarbocyclic compounds); Joshi et al., WO 2006/122652 (thiosuccinates); Joshi et al., US 2008/0233185 (dialkyl and diaryl esters) and salts (Nilsson et al., US 2008/0004344) have been developed in an effort to overcome the deficiencies of current FAE therapy. Controlled release pharmaceutical compositions comprising fumaric acid esters are disclosed by Nilsson and Müller, WO 2007/042034. Glycolamide ester prodrugs are described by Nielsen and Bundgaard, *J Pharm Sci* 1988, 77(4), 285-298.

SUMMARY

MHF prodrugs having high gastrointestinal permeability and/or absorption, improved solubility, ordered hydrolysis (i.e., preferential cleavage of promoieties), and minimal cleavage in the gut lumen or enterocyte cytoplasm are desirable. Such MHF prodrugs that provide higher oral bioavailability and plasma levels of MHF, DMF, and/or other metabolites may enhance the efficacy/responder rate compared to present fumaric acid esters; facilitate the use of lower doses, reduced dosing frequency, and standardized dosing regimens; reduce food effects; reduce gastrointestinal side effects/toxicity; and reduce interpatient treatment variability.

In a first aspect, compounds of Formula (I) are provided:

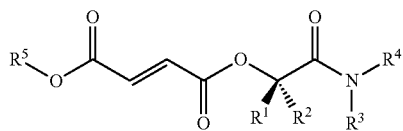
(I)

or a pharmaceutically acceptable salt thereof, wherein:

$R^1$ and $R^2$ are independently chosen from hydrogen, $C_{1-6}$ alkyl, and substituted $C_{1-6}$ alkyl;

$R^3$ and $R^4$ are independently chosen from hydrogen, $C_{1-6}$ alkyl, substituted $C_{1-6}$ alkyl, $C_{1-6}$ heteroalkyl, substituted $C_{1-6}$ heteroalkyl, $C_{4-12}$ cycloalkylalkyl, substituted $C_{4-12}$ cycloalkylalkyl, $C_{7-12}$ arylalkyl, and substituted $C_{7-12}$ arylalkyl; or $R^3$ and $R^4$ together with the nitrogen to which they are bonded form a ring chosen from a $C_{5-10}$ heteroaryl, substituted $C_{5-10}$ heteroaryl, $C_{5-10}$ heterocycloalkyl, and substituted $C_{5-10}$ heterocycloalkyl; and $R^5$ is chosen from methyl, ethyl, and $C_{3-6}$ alkyl;

wherein each substituent group is independently chosen from halogen, —OH, —CN, —CF$_3$, =O, —NO$_2$, benzyl, —C(O)NR$^{11}_2$, —R$^{11}$, —OR$^{11}$, —C(O)R$^{11}$, COOR$^{11}$, and —NR$^{11}_2$ wherein each R$^{11}$ is independently chosen from hydrogen and $C_{1-4}$ alkyl;

with the proviso that when $R^5$ is ethyl; then $R^3$ and $R^4$ are independently chosen from hydrogen, $C_{1-6}$ alkyl, and substituted $C_{1-6}$ alkyl.

In a second aspect, compounds of Formula (II) are provided:

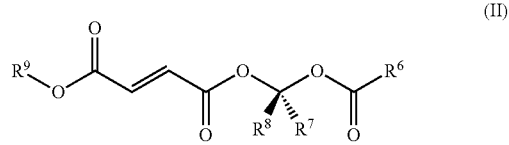
(II)

or a pharmaceutically acceptable salt thereof, wherein:

$R^6$ is chosen from $C_{1-6}$ alkyl, substituted $C_{1-6}$ alkyl, $C_{1-6}$ heteroalkyl, substituted $C_{1-6}$ heteroalkyl, $C_{3-8}$ cycloalkyl, substituted $C_{3-8}$ cycloalkyl, $C_{6-8}$ aryl, substituted $C_{6-8}$ aryl, and —OR$^{10}$ wherein R$^{10}$ is chosen from $C_{1-6}$ alkyl, substituted $C_{1-6}$ alkyl, $C_{3-10}$ cycloalkyl, substituted $C_{3-10}$ cycloalkyl, $C_{6-10}$ aryl, and substituted $C_{6-10}$ aryl;

$R^7$ and $R^8$ are independently chosen from hydrogen, $C_{1-6}$ alkyl, and substituted $C_{1-6}$ alkyl; and $R^9$ is chosen from $C_{1-6}$ alkyl and substituted $C_{1-6}$ alkyl;

wherein each substituent group is independently chosen from halogen, —OH, —CN, —CF$_3$, =O, —NO$_2$, benzyl, —C(O)NR$^{11}_2$, —R$^{11}$, —OR$^{11}$, —C(O)R$^{11}$, COOR$^{11}$, and —NR$^{11}_2$ wherein each R$^{11}$ is independently chosen from hydrogen and $C_{1-4}$ alkyl.

In a third aspect, compounds of Formula (III) are provided:

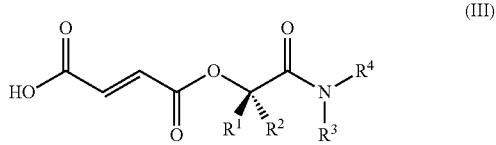
(III)

or a pharmaceutically acceptable salt thereof, wherein:

$R^1$ and $R^2$ are independently chosen from hydrogen, $C_{1-6}$ alkyl, and substituted $C_{1-6}$ alkyl; and $R^3$ and $R^4$ are independently chosen from hydrogen, $C_{1-6}$ alkyl, substituted $C_{1-6}$ alkyl, $C_{1-6}$ heteroalkyl, substituted $C_{1-6}$ heteroalkyl, $C_{4-12}$ cycloalkylalkyl, substituted $C_{4-12}$ cycloalkylalkyl, $C_{7-12}$ arylalkyl, and substituted $C_{7-12}$ arylalkyl; or $R^3$ and $R^4$ together with the nitrogen to which they are bonded form a ring chosen from a $C_{5-10}$ heteroaryl, substituted $C_{5-10}$ heteroaryl, $C_{5-10}$ heterocycloalkyl, and substituted $C_{5-10}$ heterocycloalkyl;

wherein each substituent group is independently chosen from halogen, —OH, —CN, —CF$_3$, =O, —NO$_2$, benzyl, —C(O)NR$^{11}_2$, —R$^{11}$, —OR$^{11}$, —C(O)R$^{11}$, —COOR$^{11}$, and —NR$^{11}_2$ wherein each R$^{11}$ is independently chosen from hydrogen and $C_{1-4}$ alkyl.

In a fourth aspect, compounds of Formula (IV) are provided:

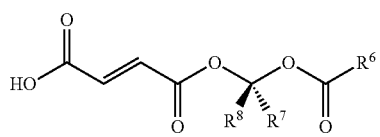

or a pharmaceutically acceptable salt thereof, wherein:

$R^6$ is chosen from $C_{1-6}$ alkyl, substituted $C_{1-6}$ alkyl, $C_{1-6}$ heteroalkyl, substituted $C_{1-6}$ heteroalkyl, $C_{3-8}$ cycloalkyl, substituted $C_{3-8}$ cycloalkyl, $C_{6-8}$ aryl, substituted $C_{6-8}$ aryl, and —$OR^{10}$, wherein $R^{10}$ is chosen from $C_{1-6}$ alkyl, substituted $C_{1-6}$ alkyl, $C_{3-10}$ cycloalkyl, substituted $C_{3-10}$ cycloalkyl, $C_{6-10}$ aryl, and substituted $C_{6-10}$ aryl; and $R^7$ and $R^8$ are independently chosen from hydrogen, $C_{1-6}$ alkyl, and substituted $C_{1-6}$ alkyl;

wherein each substituent group is independently chosen from halogen, —OH, —CN, —$CF_3$, =O, —$NO_2$, benzyl, —C(O)$NR^{11}_2$, —$R^{11}$, —$OR^{11}$, C(O)$R^{11}$, COO$R^{11}$, and —$NR^{11}_2$ wherein each $R^{11}$ is independently chosen from hydrogen and $C_{1-4}$ alkyl;

with the provisos that;
when one of $R^7$ and $R^8$ is chosen from ethyl and methyl, and the other of $R^7$ and $R^8$ is hydrogen; then $R^6$ is not —C(CH$_3$)=CH$_2$; and
when each of $R^7$ and $R^8$ is hydrogen; then $R^6$ is not chosen from —CH=CH$_2$ and 4-carboxyphenyl.

In a fifth aspect, pharmaceutical compositions are provided comprising a compound of Formulae (I)-(IV) and at least one pharmaceutically acceptable vehicle.

In a sixth aspect, methods of treating a disease in a patient are provided comprising administering to a patient in need of such treatment a pharmaceutical composition comprising a therapeutically effective amount of a compound of Formulae (I)-(IV). In certain embodiments, the disease is chosen from psoriasis, multiple sclerosis, an inflammatory bowel disease, asthma, chronic obstructive pulmonary disease, and arthritis.

In a seventh aspect, methods of inhibiting NF-κB activation in a patient are provided comprising administering to a patient a pharmaceutical composition comprising a therapeutically effective amount of a compound of Formulae (I)-(IV).

In an eighth aspect, methods of inhibiting TNF function in a patient are provided comprising administering to a patient a pharmaceutical composition comprising a therapeutically effective amount of a compound of Formulae (I)-(IV).

DETAILED DESCRIPTION

Definitions

A dash ("-") that is not between two letters or symbols is used to indicate a point of attachment for a moiety or substituent. For example, —CONH$_2$ is bonded through the carbon atom.

"Alkyl" refers to a saturated or unsaturated, branched, or straight-chain, monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having combinations of single, double, and triple carbon-carbon bonds. Where a specific level of saturation is intended, the terms alkanyl, alkenyl, and alkynyl are used. In certain embodiments, an alkyl group can have from 1 to 20 carbon atoms ($C_{1-20}$) in certain embodiments, from 1 to 10 carbon atoms ($C_{1-10}$), in certain embodiments from 1 to 8 carbon atoms ($C_{1-8}$), in certain embodiments, from 1 to 6 carbon atoms ($C_{1-6}$), in certain embodiments from 1 to 4 carbon atoms ($C_{1-4}$), and in certain embodiments, from 1 to 3 carbon atoms ($C_{1-3}$).

"Aryl" refers to a monovalent aromatic hydrocarbon radical derived by the removal of one hydrogen atom from a single carbon atom of a parent aromatic ring system. Aryl benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5- to 7-membered heterocycloalkyl ring containing one or more heteroatoms chosen from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can have from 6 to 20 carbon atoms ($C_{6-20}$), from 6 to 12 carbon atoms ($C_{6-12}$), from 6 to 10 carbon atoms ($C_{6-10}$), and in certain embodiments from 6 to 8 carbon atoms ($C_{6-8}$). Aryl, however, does not encompass or overlap in any way with heteroaryl, separately defined herein.

"Arylalkyl" refers to an acyclic alkyl radical in which one of the hydrogen atoms bonded to a carbon atom, typically a terminal or sp$^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl, or arylalkynyl is used. In certain embodiments, an arylalkyl group is $C_{7-30}$ arylalkyl, e.g., the alkanyl, alkenyl or alkynyl moiety of the arylalkyl group is $C_{1-10}$ and the aryl moiety is $C_{6-20}$, in certain embodiments, an arylalkyl group is $C_{6-18}$ arylalkyl, e.g., the alkanyl, alkenyl or alkynyl moiety of the arylalkyl group is $C_{1-8}$ and the aryl moiety is $C_{6-10}$. In certain embodiments, an arylalkyl group is $C_{7-12}$ arylalkyl.

"Compounds" of Formulae (I)-(IV) disclosed herein include any specific compounds within these formulae. Compounds may be identified either by their chemical structure and/or chemical name. Compounds are named using Chemistry 4-D Draw Pro, version 7.01c (ChemInnovation Software, Inc., San Diego, Calif.). When the chemical structure and chemical name conflict, the chemical structure is determinative of the identity of the compound. The compounds described herein may comprise one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan. Compounds of Formulae (I)-(IV) include, but are not limited to, optical isomers of compounds of Formulae (I)-(IV), racemates thereof, and other mixtures thereof. In such embodiments, a single enantiomer or diastereomer, i.e., optically active form can be obtained by asymmetric synthesis or by resolution of the racemates. Resolution of the racemates may be accomplished, for example, by conventional methods such as crystallization in the presence of a resolving agent, or chromatography using, for example, chiral stationary phases. Not withstanding the foregoing, in compounds of Formulae (I)-(IV) the configuration of the illustrated double bond is only in the E configuration (i.e. trans configuration).

Compounds of Formulae (I)-(IV) may also exist in several tautomeric forms including the enol form, the keto form, and mixtures thereof. Accordingly, the chemical structures depicted herein encompass all possible tautomeric forms of the illustrated compounds. Compounds of Formulae (I)-(IV) also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds may exist in unsolvated forms as well as solvated forms, including hydrated forms and as N-oxides. In general, compounds as referred to herein may be free acid, hydrated, solvated, or N-oxides. Certain compounds may exist in multiple crystalline, co-crystalline, or amorphous forms. Compounds of Formulae (I)-(IV) include pharmaceutically acceptable salts thereof, or pharmaceutically acceptable solvates of the free acid form of any of the foregoing, as well as crystalline forms of any of the foregoing.

Compounds of Formulae (I)-(IV) also include solvates. A solvate refers to a molecular complex of a compound with one or more solvent molecules in a stoichiometric or non-stoichiometric amount. Such solvent molecules are those commonly used in the pharmaceutical art, which are known to be innocuous to a patient, e.g., water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules is water.

Further, when partial structures of the compounds are illustrated, an asterisk (*) indicates the point of attachment of the partial structure to the rest of the molecule.

"Cycloalkyl" refers to a saturated or partially unsaturated cyclic alkyl radical. Where a specific level of saturation is intended, the nomenclature cycloalkanyl or cycloalkenyl is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, $C_{3-12}$ cycloalkyl, and in certain embodiments, $C_{3-8}$ cycloalkyl.

"Cycloalkylalkyl" refers to an acyclic alkyl radical in which one of the hydrogen atoms bonded to a carbon atom, typically a terminal or sp$^3$ carbon atom, is replaced with a cycloalkyl group. Where specific alkyl moieties are intended, the nomenclature cycloalkylalkanyl, cycloalkylalkenyl, or cycloalkylalkynyl is used. In certain embodiments, a cycloalkylalkyl group is $C_{4-30}$ cycloalkylalkyl, e.g., the alkanyl, alkenyl, or alkynyl moiety of the cycloalkylalkyl group is $C_{1-10}$ and the cycloalkyl moiety is $C_{3-20}$, and in certain embodiments, a cycloalkylalkyl group is $C_{3-20}$ cycloalkylalkyl, e.g., the alkanyl, alkenyl, or alkynyl moiety of the cycloalkylalkyl group is $C_{1-8}$ and the cycloalkyl moiety is $C_{3-12}$. In certain embodiments, a cycloalkylalkyl group is $C_{4-12}$ cycloalkylalkyl.

"Disease" refers to a disease, disorder, condition, or symptom of any of the foregoing.

"Drug" as defined under 21 U.S.C. §321(g)(1) means "(A) articles recognized in the official United States Pharmacopoeia, official Homeopathic Pharmacopoeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals . . . ."

"Halogen" refers to a fluoro, chloro, bromo, or iodo group. In certain embodiments, halogen refers to a chloro group.

"Heteroalkyl" by itself or as part of another substituent refer to an alkyl group in which one or more of the carbon atoms (and certain associated hydrogen atoms) are independently replaced with the same or different heteroatomic groups. Examples of heteroatomic groups include, but are not limited to, —O—, —S—, —O—O—, —S—S—, —O—S—, —NR$^{13}$, =N—N=, —N=N—, —N=N—NR$^{13}$—, —PR$^{13}$—, —P(O)$_2$—, —POR$^{13}$—, —O—P(O)$_2$—, —SO—, —SO$_2$—, —Sn(R$^{13}$)$_2$—, and the like, where each R$^{13}$ is independently chosen from hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{6-12}$ heteroaryl, substituted $C_{6-12}$ heteroaryl, $C_{7-18}$ heteroarylalkyl, or substituted $C_{7-18}$ heteroarylalkyl. Reference to, for example, a $C_{1-6}$ heteroalkyl, means a $C_{1-6}$ alkyl group in which at least one of the carbon atoms (and certain associated hydrogen atoms) is replaced with a heteroatom. For example $C_{1-6}$ heteroalkyl includes groups having five carbon atoms and one heteroatom, groups having four carbon atoms and two heteroatoms, etc. In certain embodiments, each R$^{13}$ is independently chosen from hydrogen and $C_{1-3}$ alkyl. In certain embodiments, a heteroatomic group is chosen from —O—, —S—, —NH—, —N(CH$_3$)—, and —SO$_2$—; and in certain embodiments, the heteroatomic group is —O—.

"Heteroaryl" refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which can be aromatic or non-aromatic. For example, heteroaryl encompasses bicyclic rings in which one ring is heteroaromatic and the second ring is a heterocycloalkyl ring. For such fused, bicyclic heteroaryl ring systems wherein only one of the rings contains one or more heteroatoms, the radical carbon may be at the aromatic ring or at the heterocycloalkyl ring. In certain embodiments, when the total number of N, S, and O atoms in the heteroaryl group exceeds one, the heteroatoms are not adjacent to one another. In certain embodiments, the total number of heteroatoms in the heteroaryl group is not more than two.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like. In certain embodiments, a heteroaryl group is from 4- to 20-membered heteroaryl ($C_{4-20}$), and in certain embodiments from 4- to 12-membered heteroaryl ($C_{4-10}$). In certain embodiments, heteroaryl groups are those derived from thiophene, pyrrole, benzothiophene, benzofuran, indole, pyridine, quinoline, imidazole, oxazole, or pyrazine. For example, in certain embodiments, $C_5$ heteroaryl can be furyl, thienyl, pyrrolyl, imidazolyl, pyrazolyl, isothiazolyl, isoxazolyl.

"Heterocycloalkyl" refers to a saturated or unsaturated cyclic alkyl radical in which one or more carbon atoms (and certain associated hydrogen atoms) are independently replaced with the same or different heteroatom; or to a parent aromatic ring system in which one or more carbon atoms (and certain associated hydrogen atoms) are independently replaced with the same or different heteroatom such that the ring system no longer contains at least one aromatic ring. Examples of heteroatoms to replace the carbon atom(s) include, but are not limited to, N, P, O, S, Si, etc. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like. In certain embodiments, a heterocycloalkyl group is $C_{5-10}$ heterocycloalkyl, $C_{5-8}$ heterocycloalkyl, and in certain embodiments, $C_{5-6}$ heterocycloalkyl.

"Leaving group" has the meaning conventionally associated with it in synthetic organic chemistry, i.e., an atom or a group capable of being displaced by a nucleophile and includes halogen such as chloro, bromo, fluoro, and iodo, acyloxy (alkoxycarbonyl) such as acetoxy and benzoyloxy, aryloxycarbonyl, mesyloxy, tosyloxy, trifluoromethanesulfonyloxy, aryloxy such as 2,4-dinitrophenoxy, methoxy, N,O-dimethylhydroxylamino, p-nitrophenolate, imidazolyl, and the like.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to an aromatic ring system in which one or more carbon atoms (and any associated hydrogen atoms) are independently replaced with the same or different heteroatom in such a way as to maintain the continuous π-electron system characteristic of aromatic systems and a number of out-of-plane π-electrons corresponding to the Hückel rule (4n+2). Examples of heteroatoms to replace the carbon atoms include, but are not limited to, N, P, O, S, and Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, a pharmaceutically acceptable salt is the hydrochloride salt. In certain embodiments, a pharmaceutically acceptable salt is the sodium salt.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound of Formulae (I)-(IV) and at least one pharmaceutically acceptable vehicle, with which the compound of Formulae (I)-(IV) is administered to a patient.

"Substituted" refers to a group in which one or more hydrogen atoms are independently replaced with the same or substituent group(s). In certain embodiments, each substituent group is independently chosen from halogen, —OH, —CN, —$CF_3$, =O, —$NO_2$, benzyl, —C(O)$NH_2$, —$R^{11}$, —$OR^{11}$, —C(O)$R^{11}$, —$COOR^{11}$, and —$NR^{11}_2$ wherein each $R^{11}$ is independently chosen from hydrogen and $C_{1-4}$ alkyl. In certain embodiments, each substituent group is independently chosen from halogen, —OH, —CN, —$CF_3$, —$NO_2$, benzyl, —$R^{11}$, —$OR^{11}$, and —$NR^{11}_2$ wherein each $R^{11}$ is independently chosen from hydrogen and $C_{1-4}$ alkyl. In certain embodiments, each substituent group is independently chosen from halogen, —OH, —CN, —$CF_3$, =O, —$NO_2$, benzyl, —C(O)$NR^{11}_2$, —$R^{11}$, —$OR^{11}$, —C(O)$R^{11}$, —$COOR^{11}$, and —$NR^{11}_2$ wherein each $R^{11}$ is independently chosen from hydrogen and $C_{1-4}$ alkyl. In certain embodiments, each substituent group is independently chosen from —OH, $C_{1-4}$ alkyl, and —$NH_2$.

"Treating" or "treatment" of any disease refers to reversing, alleviating, arresting, or ameliorating a disease or at least one of the clinical symptoms of a disease, reducing the risk of acquiring a disease or at least one of the clinical symptoms of a disease, inhibiting the progress of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter that may or may not be discernible to the patient. In certain embodiments, "treating" or "treatment" refers to delaying the onset of the disease or at least one or more symptoms thereof in a patient which may be exposed to or predisposed to a disease even though that patient does not yet experience or display symptoms of the disease.

"Therapeutically effective amount" refers to the amount of a compound that, when administered to a subject for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

Reference is now made in detail to certain embodiments of compounds, compositions, and methods. The disclosed embodiments are not intended to be limiting of the claims. To the contrary, the claims are intended to cover all alternatives, modifications, and equivalents.

Compounds

Certain embodiments provide a compound of Formula (I):

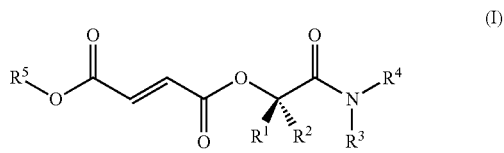

(I)

or a pharmaceutically acceptable salt thereof, wherein:
$R^1$ and $R^2$ are independently chosen from hydrogen, $C_{1-6}$ alkyl, and substituted $C_{1-6}$ alkyl;
$R^3$ and $R^4$ are independently chosen from hydrogen, $C_{1-6}$ alkyl, substituted $C_{1-6}$ alkyl, $C_{1-6}$ heteroalkyl, substituted $C_{1-6}$ heteroalkyl, $C_{4-12}$ cycloalkylalkyl, substituted $C_{4-12}$ cycloalkylalkyl, $C_{7-12}$ arylalkyl, and substituted $C_{7-12}$ arylalkyl; or $R^3$ and $R^4$ together with the nitrogen to which they are bonded form a ring chosen from a $C_{5-10}$ heteroaryl, substituted $C_{5-10}$ heteroaryl, $C_{5-10}$ heterocycloalkyl, and substituted $C_{5-10}$ heterocycloalkyl; and
$R^5$ is chosen from methyl, ethyl, and $C_{3-6}$ alkyl;
wherein each substituent group is independently chosen from halogen, —OH, —CN, —$CF_3$, =O, —$NO_2$, benzyl, —C(O)$NR^{11}_2$, —$R^{11}$, —$OR^{11}$, —C(O)$R^{11}$, —$COOR^{11}$, and —$NR^{11}_2$ wherein each $R^{11}$ is independently chosen from hydrogen and $C_{1-4}$ alkyl;
with the proviso that when $R^5$ is ethyl, then $R^3$ and $R^4$ are chosen from hydrogen, $C_{1-6}$ alkyl, and substituted $C_{1-6}$ alkyl.

In certain embodiments of a compound of Formula (I), each substituent group is independently chosen from halogen, —OH, —CN, —$CF_3$, —$R^{11}$, —$OR^{11}$, and —$NR^{11}_2$ wherein each $R^{11}$ is independently chosen from hydrogen and $C_{1-4}$ alkyl. In certain embodiments, each substituent group is independently chosen from —OH, and —COOH.

In certain embodiments of a compound of Formula (I), each substituent group is independently chosen from =O, $C_{1-4}$ alkyl, and —$COOR^{11}$ wherein $R^{11}$ is chosen from hydrogen and $C_{1-4}$ alkyl.

In certain embodiments of a compound of Formula (I), each of $R^1$ and $R^2$ is hydrogen.

In certain embodiments of a compound of Formula (I), one of $R^1$ and $R^2$ is hydrogen and the other of $R^1$ and $R^2$ is $C_{1-4}$ alkyl.

In certain embodiments of a compound of Formula (I), one of $R^1$ and $R^2$ is hydrogen and the other of $R^1$ and $R^2$ is chosen from methyl, ethyl, n-propyl, isopropyl, n-butyl, isobutyl, sec-butyl, and tert-butyl.

In certain embodiments of a compound of Formula (I), one of $R^1$ and $R^2$ is hydrogen and the other of $R^1$ and $R^2$ is methyl.

In certain embodiments of a compound of Formula (I), $R^3$ and $R^4$ are independently chosen from hydrogen and $C_{1-6}$ alkyl.

In certain embodiments of a compound of Formula (I), $R^3$ and $R^4$ are independently chosen from hydrogen and $C_{1-4}$ alkyl.

In certain embodiments of a compound of Formula (I), $R^3$ and $R^4$ are independently chosen from hydrogen, methyl, and ethyl.

In certain embodiments of a compound of Formula (I), each of $R^3$ and $R^4$ is hydrogen; in certain embodiments, each of $R^3$ and $R^4$ is methyl; and in certain embodiments, each of $R^3$ and $R^4$ is ethyl.

In certain embodiments of a compound of Formula (I), $R^3$ is hydrogen; and $R^4$ is chosen from $C_{1-4}$ alkyl, substituted $C_{1-4}$ alkyl wherein the substituent group is chosen from =O, $-OR^{11}$, $-COOR^{11}$, and $-NR^{11}_2$, wherein each $R^{11}$ is independently chosen form hydrogen and $C_{1-4}$ alkyl.

In certain embodiments of a compound of Formula (I), $R^3$ is hydrogen; and $R^4$ is chosen from $C_{1-4}$ alkyl, benzyl, 2-methoxyethyl, carboxymethyl, carboxypropyl, 1,2,4-thiadoxolyl, methoxy, 2-methoxycarbonyl, 2-oxo(1,3-oxazolidinyl), 2-(methylethoxy)ethyl, 2-ethoxyethyl, (tert-butyloxycarbonyl)methyl, (ethoxycarbonyl)methyl, carboxymethyl, (methylethyl)oxycarbonylmethyl, and ethoxycarbonylmethyl.

In certain embodiments of a compound of Formula (I), $R^3$ and $R^4$ together with the nitrogen to which they are bonded form a ring chosen from a $C_{5-6}$ heterocycloalkyl, substituted $C_{5-6}$ heterocycloalkyl, $C_{5-6}$ heteroaryl, and substituted $C_{5-6}$ heteroaryl ring. In certain embodiments of a compound of Formula (I), $R^3$ and $R^4$ together with the nitrogen to which they are bonded form a ring chosen from a $C_5$ heterocycloalkyl, substituted $C_5$ heterocycloalkyl, $C_5$ heteroaryl, and substituted $C_5$ heteroaryl ring. In certain embodiments of a compound of Formula (I), $R^3$ and $R^4$ together with the nitrogen to which they are bonded form a ring chosen from a $C_6$ heterocycloalkyl, substituted $C_6$ heterocycloalkyl, $C_6$ heteroaryl, and substituted $C_6$ heteroaryl ring. In certain embodiments of a compound of Formula (I), $R^3$ and $R^4$ together with the nitrogen to which they are bonded form a ring chosen from piperazine, 1,3-oxazolidinyl, pyrrolidine, and morpholine ring In certain embodiments of a compound of Formula (I), $R^3$ and $R^4$ together with the nitrogen to which they are bonded form a $C_{5-10}$ heterocycloalkyl ring.

In certain embodiments of a compound of Formula (I), $R^5$ is methyl.

In certain embodiments of a compound of Formula (I), $R^5$ is ethyl.

In certain embodiments of a compound of Formula (I), $R^5$ is $C_{3-6}$ alkyl.

In certain embodiments of a compound of Formula (I), $R^5$ is chosen from methyl, n-propyl, isopropyl, n-butyl, sec-butyl, isobutyl, and tert-butyl.

In certain embodiments of a compound of Formula (I), $R^5$ is chosen from methyl, ethyl, n-propyl, isopropyl, n-butyl, sec-butyl, isobutyl, and tert-butyl.

In certain embodiments of a compound of Formula (I), one of $R^1$ and $R^2$ is hydrogen and the other of $R^1$ and $R^2$ is $C_{1-6}$ alkyl; $R^3$ is hydrogen; $R^4$ is chosen from hydrogen, $C_{1-6}$ alkyl, and benzyl.

In certain embodiments of a compound of Formula (I), one of $R^1$ and $R^2$ is hydrogen and the other of $R^1$ and $R^2$ is $C_{1-6}$ alkyl; $R^3$ is hydrogen; $R^4$ is chosen from hydrogen, $C_{1-6}$ alkyl, and benzyl; and $R^5$ is methyl.

In certain embodiments of a compound of Formula (I), one of $R^1$ and $R^2$ is hydrogen and the other of $R^1$ and $R^2$ is chosen from hydrogen and $C_{1-6}$ alkyl; and each of $R^3$ and $R^4$ is $C_{1-6}$ alkyl.

In certain embodiments of a compound of Formula (I), one of $R^1$ and $R^2$ is hydrogen and the other of $R^1$ and $R^2$ is chosen from hydrogen and $C_{1-6}$ alkyl; each of $R^3$ and $R^4$ is $C_{1-6}$ alkyl; and $R^5$ is methyl. In certain embodiments of a compound of Formula (I), each of $R^1$ and $R^2$ is hydrogen; each of $R^3$ and $R^4$ is $C_{1-6}$ alkyl; and $R^5$ is methyl.

In certain embodiments of a compound of Formula (I), one of $R^1$ and $R^2$ is hydrogen and the other of $R^1$ and $R^2$ is chosen from hydrogen and $C_{1-4}$ alkyl; $R^3$ is hydrogen; $R^4$ is chosen from $C_{1-4}$ alkyl, substituted $C_{1-4}$ alkyl wherein the substituent group is chosen from =O, $-OR^{11}$, $-COOR^{11}$, and $-NR^{11}_2$, wherein each $R^{11}$ is independently chosen form hydrogen and $C_{1-4}$ alkyl; and $R^5$ is methyl. In certain embodiments of a compound of Formula (I), one of $R^1$ and $R^2$ is hydrogen and the other of $R^1$ and $R^2$ is methyl; $R^3$ is hydrogen; $R^4$ is chosen from $C_{1-4}$ alkyl, substituted $C_{1-4}$ alkyl wherein the substituent group is chosen from =O, $-OR^{11}$, $-COOR^{11}$, and $-NR^{11}_2$, wherein each $R^{11}$ is independently chosen form hydrogen and $C_{1-4}$ alkyl; and $R^5$ is methyl. In certain embodiments of a compound of Formula (I), each of $R^1$ and $R^2$ is hydrogen; $R^3$ is hydrogen; $R^4$ is chosen from $C_{1-4}$ alkyl, substituted $C_{1-4}$ alkyl wherein the substituent group is chosen from =O, $-OR^{11}$, $-COOR^{11}$, and $-NR^{11}_2$, wherein each $R^{11}$ is independently chosen form hydrogen and $C_{1-4}$ alkyl; and $R^5$ is methyl.

In certain embodiments of a compound of Formula (I), $R^3$ and $R^4$ together with the nitrogen to which they are bonded form a $C_{5-10}$ heterocycloalkyl ring.

In certain embodiments of a compound of Formula (I), one of $R^1$ and $R^2$ is hydrogen and the other of $R^1$ and $R^2$ is chosen from hydrogen and $C_{1-6}$ alkyl; $R^3$ and $R^4$ together with the nitrogen to which they are bonded form a ring chosen from a $C_{5-6}$ heterocycloalkyl, substituted $C_{5-6}$ heterocycloalkyl, $C_{5-6}$ heteroaryl, and substituted $C_{5-6}$ heteroaryl ring; and $R^5$ is methyl. In certain embodiments of a compound of Formula (I), one of $R^1$ and $R^2$ is hydrogen and the other of $R^1$ and $R^2$ is methyl; $R^3$ and $R^4$ together with the nitrogen to which they are bonded form a ring chosen from a $C_{5-6}$ heterocycloalkyl, substituted $C_{5-6}$ heterocycloalkyl, $C_{5-6}$ heteroaryl, and substituted $C_{5-6}$ heteroaryl ring; and $R^5$ is methyl. In certain embodiments of a compound of Formula (I), each of $R^1$ and $R^2$ is hydrogen; $R^3$ and $R^4$ together with the nitrogen to which they are bonded form a ring chosen from a $C_{5-6}$ heterocycloalkyl, substituted $C_{5-6}$ heterocycloalkyl, $C_{5-6}$ heteroaryl, and substituted $C_{5-6}$ heteroaryl ring; and $R^5$ is methyl.

In certain embodiments of a compound of Formula (I), one of $R^1$ and $R^2$ is hydrogen and the other of $R^1$ and $R^2$ is chosen from hydrogen and $C_{1-6}$ alkyl; and $R^3$ and $R^4$ together with the nitrogen to which they are bonded form a ring chosen from morpholine, piperazine, and N-substituted piperazine.

In certain embodiments of a compound of Formula (I), one of $R^1$ and $R^2$ is hydrogen and the other of $R^1$ and $R^2$ is chosen from hydrogen and $C_{1-6}$ alkyl; $R^3$ and $R^4$ together with the nitrogen to which they are bonded form a ring chosen from morpholine, piperazine, and N-substituted piperazine; and $R^5$ is methyl.

In certain embodiments of a compound of Formula (I), $R^5$ is not methyl.

In certain embodiments of a compound of Formula (I), $R^1$ is hydrogen, and in certain embodiments, $R^2$ is hydrogen.

In certain embodiments of a compound of Formula (I), the compound is chosen from:

(N,N-diethylcarbamoyl)methyl methyl (2E)but-2-ene-1,4-dioate;

methyl [N-benzylcarbamoyl]methyl (2E)but-2-ene-1,4-dioate;

methyl 2-morpholin-4-yl-2-oxoethyl (2E)but-2-ene-1,4-dioate;

(N-butylcarbamoyl)methyl methyl (2E)but-2-ene-1,4-dioate;

[N-(2-methoxyethyl)carbamoyl]methyl methyl (2E)but-2-ene-1,4-dioate;

2-{2-[(2E)-3-(methoxycarbonyl)prop-2-enoyloxy]acetylamino}acetic acid;

4-{2-[(2E)-3-(methoxycarbonyl)prop-2-enoyloxy]acetylamino}butanoic acid;

methyl(N-(1,3,4-thiadiazol-2-yl)carbamoyl)methyl(2E)but-2ene-1,4-dioate;
(N,N-dimethylcarbamoyl)methyl methyl (2E)but-2-ene-1,4-dioate;
(N-methoxy-N-methylcarbamoyl)methyl methyl (2E)but-2-ene-1,4-dioate; bis-(2-methoxyethylamino)carbamoyl] methyl methyl (2E)but-2-ene-1,4-dioate;
[N-(methoxycarbonyl)carbamoyl]methyl methyl (2E)but-2ene-1,4-dioate;
4-{2-[(2E)-3-(methoxycarbonyl)prop-2-enoyloxy] acetylamino}butanoic acid, sodium salt;
methyl 2-oxo-2-piperazinylethyl (2E)but-2-ene-1,4-dioate;
methyl 2-oxo-2-(2-oxo(1,3-oxazolidin-3-yl)ethyl (2E)but-2ene-1,4-dioate;
{N-[2-(dimethylamino)ethyl]carbamoyl}methyl methyl (2E)but-2ene-1,4 dioate;
methyl 2-(4-methylpiperazinyl)-2-oxoethyl (2E)but-2-ene-1,4-dioate;
methyl {N-[(propylamino)carbonyl]carbamoyl}methyl (2E) but-2ene-1,4-dioate;
2-(4-acetylpiperazinyl)-2-oxoethyl methyl (2E)but-2ene-1,4-dioate;
{N,N-bis[2-(methylethoxy)ethyl]carbamoyl}methyl methyl (2E)but-2-ene-1,4-dioate;
methyl 2-(4-benzylpiperazinyl)-2-oxoethyl (2E)but-2-ene-1,4-dioate;
[N,N-bis(2-ethoxyethyl)carbamoyl]methyl methyl (2E)but-2-ene-1,4-dioate;
2-{(2S)-2-[(tert-butyl)oxycarbonyl]pyrrolidinyl}-2-oxoethyl methyl (2E)but-2ene-1,4-dioate;
1-{2-[(2E)-3-(methoxycarbonyl)prop-2-enoyloxy]acetyl}(2S)pyrrolidine-2-carboxylic acid;
(N-{[tert-butyl)oxycarbonyl]methyl}-N-methylcarbamoyl) methyl methyl (2E)but-2ene-1,4-dioate;
{N-(ethoxycarbonyl)methyl]-N-methylcarbamoyl}methyl methyl (2E)but-2-ene-1,4-dioate;
methyl 1-methyl-2-morpholin-4-yl-2-oxoethyl (2E)but-2-ene-1,4-dioate;
[N,N-bis(2-methoxyethyl)carbamoyl]ethyl methyl (2E)but-2-ene-1,4-dioate;
(N,N-dimethylcarbamoyl)ethyl methyl (2E)but-2-ene-1,4-dioate;
2-{2-[(2E)-3-(methoxy carbonyl)prop-2-enoyloxyl]-N-methylacetylamino}acetic acid;
(N-{[(tert-butyl)oxycarbonyl]methyl}carbamoyl)methyl methyl (2E)but-2-ene-1,4-dioate;
methyl (N-methyl-N-{[(methylethyl)oxycarbonyl] methyl}carbamoyl)methyl (2E)but-2-ene-1,4-dioate;
{N-[(ethoxycarbonyl)methyl]-N-benzylcarbamoyl}methyl methyl (2E)but-2-ene-1,4-dioate;
{N-[(ethoxycarbonyl)methyl]-N-benzylcarbamoyl}ethyl methyl (2E)but-2-ene-1,4-dioate;
{N-[(ethoxycarbonyl)methyl]-N-methylcarbamoyl}ethyl methyl (2E)but-2-ene-1,4-dioate;
(1S)-1-methyl-2-morpholin-4-yl-2-oxoethyl methyl (2E) but-2-ene-1,4-dioate;
(1S)-1-[N,N-bis(2-methoxyethyl)carbamoyl]ethyl methyl (2E)but-2-ene-1,4-dioate;
(1R)-1-(N,N-diethylcarbamoyl)ethyl methyl (2E)but-2-ene-1,4-dioate; and
a pharmaceutically acceptable salt of any of the foregoing.
In certain embodiments of a compound of Formula (I), the compound is chosen from:
(N,N-diethylcarbamoyl)methyl methyl (2E)but-2-ene-1,4-dioate;
methyl [N-benzylcarbamoyl]methyl (2E)but-2-ene-1,4-dioate;
methyl 2-morpholin-4-yl-2-oxoethyl (2E)but-2-ene-1,4-dioate;
(N-butylcarbamoyl)methyl methyl (2E)but-2-ene-1,4-dioate;
[N-(2-methoxyethyl)carbamoyl]methyl methyl (2E)but-2-ene-1,4-dioate;
2-{2-[(2E)-3-(methoxycarbonyl)prop-2-enoyloxy] acetylamino}acetic acid;
{2-[(2E)-3-(methoxycarbonyl)prop-2-enoyloxy] acetylamino}butanoic acid;
methyl(N-(1,3,4-thiadiazol-2-yl)carbamoyl)methyl(2E)but-2ene-1,4-dioate;
(N,N-dimethylcarbamoyl)methyl methyl (2E)but-2-ene-1,4-dioate;
(N-methoxy-N-methylcarbamoyl)methyl methyl (2E)but-2-ene-1,4-dioate;
bis-(2-methoxyethylamino)carbamoyl]methyl methyl (2E)but-2-ene-1,4-dioate;
[N-(methoxycarbonyl)carbamoyl]methyl methyl (2E)but-2ene-1,4-dioate;
methyl 2-oxo-2-piperazinylethyl (2E)but-2-ene-1,4-dioate;
methyl 2-oxo-2-(2-oxo(1,3-oxazolidin-3-yl)ethyl (2E)but-2ene-1,4-dioate;
{N-[2-(dimethylamino)ethyl]carbamoyl}methyl methyl (2E)but-2ene-1,4 dioate;
(N-[(methoxycarbonyl)ethyl]carbamoyl)methyl methyl (2E) but-2-ene-1,4-dioate;
2-{2-[(2E)-3-(methoxycarbonyl)prop-2-enoyloxy] acetylamino}propanoic acid; and
a pharmaceutically acceptable salt of any of the foregoing.

In certain embodiments of a compound of Formula (I), $R^3$ and $R^4$ are independently chosen from hydrogen, $C_{1-6}$ alkyl, substituted $C_{1-6}$ alkyl, $C_{6-10}$ aryl, substituted $C_{6-10}$ aryl, $C_{4-12}$ cycloalkylalkyl, substituted $C_{4-12}$ cycloalkylalkyl, $C_{7-12}$ arylalkyl, substituted $C_{7-12}$ arylalkyl, $C_{1-6}$ heteroalkyl, substituted $C_{1-6}$ heteroalkyl, $C_{6-10}$ heteroaryl, substituted $C_{6-10}$ heteroaryl, $C_{4-12}$ heterocycloalkylalkyl, substituted $C_{4-12}$ heterocycloalkylalkyl, $C_{7-12}$ heteroarylalkyl, substituted $C_{7-12}$ heteroarylalkyl; or $R^3$ and $R^4$ together with the nitrogen to which they are bonded form a ring chosen from a $C_{5-10}$ heteroaryl, substituted $C_{5-10}$ heteroaryl, $C_{5-10}$ heterocycloalkyl, and substituted $C_{5-10}$ heterocycloalkyl.

Certain embodiments provide a compound of Formula (II):

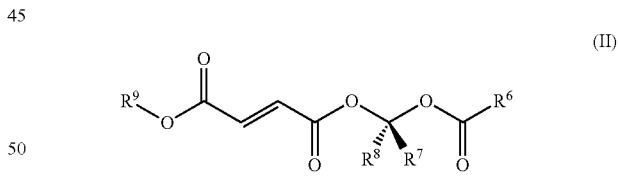

(II)

or a pharmaceutically acceptable salt thereof, wherein:
$R^6$ is chosen from $C_{1-6}$ alkyl, substituted $C_{1-6}$ alkyl, $C_{1-6}$ heteroalkyl, substituted $C_{1-6}$ heteroalkyl, $C_{3-8}$ cycloalkyl, substituted $C_{3-8}$ cycloalkyl, $C_{6-8}$ aryl, substituted $C_{6-8}$ aryl, and —$OR^{10}$ wherein $R^{10}$ is chosen from $C_{1-6}$ alkyl, substituted $C_{1-6}$ alkyl, $C_{3-10}$ cycloalkyl, substituted $C_{3-10}$ cycloalkyl, $C_{6-10}$ aryl, and substituted $C_{6-10}$ aryl;
$R^7$ and $R^8$ are independently chosen from hydrogen, $C_{1-6}$ alkyl, and substituted $C_{1-6}$ alkyl; and
$R^9$ is chosen from $C_{1-6}$ alkyl and substituted $C_{1-6}$ alkyl;
wherein each substituent group is independently chosen from halogen, —OH, —CN, —$CF_3$, =O, —$NO_2$, benzyl, —$C(O)NR^{11}_2$, —$R^{11}$, —$OR^{11}$, —$C(O)R^{11}$, $COOR^{11}$, and —$NR^{11}_2$ wherein each $R^{11}$ is independently chosen from hydrogen and $C_{1-4}$ alkyl.

In certain embodiments of a compound of Formula (II), each substituent group is independently chosen from halogen, —OH, —CN, —CF$_3$, —R$^{11}$, —OR$^{11}$, and —NR$^{11}{}_2$ wherein each R$^{11}$ is independently chosen from hydrogen and C$_{1-4}$ alkyl.

In certain embodiments of a compound of Formula (I), each substituent group is independently chosen from =O, C$_{1-4}$ alkyl, and —COOR$^{11}$ wherein R$^{11}$ is chosen from hydrogen and C$_{1-4}$ alkyl.

In certain embodiments of a compound of Formula (II), one of R$^7$ and R$^8$ is hydrogen and the other of R$^7$ and R$^8$ is C$_{1-6}$ alkyl. In certain embodiments of a compound of Formula (II), one of R$^7$ and R$^8$ is hydrogen and the other of R$^7$ and R$^8$ is C$_{1-4}$ alkyl.

In certain embodiments of a compound of Formula (II), one of R$^7$ and R$^8$ is hydrogen and the other of R$^7$ and R$^8$ is chosen from methyl, ethyl, n-propyl, and isopropyl. In certain embodiments of a compound of Formula (II), each of R$^7$ and R$^8$ is hydrogen.

In certain embodiments of a compound of Formula (II), R$^9$ is chosen from substituted C$_{1-6}$ alkyl and —OR$^{11}$ wherein R$^{11}$ is independently C$_{1-4}$ alkyl.

In certain embodiments of a compound of Formula (II), R$^9$ is C$_{1-6}$ alkyl, in certain embodiments, R$^9$ is C$_{1-3}$ alkyl; and in certain embodiments, R$^9$ is chosen from methyl and ethyl.

In certain embodiments of a compound of Formula (II), R$^9$ is methyl.

In certain embodiments of a compound of Formula (II), R$^9$ is chosen from ethyl, n-propyl, isopropyl, n-butyl, sec-butyl, isobutyl, and tert-butyl.

In certain embodiments of a compound of Formula (II), R$^9$ is chosen from methyl, ethyl, n-propyl, isopropyl, n-butyl, isobutyl, and tert-butyl.

In certain embodiments of a compound of Formula (II), R$^6$ is C$_{1-6}$ alkyl; one of R$^7$ and R$^8$ is hydrogen and the other of R$^7$ and R$^8$ is C$_{1-6}$ alkyl; and R$^9$ is chosen from C$_{1-6}$ alkyl and substituted C$_{1-6}$ alkyl.

In certain embodiments of a compound of Formula (II), R$^6$ is —OR$^{10}$.

In certain embodiments of a compound of Formula (II), R$^{10}$ is chosen from C$_{1-4}$ alkyl, cyclohexyl, and phenyl.

In certain embodiments of a compound of Formula (II), R$^6$ is chosen from methyl, ethyl, n-propyl, and isopropyl; one of R$^7$ and R$^8$ is hydrogen and the other of R$^7$ and R$^8$ is chosen from methyl, ethyl, n-propyl, and isopropyl.

In certain embodiments of a compound of Formula (II), R$^6$ is substituted C$_{1-2}$ alkyl, wherein each of the one or more substituent groups are chosen from —COOH, —NHC(O)CH$_2$NH$_2$, and —NH$_2$.

In certain embodiments of a compound of Formula (II), R$^6$ is chosen from ethoxy, methylethoxy, isopropyl, phenyl, cyclohexyl, cyclohexylloxy, —CH(NH$_2$)CH$_2$COOH, —CH$_2$CH(NH$_2$)COOH, —CH(NHC(O)CH$_2$NH$_2$)—CH$_2$COOH, and —CH$_2$CH(NHC(O)CH$_2$NH$_2$)—COOH.

In certain embodiments of a compound of Formula (II), R$^9$ is chosen from methyl and ethyl; one of R$^7$ and R$^8$ is hydrogen and the other of R$^7$ and R$^8$ is chosen from hydrogen, methyl, ethyl, n-propyl, and isopropyl; and R$^6$ is chosen from C$_{1-3}$ alkyl, substituted C$_{1-2}$ alkyl wherein each of the one or more substituent groups are chosen —COOH, —NHC(O)CH$_2$NH$_2$, and —NH$_2$, —OR$^{10}$ wherein R$^{10}$ is chosen from C$_{1-3}$ alkyl and cyclohexyl, phenyl, and cyclohexyl.

In certain embodiments of a compound of Formula (II), the compound is chosen from:
ethoxycarbonyloxyethyl methyl (2E)but-2-ene-1,4-dioate;
methyl (methylethoxycarbonyloxy)ethyl (2E)but-2-ene-1,4-dioate;
(cyclohexyloxycarbonyloxy)ethyl methyl (2E)but-2-ene-1,4-dioate; and
a pharmaceutically acceptable salt of any of the foregoing.

In certain embodiments of a compound of Formula (II), the compound is chosen from:
methyl (2-methylpropanoyloxy)ethyl (2E)but-2-ene-1,4-dioate;
methyl phenylcarbonyloxyethyl (2E)but-2-ene-1,4-dioate;
cyclohexylcarbonyloxybutyl methyl (2E)but-2-ene-1,4-dioate;
[(2E)-3-(methoxycarbonyl)prop-2-enoyloxy]ethyl methyl (2E)but-2-ene-1,4-dioate;
methyl 2-methyl-1-phenylcarbonyloxypropyl (2E)but-2-ene-1,4-dioate; and
a pharmaceutically acceptable salt of any of the foregoing.

In certain embodiments of a compound of Formula (II), the compound is chosen from:
ethoxycarbonyloxyethyl methyl (2E)but-2-ene-1,4-dioate;
methyl (methylethoxycarbonyloxy)ethyl (2E)but-2-ene-1,4-dioate;
methyl (2-methylpropanoyloxy)ethyl (2E)but-2-ene-1,4-dioate;
methyl phenylcarbonyloxyethyl (2E)but-2-ene-1,4-dioate;
cyclohexylcarbonyloxybutyl methyl (2E)but-2-ene-1,4-dioate;
[(2E)-3-(methoxycarbonyl)prop-2-enoyloxy]ethyl methyl (2E)but-2-ene-1,4-dioate;
(cyclohexyloxycarbonyloxy)ethyl methyl (2E)but-2-ene-1,4-dioate;
methyl 2-methyl-1-phenylcarbonyloxypropyl (2E)but-2-ene-1,4-dioate;
3-({[(2E)-3-(methoxycarbonyl)prop-2-enoyloxy]methyl}oxycarbonyl)(3S)-3-aminopropanoic acid, 2,2,2-trifluoroacetic acid;
3-({[(2E)-3-(methoxycarbonyl)prop-2-enoyloxy]methyl}oxycarbonyl)(2S)-2-aminopropanoic acid, 2,2,2-trifluoroacetic acid;
3-({[(2E)-3-(methoxycarbonyl)prop-2-enoyloxy]methyl}oxycarbonyl)(3S)-3-(2-aminoacetylamino)propanoic acid, 2,2,2-trifluoroacetic acid;
3-({[(2E)-3-(methoxycarbonyl)prop-2-enoyloxy]methyl}oxycarbonyl)(2S)-2-aminopropanoic acid, 2,2,2-trifluoroacetic acid;
3-{[(2E)-3-(methoxycarbonyl)prop-2enoyloxy]ethoxycarbonyloxy}(2S)-2-aminopropanoic acid, chloride; and
a pharmaceutically acceptable salt of any of the foregoing.

Compounds provided by the present disclosure include compounds of Formula (III) and Formula (IV). Compounds of Formula (III) and Formula (IV) may be produced by in vivo metabolism of compounds of Formula (I) and Formula (II), respectively; or may be administered to a patient.

Accordingly, certain embodiments provide a compound of Formula (III):

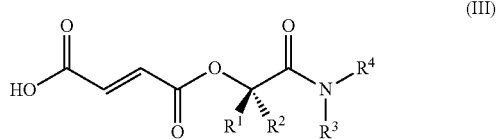

or a pharmaceutically acceptable salt thereof, wherein:
R$^1$ and R$^2$ are independently chosen from hydrogen, C$_{1-6}$ alkyl, and substituted C$_{1-6}$ alkyl; and
R$^3$ and R$^4$ are independently chosen from hydrogen, C$_{1-6}$ alkyl, substituted C$_{1-6}$ alkyl, C$_{1-6}$ heteroalkyl, substituted C$_{1-6}$ heteroalkyl, $C_{4-12}$ cycloalkylalkyl, substituted $C_{4-12}$ cycloalkylalkyl, $C_{7-12}$ arylalkyl, and substituted $C_{7-12}$ arylalkyl; or $R^3$ and $R^4$ together with the nitrogen to which they are bonded form a ring chosen from a $C_{5-10}$ heteroaryl, substituted $C_{5-10}$ heteroaryl, $C_{5-10}$ heterocycloalkyl, and substituted $C_{5-10}$ heterocycloalkyl;

wherein each substituent group is independently chosen from halogen, —OH, —CN, —CF$_3$, =O, —NO$_2$, benzyl, —C(O)NR$^{11}{}_2$, —R$^{11}$, —OR$^{11}$, —C(O)R$^{11}$, COOR$^{11}$, and —NR$^{11}{}_2$ wherein each R$^{11}$ is independently chosen from hydrogen and $C_{1-4}$ alkyl.

In certain embodiments of a compound of Formula (III), each substituent group is independently chosen from halogen, —OH, —CN, —CF$_3$, —R$^{11}$, —OR$^{11}$, and —NR$^{11}{}_2$ wherein each R$^{11}$ is independently chosen from hydrogen and $C_{1-4}$ alkyl.

In certain embodiments of a compound of Formula (III), each substituent group is independently chosen from =O, $C_{1-4}$ alkyl, and —COOR$^{11}$ wherein R$^{11}$ is chosen from hydrogen and $C_{1-4}$ alkyl.

In certain embodiments of a compound of Formula (III), each of R$^1$ and R$^2$ is hydrogen.

In certain embodiments of a compound of Formula (III), one of R$^1$ and R$^2$ is hydrogen and the other of R$^1$ and R$^2$ is $C_{1-4}$ alkyl.

In certain embodiments of a compound of Formula (III), one of R$^1$ and R$^2$ is hydrogen and the other of R$^1$ and R$^2$ is chosen from methyl, ethyl, n-propyl, isopropyl, n-butyl, isobutyl, sec-butyl, and tert-butyl.

In certain embodiments of a compound of Formula (III), one of R$^1$ and R$^2$ is hydrogen and the other of R$^1$ and R$^2$ is methyl.

In certain embodiments of a compound of Formula (III), R$^3$ and R$^4$ are independently chosen from hydrogen and $C_{1-6}$ alkyl.

In certain embodiments of a compound of Formula (III), R$^3$ and R$^4$ are independently chosen from hydrogen and $C_{1-4}$ alkyl.

In certain embodiments of a compound of Formula (III), R$^3$ and R$^4$ are independently chosen from hydrogen, methyl, and ethyl.

In certain embodiments of a compound of Formula (III), each of R$^3$ and R$^4$ is hydrogen; in certain embodiments, each of R$^3$ and R$^4$ is methyl; and in certain embodiments, each of R$^3$ and R$^4$ is ethyl.

In certain embodiments of a compound of Formula (III), R$^3$ is hydrogen; and R$^4$ is chosen from $C_{1-4}$ alkyl, substituted $C_{1-4}$ alkyl wherein the substituent group is chosen from =O, —OR$^{11}$, —COOR$^{11}$, and —NR$^{11}{}_2$, wherein each R$^{11}$ is independently chosen form hydrogen and $C_{1-4}$ alkyl.

In certain embodiments of a compound of Formula (III), R$^3$ is hydrogen; and R$^4$ is chosen from $C_{1-4}$ alkyl, benzyl, 2-methoxyethyl, carboxymethyl, carboxypropyl, 1,2,4-thiadoxolyl, methoxy, 2-methoxycarbonyl, 2-oxo(1,3-oxazolidinyl), 2-(methylethoxy)ethyl, 2-ethoxyethyl, (tert-butyloxycarbonyl)methyl, (ethoxycarbonyl)methyl, carboxymethyl, (methylethyl)oxycarbonylmethyl, and ethoxycarbonylmethyl.

In certain embodiments of a compound of Formula (III), R$^3$ and R$^4$ together with the nitrogen to which they are bonded form a ring chosen from a $C_{5-6}$ heterocycloalkyl, substituted $C_{5-6}$ heterocycloalkyl, $C_{5-6}$ heteroaryl, and substituted $C_{5-6}$ heteroaryl ring. In certain embodiments of a compound of Formula (III), R$^3$ and R$^4$ together with the nitrogen to which they are bonded form a ring chosen from a $C_5$ heterocycloalkyl, substituted $C_5$ heterocycloalkyl, $C_5$ heteroaryl, and substituted $C_5$ heteroaryl ring. In certain embodiments of a compound of Formula (III), R$^3$ and R$^4$ together with the nitrogen to which they are bonded form a ring chosen from a $C_6$ heterocycloalkyl, substituted $C_6$ heterocycloalkyl, $C_6$ heteroaryl, and substituted $C_6$ heteroaryl ring. In certain embodiments of a compound of Formula (III), R$^3$ and R$^4$ together with the nitrogen to which they are bonded form a ring chosen from piperazine, 1,3-oxazolidinyl, pyrrolidine, and morpholine ring In certain embodiments of a compound of Formula (III), R$^3$ and R$^4$ together with the nitrogen to which they are bonded form a $C_{5-10}$ heterocycloalkyl ring.

In certain embodiments of a compound of Formula (III), one of R$^1$ and R$^2$ is hydrogen and the other of R$^1$ and R$^2$ is $C_{1-6}$ alkyl; R$^3$ is hydrogen; R$^4$ is chosen from hydrogen, $C_{1-6}$ alkyl, and benzyl.

In certain embodiments of a compound of Formula (III), one of R$^1$ and R$^2$ is hydrogen and the other of R$^1$ and R$^2$ is chosen from hydrogen and $C_{1-6}$ alkyl; and each of R$^3$ and R$^4$ is $C_{1-6}$ alkyl. In certain embodiments of a compound of Formula (III), each of R$^1$ and R$^2$ is hydrogen; and each of R$^3$ and R$^4$ is $C_{1-6}$ alkyl. In certain embodiments of a compound of Formula (III), one of R$^1$ and R$^2$ is hydrogen and the other of R$^1$ and R$^2$ is chosen from hydrogen and $C_{1-4}$ alkyl; R$^3$ is hydrogen; and R$^4$ is chosen from $C_{1-4}$ alkyl, substituted $C_{1-4}$ alkyl wherein the substituent group is chosen from =O, —OR$^{11}$, —COOR$^{11}$, and —NR$^{11}{}_2$, wherein each R$^{11}$ is independently chosen form hydrogen and $C_{1-4}$ alkyl. In certain embodiments of a compound of Formula (III), one of R$^1$ and R$^2$ is hydrogen and the other of R$^1$ and R$^2$ is methyl; R$^3$ is hydrogen; and R$^4$ is chosen from $C_{1-4}$ alkyl, substituted $C_{1-4}$ alkyl wherein the substituent group is chosen from =O, —OR$^{11}$, —COOR$^{11}$, and —NR$^{11}{}_2$, wherein each R$^{11}$ is independently chosen form hydrogen and $C_{1-4}$ alkyl. In certain embodiments of a compound of Formula (III), each of R$^1$ and R$^2$ is hydrogen; R$^3$ is hydrogen; and R$^4$ is chosen from $C_{1-4}$ alkyl, substituted $C_{1-4}$ alkyl wherein the substituent group is chosen from =O, —OR$^{11}$, —COOR$^{11}$, and —NR$^{11}{}_2$, wherein each R$^{11}$ is independently chosen form hydrogen and $C_{1-4}$ alkyl.

In certain embodiments of a compound of Formula (III), R$^3$ and R$^4$ together with the nitrogen to which they are bonded form a $C_{5-10}$ heterocycloalkyl ring.

In certain embodiments of a compound of Formula (III), one of R$^1$ and R$^2$ is hydrogen and the other of R$^1$ and R$^2$ is chosen from hydrogen and $C_{1-6}$ alkyl; and R$^3$ and R$^4$ together with the nitrogen to which they are bonded form a ring chosen from a $C_{5-6}$ heterocycloalkyl, substituted $C_{5-6}$ heterocycloalkyl, $C_{5-6}$ heteroaryl, and substituted $C_{5-6}$ heteroaryl ring. In certain embodiments of a compound of Formula (III), one of R$^1$ and R$^2$ is hydrogen and the other of R$^1$ and R$^2$ is methyl; and R$^3$ and R$^4$ together with the nitrogen to which they are bonded form a ring chosen from a $C_{5-6}$ heterocycloalkyl, substituted $C_{5-6}$ heterocycloalkyl, $C_{5-6}$ heteroaryl, and substituted $C_{5-6}$ heteroaryl ring. In certain embodiments of a compound of Formula (III), each of R$^1$ and R$^2$ is hydrogen; and R$^3$ and R$^4$ together with the nitrogen to which they are bonded form a ring chosen from a $C_{5-6}$ heterocycloalkyl, substituted $C_{5-6}$ heterocycloalkyl, $C_{5-6}$ heteroaryl, and substituted $C_{5-6}$ heteroaryl ring.

In certain embodiments of a compound of Formula (III), one of R$^1$ and R$^2$ is hydrogen and the other of R$^1$ and R$^2$ is chosen from hydrogen and $C_{1-6}$ alkyl; and R$^3$ and R$^4$ together with the nitrogen to which they are bonded form a ring chosen from morpholine, piperazine, and N-substituted piperazine.

In certain embodiments of a compound of Formula (III), R$^3$ and R$^4$ are independently chosen from hydrogen, $C_{1-6}$ alkyl, substituted $C_{1-6}$ alkyl, $C_{6-10}$ aryl, substituted $C_{6-10}$ aryl, $C_{4-12}$ cycloalkylalkyl, substituted $C_{4-12}$ cycloalkylalkyl, $C_{7-12}$ arylalkyl, substituted $C_{7-12}$ arylalkyl, $C_{1-6}$ heteroalkyl, substituted $C_{1-6}$ heteroalkyl, $C_{6-10}$ heteroaryl, substituted $C_{6-10}$ heteroaryl, $C_{4-12}$ heterocycloalkylalkyl, substituted $C_{4-12}$ heterocycloalkylalkyl, $C_{7-12}$ heteroarylalkyl, substituted $C_{7-12}$ heteroarylalkyl; or $R^3$ and $R^4$ together with the nitrogen to which they are bonded form a ring chosen from a $C_{5-10}$ heteroaryl, substituted $C_{5-10}$ heteroaryl, $C_{5-10}$ heterocycloalkyl, and substituted $C_{5-10}$ heterocycloalkyl.

In certain embodiments of a compound of Formula (III), $R^1$ is hydrogen, and in certain embodiments, $R^2$ is hydrogen.

In certain embodiments of a compound of Formula (III), the compound is chosen from:
(2E)-3-[(2-morpholin-4-yl-2-oxoethyl)oxycarbonyl]prop-2-enoic acid;
(2E)-3-{[(N,N-diethylcarbamoyl)methyl]oxycarbonyl}prop-2-enoic acid;
(2E)-3-({[N-benzylcarbamoyl]methyl}oxycarbonyl)prop-2-enoic acid;
(2E)-3-[(2-morpholin-4-yl-2-oxoethyl)oxycarbonyl]prop-2-enoic acid;
(2E)-3-{[(N-butylcarbamoyl)methyl]oxycarbonyl}prop-2-enoic acid;
(2E)-3-{[N-methoxy-N-methylcarbamoyl)methyl]oxycarbonyl}prop-2-enoic acid;
bis-(2-methoxyethylamino)carbamoyl]methyl prop-2-enoic acid;
N,N-dimethylcarbamoyl)methyl pro-2-enoic acid;
(2E)-3-({[N-(3-carboxypropyl)carbamoyl]methyl}oxycarbonyl)prop-2-enoic acid;
methyl (N-(1,3,4-thiadiazol-2-yl)carbamoyl)methyl prop-2-enoic acid;
(2E)-3-[(2-{(2S)-2-[tert-butyl)oxycarbonyl]pyrrolidinyl}-2-oxoethyl) oxycarbonyl]prop-2enoic acid;
1-[2-((2E)-3-carboxyprop-2-enoyloxy)acetyl](2S) pyrrolidine-2-carboxylic acid;
(2E)-3-[({N-[(ethoxycarbonyl)methyl]-N-methylcarbamoyl}methyl)oxycarbonyl]prop-2-enoic acid;
(2E)-3-{[N-{[(tert-butyl)oxycarbonyl]methyl}-N-methylcarbamoyl]methyl]oxycarbonyl}prop-2-enoic acid;
(2E)-3-[(1-methyl-2-morpholin-4-yl-2-oxoethyl)oxycarbonyl]prop-2-enoic acid;
(2E)-3-({[N,N-bis(2-methoxyethyl)carbamoyl]ethyl}oxycarbonyl)prop-2-enoic acid;
(2E)-3-{[(N,N-dimethylcarbamoyl)ethyl]oxycarbonyl}prop-2-enoic acid;
(2E)-3-[({N,N-bis[2-methylethoxy)ethyl]carbamoyl}methyl)oxycarbonyl]prop-2-enoic acid;
(2E)-3-({[N,N-bis(2-ethoxyethyl)carbamoyl]methyl}oxycarbonyl)prop-2-enoic acid;
(2E)-3-{[2-(4-acetylpiperazinyl)-2-oxoethyl]oxycarbonyl}prop-2-enoic acid;
(2E)-3-({2-oxo-2-[4-benzylpiperazinyl]ethyl}oxycarbonyl)prop-2-enoic acid;
(2E)-3-{[(N-{[(tert-butyl)oxycarbonyl]methyl}carbamoyl)methyl]oxycarbonyl}prop-2-enoic acid;
(2E)-3-{[(N-methyl-N-{[(methylethyl)oxycarbonyl]methyl}carbamoyl)methyl]oxycarbonyl}prop-2-enoic acid;
(2E)-3-[({N-[(ethoxycarbonyl)methyl]-N-benzylcarbamoyl}methyl)oxycarbonyl]prop-2-enoic acid;
(2E)-3-[({N-[(ethoxycarbonyl)methyl]-N-benzylcarbamoyl}ethyl)oxycarbonyl]prop-2-enoic acid;

(2E)-3-[({N-[(ethoxycarbonyl)methyl]-N-methylcarbamoyl}ethyl)oxycarbonyl]prop-2-enoic acid; and
a pharmaceutically acceptable salt of any of the foregoing.

Certain embodiments provide a compound of Formula (IV):

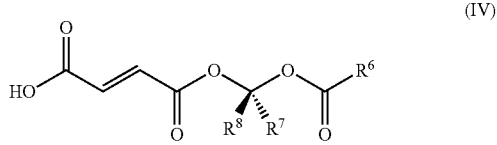

or a pharmaceutically acceptable salt thereof, wherein:
$R^6$ is chosen from $C_{1-6}$ alkyl, substituted $C_{1-6}$ alkyl, $C_{1-6}$ heteroalkyl, substituted $C_{1-6}$ heteroalkyl, $C_{3-8}$ cycloalkyl, substituted $C_{3-8}$ cycloalkyl, $C_{6-8}$ aryl, substituted $C_{6-8}$ aryl, and —$OR^{10}$, wherein $R^{10}$ is chosen from $C_{1-6}$ alkyl, substituted $C_{1-6}$ alkyl, $C_{3-10}$ cycloalkyl, substituted $C_{3-10}$ cycloalkyl, $C_{6-10}$ aryl, and substituted $C_{6-10}$ aryl; and
$R^7$ and $R^8$ are independently chosen from hydrogen, $C_{1-6}$ alkyl, and substituted $C_{1-6}$ alkyl;
wherein each substituent group is independently chosen from halogen, —OH, —CN, —$CF_3$, =O, —$NO_2$, benzyl, —$C(O)NR^{11}{}_2$, —$R^{11}$, $OR^{11}$, —$C(O)R^{11}$, —$COOR^{11}$, and —$NR^{11}{}_2$ wherein each $R^{11}$ is independently chosen from hydrogen and $C_{1-4}$ alkyl;
with the provisos that;
when one of $R^7$ and $R^8$ is chosen from ethyl and methyl, and the other of $R^7$ and $R^8$ is hydrogen; then $R^6$ is not —$C(CH_3)$=$CH_2$; and
when each of $R^7$ and $R^8$ is hydrogen; then $R^6$ is not chosen from —CH=$CH_2$ and 4-carboxyphenyl.

In certain embodiments of a compound of Formula (IV), each substituent group is independently chosen from halogen, —OH, —CN, —$CF_3$, —$R^{11}$, —$OR^{11}$, and —$NR^{11}{}_2$ wherein each $R^{11}$ is independently chosen from hydrogen and $C_{1-4}$ alkyl.

In certain embodiments of a compound of Formula (IV), each substituent group is independently chosen from =O, $C_{1-4}$ alkyl, and —$COOR^{11}$ wherein $R^{11}$ is chosen from hydrogen and $C_{1-4}$ alkyl.

In certain embodiments of a compound of Formula (IV), one of $R^7$ and $R^8$ is hydrogen and the other of $R^7$ and $R^8$ is $C_{1-6}$ alkyl. In certain embodiments of a compound of Formula (IV), one of $R^7$ and $R^8$ is hydrogen and the other of $R^7$ and $R^8$ is $C_{1-4}$ alkyl.

In certain embodiments of a compound of Formula (IV), one of $R^7$ and $R^8$ is hydrogen and the other of $R^7$ and $R^8$ is chosen from methyl, ethyl, n-propyl, and isopropyl. In certain embodiments of a compound of Formula (IV), each of $R^7$ and $R^8$ is hydrogen.

In certain embodiments of a compound of Formula (IV), $R^6$ is $C_{1-6}$ alkyl; and one of $R^7$ and $R^8$ is hydrogen and the other of $R^7$ and $R^8$ is $C_{1-6}$ alkyl.

In certain embodiments of a compound of Formula (IV), $R^6$ is —$OR^{10}$.

In certain embodiments of a compound of Formula (IV), $R^{10}$ is chosen from $C_{1-4}$ alkyl, cyclohexyl, and phenyl.

In certain embodiments of a compound of Formula (IV), $R^6$ is chosen from methyl, ethyl, n-propyl, and isopropyl; one of $R^7$ and $R^8$ is hydrogen and the other of $R^7$ and $R^8$ is chosen from methyl, ethyl, n-propyl, and isopropyl.

In certain embodiments of a compound of Formula (IV), $R^6$ is substituted $C_{1-2}$ alkyl, wherein each of the one or more substituent groups are chosen from —COOH, —NHC(O)CH$_2$NH$_2$, and —NH$_2$.

In certain embodiments of a compound of Formula (IV), $R^6$ is chosen from ethoxy, methylethoxy, isopropyl, phenyl, cyclohexyl, cyclohexyloxy, —CH(NH$_2$)CH$_2$COOH, —CH$_2$CH(NH$_2$)COOH, —CH(NHC(O)CH$_2$NH$_2$)—CH$_2$COOH, and —CH$_2$CH(NHC(O)CH$_2$NH$_2$)—COOH.

In certain embodiments of a compound of Formula (IV), one of $R^7$ and $R^8$ is hydrogen and the other of $R^7$ and $R^8$ is chosen from hydrogen, methyl, ethyl, n-propyl, and isopropyl; and $R^6$ is chosen from $C_{1-3}$ alkyl, substituted $C_{1-2}$ alkyl wherein each of the one or more substituent groups are chosen —COOH, —NHC(O)CH$_2$NH$_2$, and —NH$_2$, —OR$^{10}$ wherein $R^{10}$ is chosen from $C_{1-3}$ alkyl and cyclohexyl, phenyl, and cyclohexyl.

In certain embodiments of a compound of Formula (IV), the compound is chosen from:

(2E)-3-{[(2-methylpropanoyloxy)ethyl]oxycarbonyl}prop-2-enoic acid;

(2E)-3-({[(methylethyl)oxycarbonyloxy]ethyl}oxycarbonyl)prop-2-enoic acid;

2-[(2E)-3-(methoxycarbonyl)prop-2-enoyloxy]acetic acid; and a pharmaceutically acceptable salt of any of the foregoing.

Synthesis

Compounds disclosed herein may be obtained via the synthetic methods illustrated in Schemes 1 through 9. General synthetic methods useful in the synthesis of compounds described herein are available in the art. Starting materials useful for preparing compounds and intermediates thereof and/or practicing methods described herein are commercially available or can be prepared by well-known synthetic methods. The methods presented in the schemes provided by the present disclosure are illustrative rather than comprehensive. It will be apparent to those skilled in the art that many modifications, both to materials and methods, may be practiced without departing from the scope of the disclosure.

Certain of the unsubstituted, 1-mono-substituted or 1,1-bis-substituted halo acetamides useful for preparing compounds of Formula (I) are available from commercial sources. Non-commercially available unsubstituted, 1-mono-substituted or 1,1-bis-substituted halo acetamides useful for preparing compounds of Formula (I) and intermediates thereof can be prepared by well-known synthetic methods such as those described in Schemes 1 and 2.

Functionalized 1-halo acetamides useful for the preparation of MHF acetamide prodrugs of Formula (I) can be prepared according to Scheme 1:

Scheme 1

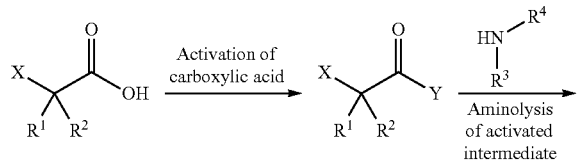

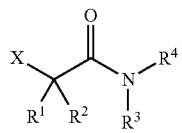

wherein X and Y are leaving groups such as halogen, and $R^1$, $R^2$, $R^3$, and $R^4$ are as defined herein. In certain embodiments of Scheme 1, X is chloro and Y is chloro or an O-acylisourea.

Chemical activation of the carboxylic acid to the corresponding carboxylic acid chloride as shown in Scheme 1 can be achieved by reaction with chlorination agents such as thionyl chloride (SOCl$_2$), oxalyl chloride (C$_2$O$_2$Cl$_2$), or phosphorous pentachloride (PCl$_5$), optionally in the presence of a suitable catalyst such as N,N-dimethylformamide (DMF), and either in substance (absence of solvent) or in an inert organic solvent such as dichloromethane (DCM) at an appropriate temperature such as from about 0° C. to about 70° C. Chemical activation of the carboxylic acid can be performed in situ and without isolating the activated substrate prior to the following aminolysis step. Optionally, the activated carboxylic acid can be isolated and/or purified using methods well known in the art, i.e. fractional distillation.

Alternatively, carbodiimide dehydration agents such as N,N'-diisopropylcarbodiimide (DIC), N,N'-dicyclohexylcarbodiimide (DCC), or 1-ethyl-3-(3-dimethylaminopropyl)carbodiimide (EDAC, EDC), optionally in the presence of a catalytic or stoichiometric amount of a suitable additive such as 4-(N,N-dimethylaminopyridine (DMAP) (Steglich esterification conditions), 1-hydroxybenzotriazole (HOBt), 1-hydroxy-7-aza-benzotriazole (HOAt), or N-hydroxysuccinimide (NHS); uronium or phosphonium salts with non-nucleophilic anions such as N-[(1H-benzotriazol-1-yl)(dimethylamino)methylene]-N-methylmetanaminium hexafluorophosphate (HBTU), N-[(dimethylamino)-1H-1,2,3-triazolo[4,5-b]pyridin-1-ylmethylene]-N-methylmetanaminium hexafluorophosphate N-oxide (HATU), N-[(1H-benzotriazol-1-yl)(dimethylamino)methylene]-N-methylmetanaminium tetrafluoroborate (TBTU), or benzotriazol-1-yl-oxytripyrrolidinophosphonium hexafluorophosphate (PyBOP), can be employed to form an activated carboxylic acid derivative. Optionally, organic tertiary bases such as triethylamine (TEA) or diisopropylethylamine (DIEA) can also be employed. The formation of the activated carboxylic acid derivative can take place in an inert solvent such as dichloromethane (DCM), N,N-dimethylformamide (DMF), N-methylpyrrolidone (NMP), N,N-dimethylacetamide (DMA, DMAc), or mixtures of any of the foregoing at an appropriate temperature such as from about 0° C. to abut 40° C.

Aminolysis of in situ generated or isolated activated carboxylic derivatives with the appropriately functionalized amine derivative (HNR$^3$R$^4$) (Scheme 2) can take place in the presence of a suitable base such as an organic tertiary base, i.e., triethylamine (TEA), diethylaminoethylamine (DIEA), pyridine, or mixtures of any of the foregoing, optionally in the presence of suitable additives such as nucleophilic acylation catalysts, i.e., 4-(N,N-dimethylaminopyridine (DMAP), and in the same or other inert solvent as used for the activation step such as dichloromethane (DCM), N,N-dimethylformamide (DMF), N-methylpyrrolidone (NMP), N,N-dimethylacetamide (DMA, DMAc), or mixtures of any of the foregoing, at an appropriate temperature such as from about 0° C. to about 70° C.

Functionalized 1-hydroxy acetamides useful for the preparation of MHF acetamide prodrugs of Formula (I) can be also prepared according to Scheme 2:

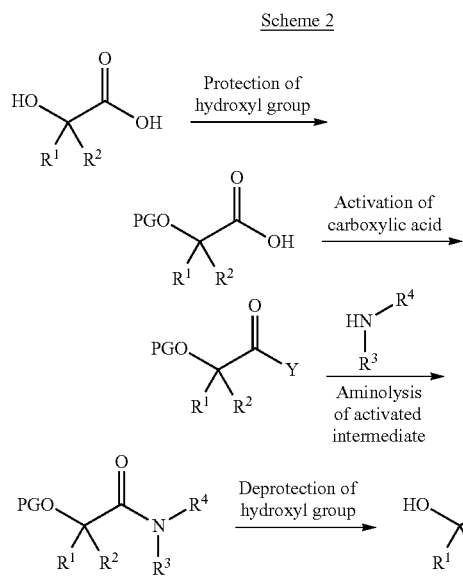

wherein PG is a hydroxyl protecting group; Y a leaving group such as chloro or an O-isourea derived radical; and $R^1$, $R^2$, $R^3$, and $R^4$ are as defined herein.

Certain of the functionalized and activated 1-hydroxy acetic acid derivatives are commercially available, i.e., benzyloxyacetic acid and tert-butyloxy lactic acid. Methods for introducing hydroxyl protecting groups (PGs) are well known in the art. Useful protecting groups to temporarily block the hydroxyl group of functionalized 1-hydroxy acetic acids include certain alkyl such as (substituted) benzyl ethers, tert-butyl ethers, trityl ether, or various silyl ethers such as tert-butyl dimethylsilyl ether, triisopropylsilyl ether, or tert-butyldiphenylsilyl ethers.

Certain protected, functionalized and activated 1-hydroxy acetic acid derivatives are commercially available, i.e., benzyloxyacetyl chloride. Alternatively, the chemical activation of the protected and functionalized 1-hydroxy acetic acid derivative to the corresponding activated carboxylic acid derivative, i.e., carboxylic acid chloride, O-acylisourea, activated esters, etc., can be achieved using similar reaction procedures and conditions as those described in Scheme 1 for the activation of functionalized 1-halo acetic acid derivatives.

Aminolysis of in situ generated or isolated protected, functionalized, and activated 1-hydroxy acetic derivatives with functionalized amines ($HNR^3R^4$) can take place using similar reaction procedures and conditions as those described in Scheme 1 for the aminolysis of functionalized, protected, and activated 1-halo acetic acid derivatives.

Orthogonal (or ordered) deprotection of the protected 1-hydroxyacetic acid derivative liberates the corresponding free hydroxyl group. Deprotection methods, procedures, and practices are well known in the art.

In certain embodiments, the protecting group can be an alkyl group such as a tert-butyl group. Deprotection may be carried out by contacting a tert-butyl protected functionalized 1-hydroxy acetamide derivative with an excess of a strong Brønsted acid such as trifluoroacetic acid (TFA) or hydrogen chloride (HCl) in an inert solvent such as dichloromethane (DCM), diethyl ether ($Et_2O$), 1,4-dioxane, or mixtures of any of the foregoing, at an appropriate temperature such as from about 0° C. to about 40° C.

In certain embodiments, the protecting group can be selected from an alkyl group such as a benzyl group. When the protecting group is a benzyl group, deprotection may be carried out by reacting the functionalized 1-hydroxy acetamide derivative with gaseous hydrogen ($H_2$) in the presence of a heterogenous catalyst, i.e., 5-10 wt-% palladium on (activated or wet coal), in a solvent such as methanol (MeOH), ethanol (EtOH), ethyl acetate (EtOAc), or mixtures of any of the foregoing, optionally in the presence of a small amount of an activator such as 1 N aq. hydrochloric acid at an appropriate temperature such as from about 0° C. to about 40° C. and under a hydrogen atmosphere at a pressure of about 15 psi to about 60 psi.

Acetamide MHF prodrugs of Formula (I) can be prepared according to Scheme 3:

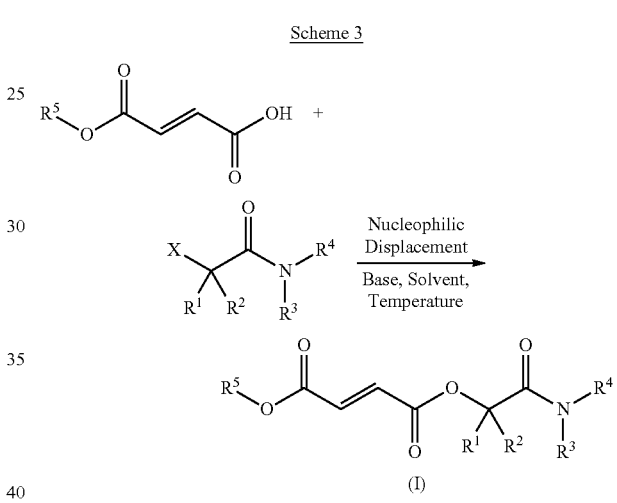

wherein X is a leaving group such as halogen, and $R^1$, $R^2$, $R^3$, $R^4$, and $R^5$ are as defined herein. In certain embodiments of Scheme 3, X is chloro and $R^5$ is alkyl such as methyl.

Nucleophilc displacement of the monoalkyl fumaric acid with the functionalized 1-halo acetamide (Scheme 1) as shown in Scheme 3 can take place in the presence of an inorganic base such as an alkali carbonate such as cesium hydrogencarbonate ($CsHCO_3$), cesium carbonate ($Cs_2CO_3$), or potassium carbonate ($K_2CO_3$). Optionally, organic tertiary bases such as triethylamine (TEA), diisopropylethylamine (DIEA), or amidine; guanidine-based bases such as 1,5-diazabicyclo[4.3.0]non-5-ene (DBN), or 1,8-diazabicyclo[5.4.0]undec-7-ene (DBU), 1,1,3,3-tetramethylguanidine (TMG); silver salts such silver(I) oxide ($Ag_2O$) or silver(I) carbonate ($Ag_2CO_3$); or other halide scavengers known in the art can be employed. The corresponding alkali, tri- and tetraalkylammonoium, amidine, or guanide salts of the monoalkyl fumarate can be generated in situ or, alternatively, can be prepared separately. The reaction can take place in an inert solvent such as N,N-dimethylformamide (DMF), N-methylpyrrolidone (NMP), N,N-dimethylacetamide (DMA, DMAc), dimethylsulfoxide (DMSO), tetrahydrofuran (THF), toluene, or mixtures of any of the foregoing at an appropriate temperature such as from about room temperature to about 70° C.

Acetamide MHF prodrugs of Formula (I) can also be prepared according to Scheme 4:

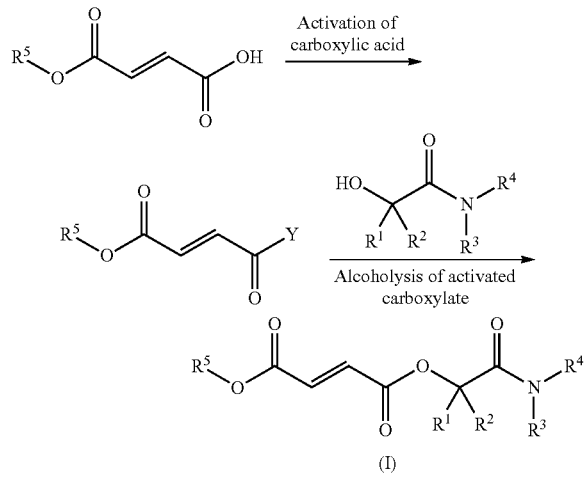

wherein Y is a suitable leaving group such as halogen, an O-acylisourea, various triazolol esters, or others; and $R^1$, $R^2$, $R^3$, $R^4$, and $R^5$ are as defined herein. In certain embodiments of Scheme 4, Y is chloro and $R^5$ is alkyl such as methyl.

Chemical activation of the carboxylic acid to the corresponding carboxylic acid chloride as shown in Scheme 4 can be accomplished by reaction with a chlorination agent such as thionyl chloride ($SOCl_2$), oxalyl chloride ($C_2O_2Cl_2$), phosphorous pentachloride ($PCl_5$), or others, optionally in the presence of a catalyst such as N,N-dimethylformamide (DMF), and either in substance (absence of solvent) or in an inert organic solvent such as dichloromethane (DCM) at an appropriate temperature such as from about 0° C. to about 70° C. Chemical activation of the carboxylic acid as shown in Scheme 4 can be performed in situ without isolating the activated substrate prior to the subsequent alcoholysis step. Optionally, the activated carboxylic acid chloride can be isolated and/or purified using methods well known in the art, i.e. fractional distillation.

Alternatively, carbodiimide dehydration agents such as N,N'-diisopropylcarbodiimide (DIC), N,N'-dicyclohexylcarbodiimide (DCC), or 1-ethyl-3-(3-dimethylaminopropyl)carbodiimide (EDAC, EDC), optionally in the presence of a catalytic or stoichiometric amount of an additive such as 4-(N,N-dimethylaminopyridine (DMAP) (Steglich esterification conditions), 1-hydroxybenzotriazole (HOBt), 1-hydroxy-7-aza-benzotriazole (HOAt), or N-hydroxysuccinimide (HOSu); a uronium or phosphonium salt with non-nucleophilic anions such as N-[(1H-benzotriazol-1-yl)(dimethylamino)methylene]-N-methylmetanaminium hexafluorophosphate (HBTU), N-[(dimethylamino)-1H-1,2,3-triazolo[4,5-b]pyridin-1-ylmethylene]-N-methylmetanaminium hexafluorophosphate N-oxide (HATU), N-[(1H-benzotriazol-1-yl)(dimethylamino)methylene]-N-methylmetanaminium tetrafluoroborate (TBTU), or benzotriazol-1-yl-oxytripyrrolidinophosphonium hexafluorophosphate (PyBOP), can be employed to form an activated monoalkyl fumarate derivative. Optionally, organic tertiary bases such as triethylamine (TEA) or diethylaminoethylamine (DIEA) can also be employed. The formation of activated monoalkyl fumarate derivatives can take place in an inert solvent such as dichloromethane (DCM), N,N-dimethylformamide (DMF), N-methylpyrrolidone (NMP), N,N-dimethylacetamide (DMA, DMAc), or mixtures of any of the foregoing at an appropriate temperature such as from about room temperature to about 70° C.

Alcoholysis of the activated monoalkyl fumarate derivative with a functionalized hydroxy acetamide derivative (Scheme 2) can take place in the presence of a base, for example, an organic tertiary base such as, triethylamine (TEA), diethylaminoethylamine (DIEA), or pyridine, optionally in the presence of an additive such as a nucleophilic acylation catalyst, i.e., 4-(N,N-dimethylaminopyridine (DMAP) (Steglich esterification conditions), and in the same or other inert solvent as used for the activation step such as dichloromethane (DCM), N,N-dimethylformamide (DMF), N-methylpyrrolidone (NMP), N,N-dimethylacetamide (DMA, DMAc), or mixtures of any of the foregoing at an appropriate temperature such as from about 0° C. to about 70° C.

Acetamide MHF prodrugs of Formula (I) can also be prepared according to Scheme 5:

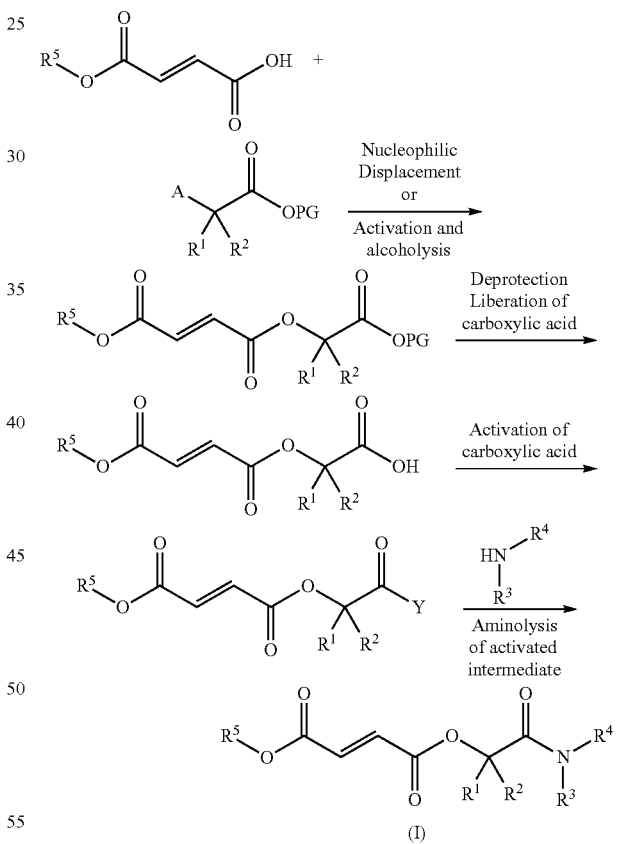

wherein A is either a leaving group such as halogen or a nucleophilic coupling group such as hydroxyl; Y is a leaving group such as halogen, a O-acylisourea, various triazolol esters, or others; PG is a carboxyl protecting group; and $R^1$, $R^2$, $R^3$, $R^4$, and $R^5$ are as defined herein. In certain embodiments of Scheme 5, X is bromo, PG is tert-butyl, each of $R^1$ and $R^2$ is hydrogen, and the electrophile is tert-butyl bromoacetate. In certain embodiments of Scheme 5, Y is chloro or O-acylisourea derived from 1-ethyl-3-(3-dimethylaminopropyl)carbodiimide (EDAC), and $R^5$ is alkyl such as methyl.

The nucleophilc displacement reaction of the monoalkyl fumaric acid with a protected and functionalized 1-halo acetic acid derivative, i.e., commercially available tert-butyl bromoacetate or others, can take place using similar reaction procedures and conditions as those described in Scheme 3 for the direct formation of functionalized acetamide MHF prodrugs of Formula (I) from a monoalkyl fumaric acid and an appropriately functionalized 1-halo acetamide.

Alcoholysis of an intermediate activated monoalkyl fumaric acid derivative and a protected and functionalized 1-hydroxy acetic acid derivative can take place using similar reaction procedures and conditions as those used in Scheme 4 for the direct formation of functionalized acetamide MHF prodrugs of Formula (I) from a monoalkyl fumaric acid and an appropriately functionalized 1-hydroxy acetamide.

Orthogonal (or ordered) deprotection of a protected monoalkyl fumaric acid-functionalized acetic acid derivative liberates the corresponding free monoalkyl fumarate ester intermediate bearing a free carboxylic acid moiety. When the protecting group is a tert-butyl group, deprotection may be carried out by contacting the tert-butyl protected fumaric acid derivative with an excess of a strong Brønsted acid such as trifluoroacetic acid (TFA) or hydrogen chloride (HCl) in an inert solvent such as dichloromethane (DCM), diethyl ether ($Et_2O$), 1,4-dioxane, or mixtures of any of the foregoing, at an appropriate temperature such as from about 0° C. to about 40° C.

Chemical activation of the liberated monoalkyl fumarate-functionalized hydroxyacetic derivative (carboxylic acid) to the corresponding activated carboxylic acid derivative, i.e., carboxylic acid chloride, O-acylisourea, activated esters, etc., can be accomplished using reaction procedures and conditions similar to those described in Scheme 4 for the activation of monoalkyl fumaric acid direct formation of functionalized acetamide MHF prodrugs of Formula (I) from the monoalkyl fumaric acid and the corresponding functionalized hydroxyl acetamide.

Aminolysis of in situ generated or isolated activated monoalkyl fumarate functionalized hydroxyacetic derivatives with functionalized amines ($HNR^3R^4$) can take place using reaction procedures and conditions similar to those described in Schemes 1 and 2 for the aminolysis of protected, suitably functionalized and activated hydroxy acetic acid derivatives.

Certain of the functionalized 1-haloalkyl carboxylates (1-acyloxyalkyl halides) or functionalized 1-alkoxycarbonyloxyalkyl halides useful for preparing compounds of Formula (II) are available from commercial sources. Non-commercially available 1-haloalkyl carboxylates (1-acyloxyalkyl halides) or functionalized 1-alkoxycarbonyloxyalkyl halides can be prepared by methods well known in the art and are briefly described in Schemes 6 and 7.

1-Acyloxyalky halides useful for the preparation of MHF prodrugs of Formula (II) can be prepared according to Scheme 6:

Scheme 6

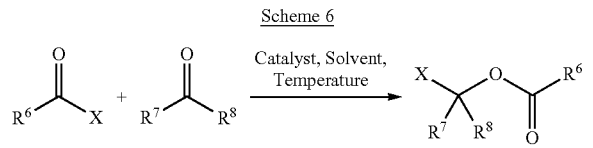

wherein X is a leaving group such as halogen; and $R^6$, $R^7$, $R^8$ are as defined herein. In certain embodiments of Scheme 6, X is chloro and $R^6$ is 2-[methyl (2E)but-2-ene-4-ate]yl; one of $R^7$ and $R^8$ is hydrogen and the other of $R^7$ and $R^8$ is alkyl.

Functionalized 1-haloalkyl carboxylates (1-acyloxyalkyl halides) may be prepared by contacting a functionalized carboxylic acid halide such as a carboxylic acid chloride with a functionalized carbonyl compound such as an aldehyde in the presence of a Lewis acid catalyst such as anhydrous zinc chloride ($ZnCl_2$) in an inert solvent such as dichloromethane (DCM) at a temperature from about −10° C. to room temperature. The 1-chloroalkyl carboxylates (1-acyloxyalkyl chlorides) may be used directly or may be isolated and purified by methods well known in the art such as by fractional distillation or silica gel column chromatography.

1-Alkoxy- and 1-aryloxycarbonyloxyalkyl halides useful for the preparation of MHF prodrugs of Formula (II) can be prepared according to Scheme 7:

Scheme 7

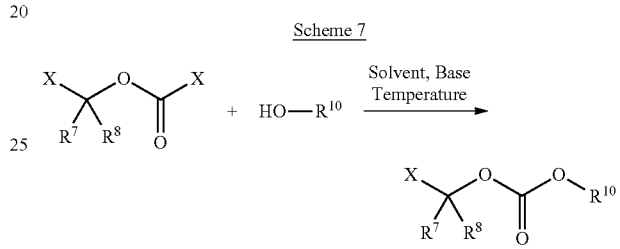

wherein X is a leaving group such as halogen, and $R^7$, $R^8$, and $R^{10}$ are as defined herein. In certain embodiments of Scheme 7, X is chloro and $R^{10}$ together with the oxygen atom to which it is bonded is equivalent to $R^6$, which is defined herein.

Functionalized 1-alkoxy- or aryloxycarbonyloxyalkyl halides may be prepared by contacting a functionalized haloalkyl halo formate such as a functionalized chloro alkyl- or aryl chloroformate with a functionalized alcohol or phenol ($HOR^{10}$) in the presence of a base such as an organic secondary and tertiary base, i.e., dicyclohexyl amine (DCHA), triethylamine (TEA), diisopropylethylamine (DIEA, Hünigsbase), pyridine, in an inert solvent such as dichloromethane (DCM) at a temperature from about −10° C. to room temperature. The 1-alkoxy- or aryloxycarbonyloxyalkyl halides may be used directly or may be isolated and purified by methods well known in the art such as by fractional distillation or silica gel column chromatography.

Acyloxyalkyl and alkoxycarbonyloxyalkyl MHF prodrugs of Formula (II) can be prepared according to Scheme 8:

Scheme 8

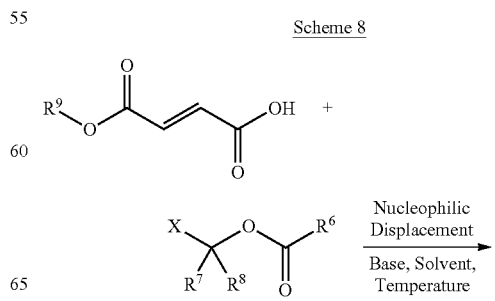

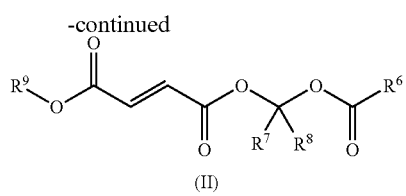

(II)

wherein X is a leaving group such as halogen, and $R^6$, $R^7$, $R^8$, and $R^9$ are as defined herein.

Nucleophilic displacement of the monoalkyl fumaric acid with a functionalized 1-halo (Scheme 1) as shown in Scheme 8 can take place in the presence of an inorganic base such as an alkali carbonate, i.e., cesium bicarbonate ($CsHCO_3$), cesium carbonate ($Cs_2CO_3$), or potassium carbonate ($K_2CO_3$). Alternatively, organic secondary and tertiary bases such as dicyclohexyl amine (DCHA), triethylamine (TEA), diisopropylethylamine (DIEA), amidine or guanidine-based bases such as 1,5-diazabicyclo[4.3.0]non-5-ene (DBN), 1,8-diazabicyclo[5.4.0]undec-7-ene (DBU), or 1,1,3,3-tetramethylguanidine (TMG); silver salts such silver(I) oxide ($Ag_2O$) or silver(I) carbonate ($Ag_2CO_3$); or other halide scavengers known in the art can be employed. The corresponding alkali, tri- and tetraalkylammonoium, amidine, or guanide salts of the monoalkyl fumarate can be generated in situ or, alternatively, can be prepared separately. The reaction can take place in an inert solvent such as N,N-dimethylformamide (DMF), N-methylpyrrolidone (NMP), N,N-dimethylacetamide (DMA, DMAc), dimethylsulfoxide (DMSO), or tetrahydrofuran (THF), toluene, or mixtures of any of the foregoing at an appropriate temperature such as from about room temperature to about 70° C.

Fumaric acid glycolamide monoesters of Formula (III) or acyloxyalkyl- and alkoxy- or aryloxycarbonyloxyalkyl fumaric acid monoesters of Formula (IV) can be prepared according to Scheme 9:

Scheme 9

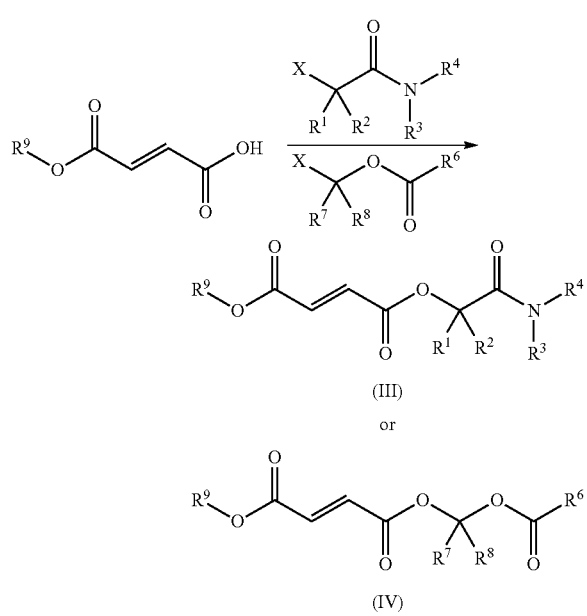

wherein X is a suitable leaving group such as chloro; and $R^1$, $R^2$, $R^3$, $R^4$, $R^6$, $R^7$, $R^8$, and $R^9$ are as defined herein. In certain embodiments of Scheme 9, X is chloro, and $R^9$ is selected from hydrogen or tert-butyl (tBu) and the fumaric acid derivative is either fumaric acid or mono tert-butyl fumarate.

The coupling of fumaric acid or monoalkyl fumarates, i.e., mono tert-butyl fumarate, with functionalized 1-halo acetamide derivatives, functionalized 1-haloalkyl carboxylates (1-acyloxyalkyl halides), or 1-alkoxy- or aryloxycarbonyloxyalkyl halides, can take place using reaction procedures and conditions similar to those described in Schemes 3 and 8 for the direct formation of functionalized acetamide MHF prodrugs of Formula (I) (Scheme 3) or acyloxyalkyl or alkoxy-aryloxycarbonyloxyalkyl MHF prodrugs of Formula (II) (Scheme 8).

In certain embodiments where $R^9$ is alkyl, such as tert-butyl, orthogonal (or ordered) deprotection (or liberation of the free carboxylic acid) from the corresponding functionalized acetamide or acyloxyalkyl or alkoxy/aryloxycarbonyloxyalkyl tert-butyl fumarates may be accomplished using reaction procedures and conditions similar to those described in Scheme 5.

Pharmaceutical Compositions

Pharmaceutical compositions provided by the present disclosure may comprise a therapeutically effective amount of a compound of Formulae (I)-(IV) together with a suitable amount of one or more pharmaceutically acceptable vehicles so as to provide a composition for proper administration to a patient. Suitable pharmaceutical vehicles are described in the art.

In certain embodiments, a compound of Formulae (I)-(IV) may be incorporated into pharmaceutical compositions to be administered orally. Oral administration of such pharmaceutical compositions may result in uptake of a compound of Formulae (I)-(IV) throughout the intestine and entry into the systemic circulation. Such oral compositions may be prepared in a manner known in the pharmaceutical art and comprise a compound of Formulae (I)-(IV) and at least one pharmaceutically acceptable vehicle. Oral pharmaceutical compositions may include a therapeutically effective amount of a compound of Formulae (I)-(IV) and a suitable amount of a pharmaceutically acceptable vehicle, so as to provide an appropriate form for administration to a patient.

Compounds of Formulae (I)-(IV) may be incorporated into pharmaceutical compositions to be administered by any other appropriate route of administration including intradermal, intramuscular, intraperitoneal, intravenous, subcutaneous, intranasal, epidural, oral, sublingual, intracerebral, intravaginal, transdermal, rectal, inhalation, or topical.

Pharmaceutical compositions comprising a compound of Formulae (I)-(IV) and may be manufactured by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers, diluents, excipients, or auxiliaries, which facilitate processing of compounds of Formulae (I)-(IV) or crystalline forms thereof and one or more pharmaceutically acceptable vehicles into formulations that can be used pharmaceutically. Proper formulation is dependent upon the route of administration chosen. Pharmaceutical compositions provided by the present disclosure may take the form of solutions, suspensions, emulsion, tablets, pills, pellets, capsules, capsules containing liquids, powders, sustained-release formulations, suppositories, emulsions, aerosols, sprays, suspensions, or any other form suitable for administration to a patient.

Pharmaceutical compositions provided by the present disclosure may be formulated in a unit dosage form. A unit dosage form refers to a physically discrete unit suitable as a unitary dose for patients undergoing treatment, with each unit containing a predetermined quantity of a compound of Formulae (I)-(IV) calculated to produce an intended therapeutic effect. A unit dosage form may be for a single daily dose, for administration 2 times per day, or one of multiple daily doses, e.g., 3 or more times per day. When multiple daily doses are used, a unit dosage form may be the same or different for each dose. One or more dosage forms may comprise a dose, which may be administered to a patient at a single point in time or during a time interval.

Pharmaceutical compositions comprising a compound of Formulae (I)-(IV) may be formulated for immediate release.

In certain embodiments, an oral dosage form provided by the present disclosure may be a controlled release dosage form. Controlled delivery technologies can improve the absorption of a drug in a particular region or regions of the gastrointestinal tract. Controlled drug delivery systems may be designed to deliver a drug in such a way that the drug level is maintained within a therapeutically effective window and effective and safe blood levels are maintained for a period as long as the system continues to deliver the drug with a particular release profile in the gastrointestinal tract. Controlled drug delivery may produce substantially constant blood levels of a drug over a period of time as compared to fluctuations observed with immediate release dosage forms. For some drugs, maintaining a constant blood and tissue concentration throughout the course of therapy is the most desirable mode of treatment. Immediate release of drugs may cause blood levels to peak above the level required to elicit a desired response, which may waste the drug and may cause or exacerbate toxic side effects. Controlled drug delivery can result in optimum therapy, and not only can reduce the frequency of dosing, but may also reduce the severity of side effects. Examples of controlled release dosage forms include dissolution controlled systems, diffusion controlled systems, ion exchange resins, osmotically controlled systems, erodable matrix systems, pH independent formulations, gastric retention systems, and the like.

An appropriate oral dosage form for a particular pharmaceutical composition provided by the present disclosure may depend, at least in part, on the gastrointestinal absorption properties of a compound of Formulae (I)-(IV) the stability of a compound of Formulae (I)-(IV) in the gastrointestinal tract, the pharmacokinetics of a compound of Formulae (I)-(IV) and the intended therapeutic profile. An appropriate controlled release oral dosage form may be selected for a particular compound of Formulae (I)-(IV). For example, gastric retention oral dosage forms may be appropriate for compounds absorbed primarily from the upper gastrointestinal tract, and sustained release oral dosage forms may be appropriate for compounds absorbed primarily from the lower gastrointestinal tract. Certain compounds are absorbed primarily from the small intestine. In general, compounds traverse the length of the small intestine in about 3 to 5 hours. For compounds that are not easily absorbed by the small intestine or that do not dissolve readily, the window for active agent absorption in the small intestine may be too short to provide a desired therapeutic effect.

In certain embodiments, pharmaceutical compositions provided by the present disclosure may be practiced with dosage forms adapted to provide sustained release of a compound of Formulae (I)-(IV) upon oral administration. Sustained release oral dosage forms may be used to release drugs over a prolonged time period and are useful when it is desired that a drug or drug form be delivered to the lower gastrointestinal tract. Sustained release oral dosage forms include any oral dosage form that maintains therapeutic concentrations of a drug in a biological fluid such as the plasma, blood, cerebrospinal fluid, or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art.

An appropriate dose of a compound of Formulae (I)-(IV) or pharmaceutical composition comprising a compound of Formulae (I)-(IV) may be determined according to any one of several well-established protocols. For example, animal studies such as studies using mice, rats, dogs, and/or monkeys may be used to determine an appropriate dose of a pharmaceutical compound. Results from animal studies may be extrapolated to determine doses for use in other species, such as for example, humans.

Uses

Compounds of Formulae (I)-(IV) are prodrugs of MHF. Thus, compounds of Formulae (I)-(IV) and pharmaceutical compositions thereof may be administered to a patient suffering from any disease including a disorder, condition, or symptom for which MHF is known or hereafter discovered to be therapeutically effective. Indications for which MHF has been prescribed, and hence for which a compound of Formulae (I)-(IV), or pharmaceutical compositions thereof are also expected to be effective, include psoriasis. Other indications for which compounds of Formulae (I)-(IV) may be therapeutically effective include multiple sclerosis, an inflammatory bowel disease, asthma, chronic obstructive pulmonary disease, and arthritis.

Methods of treating a disease in a patient provided by the present disclosure comprise administering to a patient in need of such treatment a therapeutically effective amount of a MHF prodrug of Formulae (I)-(IV). Compounds of Formulae (I)-(IV) or pharmaceutical compositions thereof may provide therapeutic or prophylactic plasma and/or blood concentrations of MHF following administration to a patient.

MHF prodrugs of Formulae (I)-(IV) may be included in a pharmaceutical composition and/or dosage form adapted for oral administration, although MHF prodrug of Formulae (I)-(IV) may also be administered by any other appropriate route, such as for example, by injection, infusion, inhalation, transdermal, or absorption through epithelial or mucosal membranes (e.g., oral, rectal, and/or intestinal mucosa).

MHF prodrugs of Formulae (I)-(IV) may be administered in an amount and using a dosing schedule as appropriate for treatment of a particular disease. Daily doses of a MHF prodrug of Formulae (I)-(IV) may range from about 0.01 mg/kg to about 50 mg/kg, from about 0.1 mg/kg to about 50 mg/kg, from about 1 mg/kg to about 50 mg/kg, and in certain embodiments, from about 5 mg/kg to about 25 mg/kg. In certain embodiments, MHF prodrugs of Formulae (I)-(IV) may be administered at a dose over time from about 1 mg to about 5 g per day, from about 10 mg to about 4 g per day, and in certain embodiments from about 20 mg to about 2 g per day. An appropriate dose of a MHF prodrug of Formulae (I)-(IV) may be determined based on several factors, including, for example, the body weight and/or condition of the patient being treated, the severity of the disease being treated, the incidence and/or severity of side effects, the manner of administration, and the judgment of the prescribing physician. Appropriate dose ranges may be determined by methods known to those skilled in the art.

MHF prodrugs of Formulae (I)-(IV) may be assayed in vitro and in vivo for the desired therapeutic or prophylactic activity prior to use in humans. In vivo assays, for example using appropriate animal models, may also be used to determine whether administration of a MHF prodrug of Formulae (I)-(IV) is therapeutically effective.

In certain embodiments, a therapeutically effective dose of a MHF prodrug of Formulae (I)-(IV) may provide therapeutic benefit without causing substantial toxicity including adverse side effects. Toxicity of MHF prodrugs of Formulae (I)-(IV) and/or metabolites thereof may be determined using standard pharmaceutical procedures and may be ascertained by those skilled in the art. The dose ratio between toxic and therapeutic effect is the therapeutic index. A dose of a MHF prodrug of Formulae (I)-(IV) may be within a range capable of establishing and maintaining a therapeutically effective circulating plasma and/or blood concentration of a MHF prodrug of Formulae (I)-(IV) that exhibits little or no toxicity.

MHF prodrug of Formulae (I)-(IV) may be used to treat diseases, disorders, conditions, and symptoms of any of the foregoing for which MHF is known to provide or is later found to provide therapeutic benefit. MHF is known to be effective in treating psoriasis, multiple sclerosis, an inflammatory bowel disease, asthma, chronic obstructive pulmonary disease, and arthritis. Hence, MHF prodrugs of Formulae (I)-(IV) may be used to treat any of the foregoing diseases and disorders. The underlying etiology of any of the foregoing diseases being treated may have a multiplicity of origins. Further, in certain embodiments, a therapeutically effective amount of one or more compounds of Formulae (I)-(IV) may be administered to a patient, such as a human, as a preventative measure against various diseases or disorders. Thus, a therapeutically effective amount of one or more compounds of Formulae (I)-(IV) may be administered as a preventative measure to a patient having a predisposition for and/or history of immunological, autoimmune, and/or inflammatory diseases including psoriasis, asthma and chronic obstructive pulmonary diseases, cardiac insufficiency including left ventricular insufficiency, myocardial infarction and angina pectoris, mitochondrial and neurodegenerative diseases such as Parkinson's disease, Alzheimer's disease, Huntington's disease, retinopathia pigmentosa and mitochondrial encephalomyopathy, transplantation rejection, autoimmune diseases including multiple sclerosis, ischemia and reperfusion injury, AGE-induced genome damage, inflammatory bowel diseases such as Crohn's disease and ulcerative colitis; and NF-κB mediated diseases.

Psoriasis

Psoriasis is characterized by hyperkeratosis and thickening of the epidermis as well as by increased vascularity and infiltration of inflammatory cells in the dermis. Psoriasis vulgaris manifests as silvery, scaly, erythematous plaques on typically the scalp, elbows, knees, and buttocks. Guttate psoriasis occurs as tear-drop size lesions.

Fumaric acid esters are recognized for the treatment of psoriasis and dimethyl fumarate is approved for the systemic treatment of psoriasis in Germany (Mrowietz and Asadullah, *Trends Mol Med* 2005, 11(1), 43-48; and Mrowietz et al., *Br J Dermatology* 1999, 141, 424-429).

Efficacy of MHF prodrugs for treating psoriasis can be determined using animal models and in clinical trials.

Inflammatory Arthritis

Inflammatory arthritis includes diseases such as rheumatoid arthritis, juvenile rheumatoid arthritis (juvenile idiopathic arthritis), psoriatic arthritis, and ankylosing spondylitis produce joint inflammation. The pathogenesis of immune-mediated inflammatory diseases including inflammatory arthritis is believed to involve TNF and NK-κB signaling pathways (Tracey et al., *Pharmacology & Therapeutics* 2008, 117, 244-279). DMF has been shown to inhibit TNF and inflammatory diseases including inflammatory arthritis are believed to involve TNF and NK-κB signaling and therefore may be useful in treating inflammatory arthritis (Lowewe et al., *J Immunology* 2002, 168, 4781-4787).

The efficacy of MHF prodrugs for treating inflammatory arthritis can be determined using animal models and in clinical trials.

Multiple Sclerosis

Multiple sclerosis (MS) is an inflammatory autoimmune disease of the central nervous system caused by an autoimmune attack against the isolating axonal myelin sheets of the central nervous system. Demyelination leads to the breakdown of conduction and to severe disease with destruction of local axons and irreversible neuronal cell death. The symptoms of MS are highly varied with each individual patient exhibiting a particular pattern of motor, sensible, and sensory disturbances. MS is typified pathologically by multiple inflammatory foci, plaques of demyelination, gliosis, and axonal pathology within the brain and spinal cord, all of which contribute to the clinical manifestations of neurological disability (see e.g., Wingerchuk, *Lab Invest* 2001, 81, 263-281; and Virley, *NeuroRx* 2005, 2(4), 638-649). Although the causal events that precipitate MS are not fully understood, evidence implicates an autoimmune etiology together with environmental factors, as well as specific genetic predispositions. Functional impairment, disability, and handicap are expressed as paralysis, sensory and octintive disturbances spasticity, tremor, a lack of coordination, and visual impairment, which impact on the quality of life of the individual. The clinical course of MS can vary from individual to individual, but invariably the disease can be categorized in three forms: relapsing-remitting, secondary progressive, and primary progressive.

Studies support the efficacy of FAEs for treating MS and are undergoing phase II clinical testing (Schimrigk et al., *Eur J Neurology* 2006, 13, 604-610; and Wakkee and Thio, *Current Opinion Investigational Drugs* 2007, 8(11), 955-962).

Assessment of MS treatment efficacy in clinical trials can be accomplished using tools such as the Expanded Disability Status Scale and the MS Functional as well as magnetic resonance imaging lesion load, biomarkers, and self-reported quality of life Animal models of MS shown to be useful to identify and validate potential therapeutics include experimental autoimmune/allergic encephalomyelitis (EAE) rodent models that simulate the clinical and pathological manifestations of MS and nonhuman primate EAE models.

Inflammatory Bowel Disease (Crohn's Disease, Ulcerative Colitis)

Inflammatory bowel disease (IBD) is a group of inflammatory conditions of the large intestine and in some cases, the small intestine that includes Crohn's disease and ulcerative colitis. Crohn's disease, which is characterized by areas of inflammation with areas of normal lining in between, can affect any part of the gastrointestinal tract from the mouth to the anus. The main gastrointestinal symptoms are abdominal pain, diarrhea, constipation, vomiting, weight loss, and/or weight gain. Crohn's disease can also cause skin rashes, arthritis, and inflammation of the eye. Ulcerative colitis is characterized by ulcers or open sores in the large intestine or colon. The main symptom of ulcerative colitis is typically constant diarrhea with mixed blood of gradual onset. Other types of intestinal bowel disease include collagenous colitis, lymphocytic colitis, ischaemic colitis, diversion colitis, Behcet's colitis, and indeterminate colitis.

FAEs are inhibitors of NF-κB activation and therefore may be useful in treating inflammatory diseases such as Crohn's disease and ulcerative colitis (Atreya et al., *J Intern Med* 2008, 263(6), 59106).

The efficacy of MHF prodrugs for treating inflammatory bowel disease can be evaluated using animal models and in clinical trials. Useful animal models of inflammatory bowel disease are known.

Asthma

Asthma is reversible airway obstruction in which the airway occasionally constricts, becomes inflamed, and is lined with an excessive amount of mucus. Symptoms of asthma include dyspnea, wheezing, chest tightness, and cough. Asthma episodes may be induced by airborne allergens, food allergies, medications, inhaled irritants, physical exercise, respiratory infection, psychological stress, hormonal changes, cold weather, or other factors.

As an inhibitor of NF-κB activation and as shown in animal studies (Joshi et al., US 2007/0027076) FAEs may be useful in treating pulmonary diseases such as asthma and chronic obstructive pulmonary disorder.

The efficacy of MHF prodrugs of Formulae (I)-(IV) for treating asthma can be assessed using animal models and in clinical trials.

Chronic Obstructive Pulmonary Disease

Chronic obstructive pulmonary disease (COPD), also known as chronic obstructive airway disease, is a group of diseases characterized by the pathological limitation of airflow in the airway that is not fully reversible, and includes conditions such as chronic bronchitis, emphysema, as well as other lung disorders such as asbestosis, pneumoconiosis, and pulmonary neoplasms (see, e.g., Barnes, *Pharmacological Reviews* 2004, 56(4), 515-548). The airflow limitation is usually progressive and associated with an abnormal inflammatory response of the lungs to noxious particles and gases. COPD is characterized by a shortness of breath the last for months or years, possibly accompanied by wheezing, and a persistent cough with sputum production. COPD is most often caused by tobacco smoking, although it can also be caused by other airborne irritants such as coal dust, asbestos, urban pollution, or solvents. COPD encompasses chronic obstructive bronchiolitis with fibrosis and obstruction of small airways, and emphysema with enlargement of airspaces and destruction of lung parenchyma, loss of lung elasticity, and closure of small airways.

The efficacy of administering at least one compound of Formula (I) or Formula (II) for treating chronic obstructive pulmonary disease may be assessed using animal models of chronic obstructive pulmonary disease and in clinical studies. For example, murine models of chronic obstructive pulmonary disease are known.

Neurodegenerative Disorders

Neurodegenerative diseases such as Parkinson's disease, Alzheimer's disease, Huntington's disease and amyoptrophic lateral sclerosis are characterized by progressive dysfunction and neuronal death. NF-κB inhibition has been proposed as a therapeutic target for neurodegenerative diseases (Camandola and Mattson, *Expert Opin Ther Targets* 2007, 11(2), 123-32).

Parkinson's Disease

Parkinson's disease is a slowly progressive degenerative disorder of the nervous system characterized by tremor when muscles are at rest (resting tremor), slowness of voluntary movements, and increased muscle tone (rigidity). In Parkinson's disease, nerve cells in the basal ganglia, e.g., substantia nigra, degenerate, and thereby reduce the production of dopamine and the number of connections between nerve cells in the basal ganglia. As a result, the basal ganglia are unable to smooth muscle movements and coordinate changes in posture as normal, leading to tremor, incoordination, and slowed, reduced movement (bradykinesia) (Blandini, et al., *Mol. Neurobiol.* 1996, 12, 73-94).

The efficacy of compounds of Formulae (I)-(IV) for treating Parkinson's disease may be assessed using animal and human models of Parkinson's disease and in clinical studies.

Alzheimer's Disease

Alzheimer's disease is a progressive loss of mental function characterized by degeneration of brain tissue, including loss of nerve cells and the development of senile plaques and neurofibrillary tangles. In Alzheimer's disease, parts of the brain degenerate, destroying nerve cells and reducing the responsiveness of the maintaining neurons to neurotransmitters. Abnormalities in brain tissue consist of senile or neuritic plaques, e.g., clumps of dead nerve cells containing an abnormal, insoluble protein called amyloid, and neurofibrillary tangles, twisted strands of insoluble proteins in the nerve cell.

The efficacy of compounds of Formulae (I)-(IV) for treating Alzheimer's disease may be assessed using animal and human models of Alzheimer's disease and in clinical studies.

Huntington's Disease

Huntington's disease is an autosomal dominant neurodegenerative disorder in which specific cell death occurs in the neostriatum and cortex (Martin, *N Engl J Med* 1999, 340, 1970-80). Onset usually occurs during the fourth or fifth decade of life, with a mean survival at age of onset of 14 to 20 years. Huntington's disease is universally fatal, and there is no effective treatment. Symptoms include a characteristic movement disorder (Huntington's chorea), cognitive dysfunction, and psychiatric symptoms. The disease is caused by a mutation encoding an abnormal expansion of CAG-encoded polyglutamine repeats in the protein, huntingtin.

The efficacy of compounds of Formulae (I)-(IV) for treating Huntington's disease may be assessed using animal and human models of Huntington's disease and in clinical studies.

Amyotrophic Lateral Sclerosis

Amyotrophic lateral sclerosis (ALS) is a progressive neurodegenerative disorder characterized by the progressive and specific loss of motor neurons in the brain, brain stem, and spinal cord (Rowland and Schneider, *N Engl J Med* 2001, 344, 1688-1700). ALS begins with weakness, often in the hands and less frequently in the feet that generally progresses up an arm or leg. Over time, weakness increases and spasticity develops characterized by muscle twitching and tightening, followed by muscle spasms and possibly tremors. The average age of onset is 55 years, and the average life expectancy after the clinical onset is 4 years. The only recognized treatment for ALS is riluzole, which can extend survival by only about three months.

The efficacy compounds of Formulae (I)-(IV) for treating ALS may be assessed using animal and human models of ALS and in clinical studies.

Others

Other diseases and conditions for which compounds of Formulae (I)-(IV) can be useful in treating include rheumatica, granuloma annulare, lupus, autoimmune carditis, eczema, sarcoidosis, and autoimmune diseases including acute disseminated encephalomyelitis, Addison's disease, alopecia areata, ankylosing spondylitis, antiphospholipid antibody syndrome, autoimmune hemolytic anemia, autoimmune hepatitis, autoimmune inner ear disease, bullous pemphigoid, Behcet's disease, celiac disease, Chagas disease, chronic obstructive pulmonary disease, Crhon's disease, dermatomyositis, diabetes mellitus type I, endometriosis, Goodpasture's syndrome, Graves' disease, Guillain-Barre syndrome, Hashimoto's disease, hidradenitis suppurativea, Kawasaki disease, IgA neuropathy, idiopathic thrombocytopenic purpura, interstitial cystitis, lupus erythematosus, mixed connective tissue disease, morphea, multiple sclerosis, myasthenia gravis, narcolepsy, neuromyotonia, pemphigus vulgaris, pernicious anaemia, psoriasis, psoriatic arthritis, polymyositis, primary biliary cirrhosis, rheumatoid arthritis, schizophrena, scleroderma, Sjogren's syndrome, stiff person syndrome, temporal arteritis, ulcerative colitis, vasculitis, vitiligo, and Wegener's granulomatosis.

Administration

MHF prodrugs of Formulae (I)-(IV) and pharmaceutical compositions thereof may be administered orally or by any other appropriate route, for example, by infusion or bolus injection, by absorption through epithelial or mucocutaneous linings (e.g., oral mucosa, rectal, and intestinal mucosa, etc.). Other suitable routes of administration include, but are not limited to, intradermal, intramuscular, intraperitoneal, intravenous, subcutaneous, intranasal, epidural, oral, sublingual, intracerebral, intravaginal, transdermal, rectal, inhalation, or topical.

Administration may be systemic or local. Various delivery systems are known, e.g., encapsulation in liposomes, microparticles, microcapsules, capsules, etc.) that may be used to administer a compound and/or pharmaceutical composition.

The amount of a MHF prodrug of Formulae (I)-(IV) that will be effective in the treatment of a disease in a patient will depend, in part, on the nature of the condition and can be determined by standard clinical techniques known in the art. In addition, in vitro or in vivo assays may be employed to help identify optimal dosage ranges. A therapeutically effective amount of a MHF prodrug of Formulae (I)-(IV) to be administered may also depend on, among other factors, the subject being treated, the weight of the subject, the severity of the disease, the manner of administration, and the judgment of the prescribing physician.

For systemic administration, a therapeutically effective dose may be estimated initially from in vitro assays. For example, a dose may be formulated in animal models to achieve a beneficial circulating composition concentration range. Initial doses may also be estimated from in vivo data, e.g., animal models, using techniques that are known in the art. Such information may be used to more accurately determine useful doses in humans. One having ordinary skill in the art may optimize administration to humans based on animal data.

A dose may be administered in a single dosage form or in multiple dosage forms. When multiple dosage forms are used the amount of compound contained within each dosage form may be the same or different. The amount of a MHF prodrug of Formulae (I)-(IV) contained in a dose may depend on the route of administration and whether the disease in a patient is effectively treated by acute, chronic, or a combination of acute and chronic administration.

In certain embodiments an administered dose is less than a toxic dose. Toxicity of the compositions described herein may be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. In certain embodiments, a MHF prodrug may exhibit a high therapeutic index. The data obtained from these cell culture assays and animal studies may be used in formulating a dosage range that is not toxic for use in humans. A dose of a MHF prodrug provided by the present disclosure may be within a range of circulating concentrations in for example the blood, plasma, or central nervous system, that include the effective dose and that exhibits little or no toxicity. A dose may vary within this range depending upon the dosage form employed and the route of administration utilized. In certain embodiments, an escalating dose may be administered.

Combination Therapy

Methods provided by the present disclosure further comprise administering one or more pharmaceutically active compounds in addition to a MHF prodrug of Formulae (I)-(IV). Such compounds may be provided to treat the same disease or a different disease than the disease being treated with the MHF prodrug of Formulae (I)-(IV).

In certain embodiments, a MHF prodrug of Formulae (I)-(IV) may be used in combination with at least one other therapeutic agent. In certain embodiments, a MHF prodrug of Formulae (I)-(IV) may be administered to a patient together with another compound for treating diseases and conditions involving immunological, autoimmune, and/or inflammatory processes including: psoriasis; asthma, chronic obstructive pulmonary diseases, and arthritis; cardiac insufficiency including left ventricular insufficiency, myocardial infarction and angina pectoris; mitochondrial and neurodegenerative diseases such as Parkinson's disease, Alzheimer's disease, Huntington's disease, retinopathia pigmentosa and mitochondrial encephalomyopathy; transplantation rejection; autoimmune diseases including multiple sclerosis (MS); ischemia and reperfusion injury (AGE-induced genome damage; and others. In certain embodiments, a MHF prodrug of Formulae (I)-(IV) may be administered to a patient together with another compound for treating psoriasis, multiple sclerosis, an inflammatory bowel disease, asthma, chronic obstructive pulmonary disease, and arthritis.

A MHF prodrug of Formulae (I)-(IV) and the at least one other therapeutic agent may act additively or, and in certain embodiments, synergistically. The at least one additional therapeutic agent may be included in the same dosage form as a MHF prodrug of Formulae (I)-(IV) or may be provided in a separate dosage form. Methods provided by the present disclosure can further include, in addition to administering a MHF prodrug of Formulae (I)-(IV), administering one or more therapeutic agents effective for treating the same or different disease than the disease being treated by a MHF prodrug of Formulae (I)-(IV). Methods provided by the present disclosure include administration of a MHF prodrug of Formulae (I)-(IV) and one or more other therapeutic agents provided that the combined administration does not inhibit the therapeutic efficacy of the MHF prodrug and/or does not typically produce significant and/or substantial adverse combination effects.

In certain embodiments, dosage forms comprising a MHF prodrug of Formulae (I)-(IV) may be administered concurrently with the administration of another therapeutic agent, which may be part of the same dosage form as, or in a different dosage form than that comprising a MHF prodrug of Formulae (I)-(IV). A MHF prodrug of Formulae (I)-(IV) may be administered prior or subsequent to administration of another therapeutic agent. In certain embodiments of combination therapy, the combination therapy may comprise alternating between administering a MHF prodrug of Formulae (I)-(IV) and a composition comprising another therapeutic agent, e.g., to minimize adverse drug effects associated with a particular drug. When a MHF prodrug of Formulae (I)-(IV) is administered concurrently with another therapeutic agent that potentially may produce an adverse drug effect including, but not limited to, toxicity, the other therapeutic agent may advantageously be administered at a dose that falls below the threshold at which the adverse drug reaction is elicited.

In certain embodiments, dosage forms comprising a MHF prodrug of Formulae (I)-(IV) may be administered with one or more substances to enhance, modulate and/or control release, bioavailability, therapeutic efficacy, therapeutic potency, stability, and the like of a MHF prodrug of Formulae (I)-(IV). For example, to enhance the therapeutic efficacy of a MHF prodrug ligand of Formulae (I)-(IV), the MHF prodrug of Formulae (I)-(IV) may be co-administered with or a dosage form comprising a MHF prodrug of Formulae (I)-(IV) may comprise one or more active agents to increase the absorption or diffusion of a MHF prodrug of Formulae (I)-(IV) from the gastrointestinal tract to the systemic circulation, or to inhibit degradation of the MHF prodrug of Formulae (I)-(IV) in the blood of a patient. In certain embodiments, a MHF prodrug of Formulae (I)-(IV) may be co-administered with an active agent having pharmacological effects that enhance the therapeutic efficacy of a MHF prodrug of Formulae (I)-(IV).

In certain embodiments, a MHF prodrug of Formulae (I)-(IV) or a pharmaceutical composition thereof may be administered to a patient for treating psoriasis in combination with a therapy or another therapeutic agent known or believed to be effective in treating psoriasis. Drugs useful for treating psoriasis include steroids such as flurandrenolide, fluocinonide, alclometasone, amcinonide, desonide, halcinonide, triamcinolone, clobetasol, clocortolone, mometasone, desoximetasone, and halobetasol; anti-rheumatics such as etanercept, infliximab, and adalimumab; immunosuppressive agents such as cyclosporine, alefacept, and efalizumab; psoralens such as methoxsalen; and other such as calcipotriene, methotrexate, hydrocortisone/pramoxine, acitretin, betamethasone/calcipotriene, tazarotene, benzocaine/pyrilamine/zinc oxide, and ustekinumab.

In certain embodiments, a MHF prodrug of Formulae (I)-(IV) or a pharmaceutical composition thereof may be administered to a patient for treating inflammatory arthritis such as rheumatoid arthritis, juvenile rheumatoid arthritis, psoriatic arthritis, and ankylosing spondylitis in combination with a therapy or another therapeutic agent known or believed to be effective in treating inflammatory arthritis such as rheumatoid arthritis, juvenile rheumatoid arthritis, psoriatic arthritis, and ankylosing spondylitis.

Drugs useful for treating rheumatoid arthritis include non-steroidal anti-inflammatory agents such as ibuprofen, ketoprofen, salicylate, diclofenac, nabumetone, naproxen, meloxicam, sulindac, flurbiprofen, indomethacin, tolmetin, piroxicam, fenoprofen, oxaprozin, and etodolac; antiheumatics such as entanercept, adalimumab, infliximab, hydroxychloroquine, leflunomide, azathioprine, penicillamine, methotrexate, anakinra, auranofin, rituximab, aurothioglucose, tocilizumab, and golimumab; cox-2 inhibitors such as celecoxib and vadecoxib; corticosteroids such as triamcinolone; glucocorticoids such as methylprednisolone and prednisone; and others such as sulfasalazine.

Drugs useful for treating juvenile rheumatoid arthritis include adalimumab, abatacept, and infliximab.

Drugs useful for treating psoriatic arthritis include etanercept, adalimumab, triamcinolone, cortisone, infliximab, and golimumab.

Drugs useful for treating ankylosing spondylitis include adalimumab, celecoxib, diclofenac, etanercept, golimumab, indomethacin infliximab, naptoxen, olsalazine, salicylates, sulfindac, and triamcinolone.

In certain embodiments, a MHF prodrug of Formulae (I)-(IV) or a pharmaceutical composition thereof may be administered to a patient for treating psoriatic arthritis in combination with a therapy or another therapeutic agent known or believed to be effective in treating psioriatic arthritis. Drugs useful for treating psioriatic arthritis include etanercept, adalimumab, triamcinolone, cortisone, infliximab, and golimumab.

In certain embodiments, a MHF prodrug of Formulae (I)-(IV) or a pharmaceutical composition thereof may be administered to a patient for treating autoimmune diseases such as lupus in combination with a therapy or another therapeutic agent known or believed to be effective in treating autoimmune diseases such as lupus. Drugs useful for treating lupus include hydroxychlooquine, triamcinolone, salicylate, azathioprine, and abetimus.

In certain embodiments, a MHF prodrug of Formulae (I)-(IV) or a pharmaceutical composition thereof may be administered to a patient for treating multiple sclerosis in combination with a therapy or another therapeutic agent known or believed to be effective in treating multiple sclerosis. Drugs useful for treating multiple sclerosis include interferon β-1a, interferon β-1b, glatiramer, modafinil, azathioprine, predisolone, mycophenolate mofetil, mitoxantrone, and natalizumab. Other examples of drugs useful for treating MS include Examples of drugs useful for treating MS include corticosteroids such as methylprednisolone; IFN-β such as IFN-β1a and IFN-β1b; glatiramer acetate; monoclonal antibodies that bind to the very late antigen-4 (VLA-4) integrin such as natalizumab; immunomodulatory agents such as FTY 720 sphinogosie-1 phosphate modulator and COX-2 inhibitors such as BW755c, piroxicam, and phenidone; and neuroprotective treatments including inhibitors of glutamate excitotoxicity and iNOS, free-radical scavengers, and cationic channel blockers; memantine; AMPA antagonists such as topiramate; and glycine-site NMDA antagonists.

In certain embodiments, a MHF prodrug of Formulae (I)-(IV) or a pharmaceutical composition thereof may be administered to a patient for treating inflammatory bowel disease in combination with a therapy or another therapeutic agent known or believed to be effective in treating inflammatory bowel disease. Drugs useful for treating inflammatory bowel disease include cromolyn and mercaptopurine; and more particularly for treating Crohn's disease include certolizumab, budesonide, azathioprine, sulfasalazine, metronidazole, adalimumab, mercaptopurine, infliximab, mesalamine, and natalizumab; and for treating ulcerative colitis include balsalazide, infliximab, azathioprine, mesalamine, and cyclosporine.

In certain embodiments, MHF prodrugs provided by the present disclosure and pharmaceutical compositions thereof may be administered to a patient for treating asthma in combination with a therapy or another therapeutic agent known or believed to be effective in treating asthma, or in certain embodiments, a disease, disorder, or condition associated with asthma. Examples of drugs useful in treating asthma include albuterol, aminophylline, beclomethasone, bitolterol, budesonide, cromolyn, ephedrine, epinephrine, flunisolide, fluticasone, formoterol, hydrocortisone, isoproterenol, levalbuterol, methylprednisolone, prednisolone, prednisone, pirbuterol, metaproterenol, racepinephrine, omalizumab, oxytriphylline, mometusone, montelukast, nedocromil, oxtriphylline, pirbuterol, salmeterol, terbutaline, theophylline, triamcinolone, zafirlukast, and zileuton.

In certain embodiments, MHF prodrugs provided by the present disclosure and pharmaceutical compositions thereof may be administered to a patient for treating chronic obstructive pulmonary disease in combination with a therapy or another therapeutic agent known or believed to be effective in treating chronic obstructive pulmonary disease, or in certain embodiments, a disease, disorder, or condition associated with chronic obstructive pulmonary disease. Examples of drugs useful for treating chronic obstructive pulmonary disease include albuterol, arformoterol, azithromycin, bitolterol, epinephrine, fluticasone, formoterol, ipratropium, isoproterenol, levabuterol, metaproterenol, pirbuterol, racepinephrine, salmeterol, and tiotropium. Useful drugs for treating chronic obstructive pulmonary disease further include bronchodialators such as β2 agonists such as salbutamol, bambuterol, clenbuterol, fenoterol, and formoterol; M3 antimuscarinics such as ipratropium; leukotriene antagonists such as montelukast, pranlukast, and zafirlukast; cromones such as cromoglicate and nedocromil; xanthines such as theophylline; corticosteroids such as beclomethasone, mometasone, and fluticasone; and TNF antagonists such as infliximab, adalimumab, and etanercept. Other treatments for chronic obstructive pulmonary disease include oxygen therapy, and pulmonary rehabilitation.

In certain embodiments, prodrugs provided by the present disclosure and pharmaceutical compositions thereof may be administered to a patient for treating angiogenesis in combination with a therapy or another therapeutic agent known or believed to be effective in treating angiogenesis. Useful drugs for treating angiogenesis include angiostatin, endostatin, vitaxin, bevacizumab, thalidomide, batimastat, marimastat, carboxyamidotraizole, TNP-470, CM101, IFN-α, IL-12, platelet factor-4, suramin, SU5416, thrombospondin, VEGFR, angiostatic steroids, cartilage-derived angiogenesis inhibitory factor, matrix metalloproteinase inhibitors, 2-methoxyestradiol, tecogalan, thrombospondin, prolactin, $β_vβ_3$ inhibitors, and linomide.

In certain embodiments, prodrugs provided by the present disclosure and pharmaceutical compositions thereof may be administered to a patient for treating transplant rejection in combination with a therapy or another therapeutic agent known or believed to be effective in treating transplant rejection. Useful drugs for treating transplant rejection include calcineurin inhibitors such as cyclosporine and tacrolimus, mTOR inhibitors such as sirolimus and everolimus, anti-proliferatives such as azathioprine and mycophenolic acid; corticosteroids such as monoclonal anti-IL2Rα receptor antibodies including basiliximab and daclizumab; and polyclonal anti-T-cell antibodies including anti-thymocyte globulin and anti-lymphocyte globulin.

In certain embodiments, prodrugs provided by the present disclosure and pharmaceutical compositions thereof may be administered to a patient for treating transplantation rejection in combination with a therapy or another therapeutic agent known or believed to be effective in treating transplantation rejection. Examples of drugs useful in transplantation rejection include corticosteroids such as dexamethasone, prednisolone, and prednisone; globulins such as antilymphocyte globulin and antithymocyte globulin; macrolide immunosuppressants such as sirolimus, tacrolimus, and everolimus; mitotic inhibitors such as azathiprine, cylophosphamide, and methotrexate; monoclonal antibodies such as basiliximab, daclizumab, infliximab, muromonoab; fungal metabolites such as cyclosporine; and others such as glatiramer and mycophenolate.

In certain embodiments, prodrugs provided by the present disclosure and pharmaceutical compositions thereof may be administered to a patient for treating cardiac insufficiency in combination with a therapy or another therapeutic agent known or believed to be effective in treating cardiac insufficiency. Useful drugs for treating cardiac insufficiency include antitensin-modulating agents, diuretics such as furosemide, bumetanie, hydrochlorothiazide, chlorthalidone, chlorthiazide, spironolactone, eplerenone: beta blockers such as bisoprolol, carvedilol, and metroprolol; positive inotropes such as digoxin, milrinone, and dobutamine; alternative vasodilators such as isosorbide dinitrate/hydralazine; aldosterone receptor antagonists; recombinant neuroendocrine hormones such as nesiritide; and vasopressin receptor antagonists such as tolvaptan and conivaptan.

In certain embodiments, prodrugs provided by the present disclosure and pharmaceutical compositions thereof may be administered to a patient for treating a mitochondrial disease such as a neurodegenerative disorder in combination with a therapy or another therapeutic agent known or believed to be effective in treating a mitochondrial disease such as a neurodegenerative disorder. In certain embodiments, a neurodegenerative disorder is chosen from Alzheimer's disease, Parkinson's disease, Huntington's disease, and amyotrophic lateral sclerosis.

Therapeutic agents useful for treating Parkinson's disease include dopamine precursors such levodopa, dopamine agonists such as bromocriptine, pergolide, pramipexole, and ropinirole, MAO-B inhibitors such as selegiline, anticholinergic drugs such as benztropine, trihexyphenidyl, tricyclic antidepressants such as amitriptyline, amoxapine, clomipramine, desipramine, doxepin, imipramine, maprotiline, nortriptyline, protriptyline, amantadine, and trimipramine, some antihistamines such as diphenhydramine; antiviral drugs such as amantadine; and beta blockers such as propranolol.

Useful drugs for treating Alzheimer's disease include rosiglitazone, roloxifene, vitamin E, donepezil, tacrine, rivastigmine, galantamine, and memantine.

Useful drugs for treating symptoms of Huntington's disease include antipsychotics such as haloperidol, chlorpromazine and olanzapine to control hallucinations, delusions and violent outbursts; antidepressants such as fluoxetine, sertraline, and nortryiptyline to control depression and obsessive-compulsive behavior; tranquilizers such as benzodiazepines, paroxetine, venflaxin and beta-blockers to control anxiety and chorea; mood stabilizers such as lithium, valproate, and carbamzepine to control mania and bipolar disorder; and botulinum toxin to control dystonia and jaw clenching. Useful drugs for treating symptoms of Huntington's disease further include selective serotonin reuptake inhibitors (SSRI) such as fluoxetine, paroxetine, sertraline, escitalopram, citalopram, fluvosamine; norepinephrine and serotonin reuptake inhibitors (NSRI) such as venlafaxine and duloxetine, benzodiazepines such as clonazepam, alprazolam, diazepam, and lorazepam, tricyclic antidepressants such as amitriptyline, nortriptyline, and imipramine; and atypical antidepressants such as busipirone, bupriopion, and mirtazepine for treating the symptoms of anxiety and depression; atomoxetine, dextroamphetamine, and modafinil for treating apathy symptoms; amantadine, memantine, and tetrabenazine for treating chorea symptoms; citalopram, atomoxetine, memantine, rivastigmine, and donepezil for treating cognitive symptoms; lorazepam and trazedone for treating insomnia; valproate, carbamazepine and lamotrigine for treating symptoms of irritability; SSRI antidepressants such as fluoxetine, paroxetine, sertaline, and fluvoxamine, NSRI antidpressants such as venlafaxine, and others such as mirtazepine, clomipramine, lomotrigine, gabapentin, valproate, carbamazepine, olanzapine, rispiridone, and quetiapine for treating symptoms of obsessive-compulsive disorder; haloperidol, quetiapine, clozapine, risperidone, olanzapine, ziprasidone, and aripiprazole for treating psychosis; and pramipexole, levodopa and amantadine for treating rigidity.

Useful drugs for treating ALS include riluzole. Other drugs of potential use in treating ALS include memantine, tamoxifen, thalidomide, ceftriaxone, sodium phenyl butyrate, celecoxib, glatiramer acetate, busipirone, creatine, minocycline, coenzyme Q10, oxandrolone, IGF-1, topiramate, xaliproden, and indinavir. Drugs such as baclofen and diazepam can be useful in treating spasticity associated with ALS.

In certain embodiments, a MHF prodrug of Formulae (I)-(IV) or a pharmaceutical composition thereof may be administered to a patient in combination with a therapy or another therapeutic agent known or believed to be effective in inhibiting TNF function.

Examples of drugs known to inhibit TNF function include infliximab, adalimumab, etanercept, certolizumab, goliimumab, pentoxifylline, quanylhydrozone, thalidomide, flavonoids such as narigenin, resveratol and quecetin, alkaloids such as lycorine, terpenes such as acanthoic acid, fatty acids such as 13-HOA, and retinoids such as retinoic acid.

EXAMPLES

The following examples describe in detail the synthesis of MHF prodrugs of Formulae (I)-(IV), properties of MHF prodrugs of Formulae (I)-(IV), and uses of MHF prodrugs of Formulae (I)-(IV). It will be apparent to those skilled in the art that many modifications, both to materials and methods, may be practiced without departing from the scope of the disclosure.

General Experimental Protocols

All reagents and solvents that were purchased from commercial suppliers were used without further purification or manipulation procedures.

Proton NMR (400 MHz) and carbon NMR spectra (125 MHz) were recorded on a Varian AS 400 NMR spectrometer equipped with an autosampler and data processing software. $CDCl_3$ (99.8% D), DMSO-$d^6$ (99.9% D), or MeOH-$d^4$ (99.8+% D), and acetonitrile-$d^3$ were used as solvents unless otherwise noted. The $CHCl_3$, DMSO-$d^5$, or MeOH-$d^3$ solvent signals were used for calibration of the individual spectra. Analytical thin layer chromatography (TLC) was performed using a Whatman, Schleicher & Schuell TLC and MK6F silica gel plates (2.5×7.5 cm, 250 μm layer thickness). Melting points were recorded in glass capillaries using a Stanford Research Systems (SRS) Optimelt Automated Melting Point System, S/N 78047. Analytical LC/MS was performed on a Waters 2790 separation module equipped with a Waters Micromass QZ mass spectrometer, a Waters 996 photodiode detector, and a Merck Chromolith UM2072-027 or Phenomenex Luna C-18 analytical column Mass-guided preparative HPLC purification of final compounds was performed using an instrument equipped with a Waters 600 controller, ZMD Micromass spectrometer, a Waters 2996 photodiode array detector, and a Waters 2700 Sample Manager. Acetonitrile/water gradients containing 0.05% formic acid were used as eluents in both analytical and preparative HPLC experiments. Compound isolation from aqueous solvent mixtures, e.g., acetonitrile/water/0.05% formic acid, was accomplished by primary lyophilization (freeze drying) of the frozen solutions under reduced pressure at room temperature using manifold freeze dryers such as a Heto Drywinner DW 6-85-1, a Heto FD4, or a VIRTIS Freezemobile 25 ES equipped with high vacuum pumps. When the isolated compound had ionizable functional groups such as an amino group or a carboxylic acid, lyophilization was performed in the presence of a slight excess of one molar (1 M) hydrochloric acid to yield the purified compounds as the corresponding hydrochloride salts (HCl-salts) or the corresponding protonated free carboxylic acids. When the isolated compound had ionizable functional groups such as a carboxylic acid, lyophilization was performed in the presence of equimolar amounts of sodium hydrogen carbonate ($NaHCO_3$) to yield the purified compounds as the corresponding sodium salts (Na-salts). Optionally, the isolated materials were further purified by flush silica gel column chromatography, optionally employing Biotage pre-packed silica gel cartridges. Suitable organic solvents such as ethyl acetate (EtOAc), hexane (H×n), n-heptane (Hptn), or mixtures and/or gradients thereof were used as eluents to yield the target compounds as colorless, viscous oils or solids after evaporation of the solvents. Chemical names were generated with the Chemistry 4-D Draw Pro Version 7.01c (Draw Chemical Structures Intelligently© 1993-2002) from ChemInnovation Software, Inc., San Diego, USA).

Non-commercially available appropriately functionalized or substituted 2-haloacetamides, 2-halo acetic acid derivatives, 2-hydroxy acetamides, 2-hydroxy acetic acid derivatives, acyloxyalkyl halides, or alkoxy- or aryloxycarbonyloxyalkyl halides were synthesized from commercially available starting materials, and by adapting methods well known in the art.

General Synthetic Procedures

General Procedure A: Nucleophilic Substitution of 1-Haloacetamides or 1-Halo Acetic Acid Derivatives with Monomethyl Fumarate:

(2E)-3-(Methoxycarbonyl)prop-2-enoic acid (methyl hydrogen fumarate, MHF), (2E)-3-(tert-butoxycarbonyl) prop-2-enoic acid (tert-butyl hydrogen fumarate), or fumaric acid (FA) (1.0 equivalents) is dissolved in 5-10 mL/3.0 mmol of an inert solvent such as N-methylpyrrolidone (NMP), N,N-dimethylformamide (DMF), N,N-dimethylacetamide (DMA, DMAc), acetonitrile (MeCN), dimethylsulfoxide (DMSO), tetrahydrofuran (THF), toluene, or mixtures thereof. To the solution, 0.8 to 1.2 equivalents of an appropriate inorganic base such as cesium hydrogen carbonate ($CsHCO_3$), cesium carbonate ($Cs_2CO_3$), or potassium carbonate ($K_2CO_3$) is added. Alternatively, 0.8 bis 1.2 equivalents of a silver salt such silver(I) oxide ($Ag_2O$) or silver(I) carbonate ($Ag_2CO_3$); an organic secondary or tertiary base such as dicyclohexylamine (DCHA), triethylamine (TEA), diisopropylethylamine (DIEA), tetrabutylammonium hydroxide (TBAOH), amidine; or a guanidine-based base such as 1,5-diazabicyclo[4.3.0]non-5-ene (DBN), 1,8-diazabicyclo[5.4.0]undec-7-ene (DBU), or 1,1,3,3-tetramethylguanidine (TMG), can be employed. The corresponding alkali, silver, di-, tri- and tetraalkylammonium, amidine, or guanide salt of monoalkyl fumarate can also be preformed. The solution is stirred for 10-60 min at room temperature followed by addition of 0.8-1.2 equivalents of an appropriately functionalized 1-haloacetamide, 1-halo acetic acid derivative, acyloxyalkyl halide, or alky- or aryloxycarbonyloxyalkyl halide. The reaction mixture is stirred overnight at a temperature between 40 to 100° C. After cooling to room temperature, insolubles can optionally be filtered off and the reaction mixture diluted with one molar (1.0 M) hydrochloric acid (HCl) and an appropriate organic solvent such as methyl tert-butyl ether (MTBE), diethyl ether (Et$_2$O), ethylacetate (EtOAc), or mixtures thereof. After phase separation, the aqueous phase is extracted several times with the same solvent. The combined organic extracts are washed with water, brine, and dried over anhydrous magnesium sulfate (MgSO$_4$). After filtration, the organic solvents are removed under reduced pressure using a rotary evaporator. If required, the crude reaction products are further purified by well known purification techniques such as silica gel flash column chromatography (i.e., Biotage), mass-guided reversed-phase preparative HPLC/lyophilization, precipitation, or crystallization.

General Procedure B1: Activation of Carboxylic Acid Derivatives with Dehydration Agents for Aminolysis or Alcoholysis (2E)-3-(Methoxycarbonyl)prop-2-enoic acid (methyl hydrogen fumarate, MHF), 2-[(2E)-3-(methoxycarbonyl)prop-2-enoyloxy]acetic acid (23) or 2-[(2E)-3-(methoxycarbonyl)prop-2-enoyloxy]propanoic acid (24), (1.0 equivalents) are reacted at temperature from ca. 0° C. (ice bath) to room temperature with 1.0-1.5 equivalents of a carbodiimide dehydration agent such as 1-ethyl-3-(3-dimethylaminopropyl)carbodiimide (EDAC, EDC), N,N'-diisopropylcarbodiimide (DIC), N,N'-dicyclohexylcarbodiimide (DCC) in an inert solvent such as dichloromethane (DCM), N,N-dimethylformamide (DMF), N-methylpyrrolidone (NMP), or N,N-dimethylacetamide (DMA, DMAc) (ca. 3 mL/mmol). 1.0-1.5 Equivalents of an appropriately functionalized amine or 2-hydroxy acetamide dissolved in the same solvent and, optionally, in the presence of a catalytic or stoichiometric amount of 4-(N,N-dimethylaminopyridine (DMAP) is added at a temperature from ca. 0° C. to room temperature. When the amine is a salt form, an equimolar amount of an organic tertiary base, such as triethylamine (TEA), or diisopropylethylamine (DIEA) may be added to free the amine base prior to the coupling step. The reaction mixture is stirred for 4 to 12 hours at room temperature. Optionally the organic solvents are removed under reduced pressure using a rotary evaporator and the residue diluted with an appropriate extraction solvent such as diethyl ether (Et$_2$O), methyl tert-butyl ether (MTBE), ethyl acetate (EtOAc), or others. The procedures described in Procedure A for product isolation and purification may be employed.

General Procedure B2: Activation of Carboxylic Acid Derivatives with Chlorination Agents and Aminolysis 2-[(2E)-3-(Methoxycarbonyl)prop-2-enoyloxy]acetic acid (23) or 2-[(2E)-3-(methoxycarbonyl)prop-2-enoyloxy]propanoic acid (24) (1.0 equivalents) are reacted with oxalyl chloride (1.0-1.5 equivalents) in anhydrous dichloromethane (DCM), ca. 3 mL/mmol, at a temperature of ca. 0° C. (ice bath) in the presence of a catalytic amount of N,N-dimethylformamide (DMF) for 1 to 3 hours. The solvents are removed under reduced pressure using a rotary evaporator and the crude material is dissolved in anhydrous dichloromethane (DCM), ca. 3 mL/mmol 1.0-1.5 Equivalents of an appropriately functionalized nucleophile (primary or secondary amine, or alcohol) in anhydrous dichloromethane (DCM), ca. 3 mL/mmol, are added dropwise at ca. 0° C. (ice bath), optionally in the presence of a catalytic amount of 4-(N,N-dimethylamino)pyridine (DMAP). When the amine component is a salt form, an equimolar amount of a base, such as triethyamine (TEA), diisopropylethylamine (DIEA), or others, are added to free the amine base prior to the coupling step. The reaction is stirred overnight with warming to room temperature, the solvents optionally removed under reduced pressure using a rotary evaporator, and then diluted with an appropriate extraction solvent such as diethyl ether (Et$_2$O), methyl tert-butyl ether (MTBE), ethyl acetate (EtOAc), or others. The procedures described in Procedure A for product isolation and purification may be employed.

Example 1

(N,N-Diethylcarbamoyl)methyl methyl (2E)but-2-ene-1,4-dioate (1)

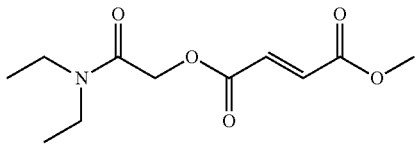 [SMILES: CCN(CC)C(=O)COC(=O)/C=C/C(=O)OC]

Following general procedure A, methyl hydrogen fumarate (MHF) (0.39 g, 3.00 mmol) dissolved in NMP was reacted at ca. 55° C. with 2-chloro-N,N-diethylacetamide (0.44 g, 3.00 mmol) in the presence of CsHCO$_3$ (0.69 g, 3.60 mmol) to afford 0.37 g (51% yield) of the title compound (1) after purification by silica gel column chromatography (Biotage) using a mixture of ethyl acetate (EtOAc) and hexanes (1:1) as eluent. M.p.: 53-56° C. $^1$H NMR (CDCl$_3$, 400 MHz): δ 6.99-6.90 (m, 2H), 4.83 (s, 2H), 3.80 (s, 3H), 3.39 (q, J=7.2 Hz, 2H), 3.26 (q, J=7.2 Hz, 2H), 1.24 (t, J=7.2 Hz, 3H), 1.14 (t, J=7.2 Hz, 3H). MS (ESI): m/z 244.13 (M+H)$^+$.

Example 2

Methyl [N-benzylcarbamoyl]methyl (2E)but-2-ene-1,4-dioate (2)

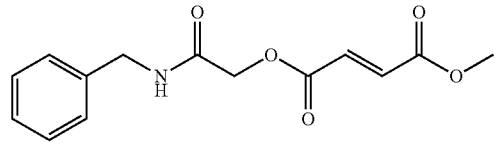 [SMILES: COC(=O)/C=C/C(=O)OCC(=O)NCc1ccccc1]

Following general procedure A, methyl hydrogen fumarate (MHF) (0.50 g, 3.85 mmol) dissolved in NMP was reacted at ca. 55° C. with N-benzyl chloroacetamide (0.84 g, 4.61 mmol) in the presence of CsHCO$_3$ (0.89 g, 4.61 mmol) to afford 0.56 g (53% yield) of the title compound (2) as a white solid after purification by mass-guided preparative HPLC and lyophilization. $^1$H NMR (CDCl$_3$, 400 MHz): δ 7.36-7.26 (m, 5H), 6.94-6.88 (m, 2H), 6.19 (br s, 1H), 4.73 (s, 2H), 4.51 (d, J=5.6 Hz, 2H), 3.81 (s, 3H). MS (ESI): m/z 278.04 (M+H)$^+$.

Example 3

Methyl 2-morpholin-4-yl-2-oxoethyl (2E)but-2-ene-1,4-dioate (3)

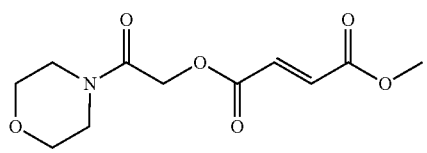 [SMILES: COC(=O)/C=C/C(=O)OCC(=O)N1CCOCC1]

Following general procedure A, methyl hydrogen fumarate (MHF) (0.50 g, 3.84 mmol) dissolved in NMP was reacted at ca. 55° C. with 4-(chloroacetyl) morpholine (0.75 g, 4.61 mmol) in the presence of CsHCO$_3$ (0.89 g, 4.61 mmol) to afford 0.34 g (35% yield) of the title compound (3) as a white solid after purification by mass-guided preparative HPLC and lyophilization. M.p.: 124 to 126° C.; $^1$H NMR (CDCl$_3$, 400 MHz): δ 6.97-6.91 (m, 2H), 4.84 (s, 2H), 3.82 (s, 3H), 3.72-3.70 (m, 4H), 3.64-3.62 (m, 2H), 3.46-3.41 (m, 2H). MS (ESI): m/z 258.04 (M+H)$^+$.

Example 4

(N-Butylcarbamoyl)methyl methyl (2E)but-2-ene-1,4-dioate (4)

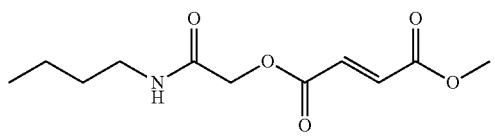 [SMILES: CCCCNC(=O)COC(=O)/C=C/C(=O)OC]

Following general procedure A, methyl hydrogen fumarate (MHF) (0.50 g, 3.84 mmol) dissolved in NMP was reacted at ca. 55° C. with N-butyl chloroacetamide (0.69 g, 4.61 mmol) in the presence of CsHCO$_3$ (0.89 g, 4.61 mmol) to afford 0.19 g (21% yield) of the title compound (4) as a white solid after purification by mass-guided preparative HPLC and lyophilization. $^1$H NMR (CDCl$_3$, 400 MHz): δ 6.98-6.92 (m, 2H), 6.09 (br s, 1H), 4.68 (s, 2H), 3.82 (s, 3H), 3.34-3.29 (q, 2H, J=6.4 Hz), 1.54-1.48 (m, 2H), 1.38-1.32 (m, 2H), 0.956-0.920 (t, J=7.6 Hz, 3H). MS (ESI): m/z 244.04 (M+H)$^+$.

Example 5

[N-(2-Methoxyethyl)carbamoyl]methyl methyl (2E)but-2-ene-1,4-dioate (5)

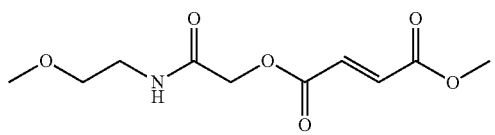

Following general procedure A, methyl hydrogen fumarate (MHF) (0.50 g, 3.84 mmol) dissolved in NMP was reacted at ca. 55° C. with N-(2-methoxyethyl)chloroacetamide (0.69 g, 4.60 mmol) in the presence of CsHCO$_3$ (0.89 g, 4.61 mmol) to afford 0.07 g (8% yield) of the title compound (5) as a white solid after purification by mass-guided preparative HPLC and lyophilization. $^1$H NMR (CDCl$_3$, 400 MHz): δ 6.94-6.92 (m, 2H), 6.46 (br s, 1H), 4.68 (s, 2H), 3.83 (s, 3H), 3.52-3.46 (m, 4H), 3.36 (s, 3H). MS (ESI): m/z 245.98 (M+H)$^+$.

Example 6

2-{2-[(2E)-3-(Methoxycarbonyl)prop-2-enoyloxy]acetylamino}acetic acid (6)

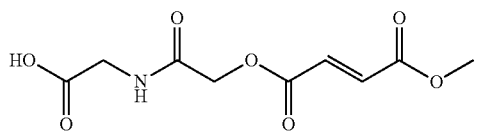 [SMILES: COC(=O)/C=C/C(=O)OCC(=O)NCC(=O)O]

Following general procedure A, methyl hydrogen fumarate (MHF) (0.68 g, 5.26 mmol) dissolved in NMP was reacted at ca. 55° C. with tert-butyl 2-(2-chloroacetylamino)acetate (0.91 g, 4.38 mmol) in the presence of CsHCO$_3$ (1.19 g, 6.13 mmol) of the tert-butyl-protected intermediate and then purified by silica gel column chromatography (Biotage) using a mixture of ethyl acetate (EtOAc) and hexanes (1:2 to 2:3 to 1:1) as eluent. The purified product was treated with 50% trifluoroacetic acid (TFA) in dichloromethane (DCM). Removal of solvents afforded 0.13 g (12% yield) of the title compound (6). $^1$H NMR (CD$_3$OD, 400 MHz): δ 6.96-6.93 (m, 2H), 4.74 (s, 2H), 3.98-3.95 (m, 2H), 3.81 (s, 3H). MS (ESI): m/z 246.00 (M+H)$^+$, 244.02 (M–H)$^-$.

Example 7

4-{2-[(2E)-3-(Methoxycarbonyl)prop-2-enoyloxy]acetylamino}butanoic acid (7)

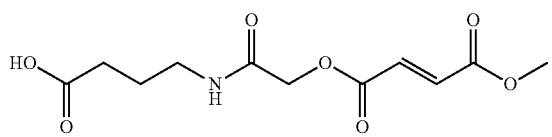 [SMILES: COC(=O)/C=C/C(=O)OCC(=O)NCCCC(=O)O]

Following general procedure A, methyl hydrogen fumarate (MHF) (0.56 g, 4.33 mmol) dissolved in NMP was reacted at ca. 55° C. with tert-butyl 4-(2-chloroacetylamino) butanoate (0.85 g, 3.61 mmol) in the presence of CsHCO$_3$ (0.98 g, 5.05 mmol) of the tert-butyl-protected intermediate and then purified by silica gel column chromatography (Biotage) using a mixture of ethyl acetate (EtOAc) and hexanes (1:1) as eluent. The purified product was treated with 50% trifluoroacetic acid (TFA) in dichloromethane (DCM). Removal of solvents afforded 0.45 g (46% yield) of the title compound (7). $^1$H NMR (CD$_3$OD, 400 MHz): δ 6.94-6.91 (m, 2H), 4.65 (s, 2H), 3.81 (s, 3H), 3.28 (t, J=6.8 Hz, 2H), 2.33 (t, J=7.2 Hz, 2H), 1.81 (p, J=7.1 Hz, 2H). MS (ESI): m/z 274.03 (M+H)$^+$ 272.06 (M–H)$^-$.

Example 8

Methyl(N-(1,3,4-thiadiazol-2-yl)carbamoyl)methyl (2E)but-2ene-1,4-dioate (8)

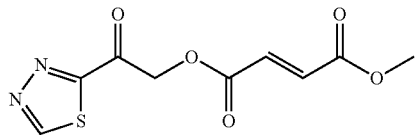 [SMILES: COC(=O)/C=C/C(=O)OCC(=O)c1nncs1]

Following general procedure A, methyl hydrogen fumarate (MHF) (0.50 g, 3.84 mmol) dissolved in NMP was reacted at ca. 55° C. with 2-chloro-N-1,3,4-thiadiazol-2-ylacetamide (0.81 g, 4.61 mmol) in the presence of CsHCO$_3$ (0.89 g, 4.61 mmol). The crude material precipitated out and was washed several times with dichloromethane (DCM) for further purification to afford 0.12 g (12% yield) of the title compound (8) as a white solid. $^1$H NMR (CD$_3$OD, 400 MHz): δ 9.06 (s, 1H), 6.95-6.91 (m, 2H), 4.99 (s, 2H), 3.82 (s, 3H). MS (ESI): m/z 272.07 (M+H)$^+$.

Example 9

N,N-Dimethylcarbamoyl)methyl methyl (2E)but-2-ene-1,4-dioate (9)

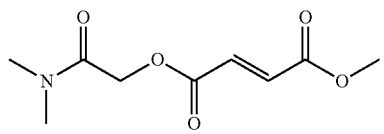

Following general procedure A, methyl hydrogen fumarate (MHF) (0.50 g, 3.84 mmol) dissolved in NMP was reacted at ca. 55° C. with N,N-dimethyl chloroacetamide (0.56 g, 4.61 mmol) in the presence of CsHCO$_3$ (0.89 g, 4.61 mmol). The crude material was precipitated out from a mixture of ethyl acetate (EtOAc) and hexanes (Hxn) (1:1) to provide a white solid. This solid was further dissolved in dichloromethane (DCM) and the organic layer washed with water. After removal of the solvents 0.55 g (67% yield) of the title compound (9) was obtained as a white solid. $^1$H NMR (CDCl$_3$, 400 MHz): δ 6.98-6.90 (m, 2H), 4.84 (s, 2H), 3.80 (s, 3H), 2.99-2.97 (2s, 6H). MS (ESI): m/z 216 (M+H)$^+$.

Example 10

(N-Methoxy-N-methylcarbamoyl)methyl methyl (2E) but-2-ene-1,4-dioate (10)

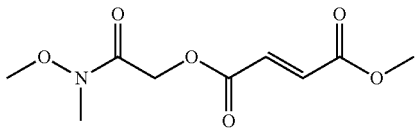

Following general procedure A, methyl hydrogen fumarate (MHF) (0.50 g, 3.84 mmol) dissolved in NMP was reacted at ca. 55° C. with N-methyl, N-hydroxymethyl chloroacetamide (0.63 g, 4.61 mmol) in the presence of CsHCO$_3$ (0.89 g, 4.61 mmol). The crude material precipitated out from a concentrated ethyl acetate (EtOAc) solution. The solid was filtered off and dried in vacuum to provide 0.54 g (61% yield) of the title compound (10) as a white solid. $^1$H NMR (CD$_3$OD, 400 MHz): δ 6.92-6.89 (m, 2H), 5.01 (s, 2H), 3.80 (s, 3H), 3.78 (s, 3H), 3.20 (s, 3H). MS (ESI): m/z 232.06 (M+H)$^+$.

Example 11 bis-(2-Methoxyethylamino)carbamoyl]methyl methyl (2E)but-2-ene-1,4-dioate (11)

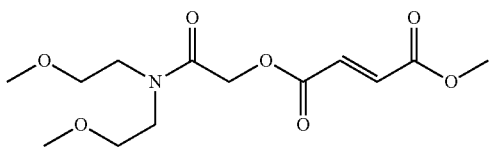

Following general procedure A, methyl hydrogen fumarate (MHF) (0.50 g, 3.84 mmol) dissolved in NMP was reacted at ca. 55° C. with bis-(2-methoxyethyl)-chloroacetamide (0.96 g, 4.61 mmol) in the presence of CsHCO$_3$ (0.89 g, 4.61 mmol) to afford 0.53 g (46% yield) of the title compound (11) as a white solid after purification by mass-guided preparative HPLC and lyophilization. M.p.: 79-82° C.; $^1$H NMR (CDCl$_3$, 400 MHz): δ 6.98-6.88 (m, 2H), 4.98 (s, 2H), 3.8 (s, 3H), 3.57-3.50 (m, 8H), 3.41 (s, 3H), 3.31 (s, 3H). MS (ESI): m/z 304.14 (M+H)$^+$.

Example 12

[N-(Methoxycarbonyl)carbamoyl]methyl methyl (2E)but-gene-1,4-dioate (12)

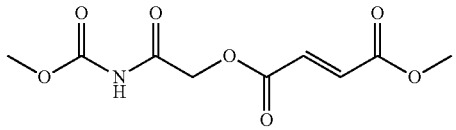

Following general procedure A, methyl hydrogen fumarate (MHF) (0.50 g, 3.84 mmol) dissolved in NMP was reacted at ca. 55° C. with methyl-N-(2-chloroacetyl)carbamate (0.69 g, 4.61 mmol) in the presence of CsHCO$_3$ (0.89 g, 4.61 mmol). The crude material precipitated out from a diethyl ether (Et$_2$O) solution. The solid was filtered off, washed several times with dichloromethane (DCM), and dried in vacuum to provide 0.19 g (21% yield) of the title compound (12) as a white solid. $^1$H NMR (CDCl$_3$, 400 MHz): δ 6.99-6.91 (m, 2H), 5.23 (s, 2H), 3.81 (s, 6H). MS (ESI): m/z 246.09 (M+H)$^+$, 268.00 (M+Na$^+$)$^+$.

Example 13

[N-(2-{2-[(2E)-3-(Methoxycarbonyl)prop-2-enoyloxy]acetylamino}ethyl)carbamoyl]methyl methyl (2E)but-2ene-1,4-dioate (13)

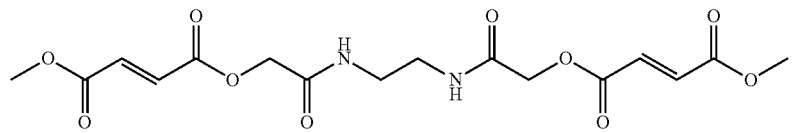

Following general procedure A, methyl hydrogen fumarate (MHF) (0.73 g, 5.61 mmol) dissolved in NMP was reacted at ca. 55° C. with N-(2-[(2-chloroacetyl]aminoethyl)-2-chloro-actamide (0.50 g, 2.34 mmol) in the presence of CsHCO₃ (1.08 g, 5.61 mmol). The crude material precipitated out from a concentrated diethyl ether (Et₂O) solution. The solid was filtered off, washed several times with dichloromethane (DCM), and dried in vacuum to provide 0.90 g (96% yield) of the title compound (13) as a white solid. ¹H NMR (400 MHz, DMSO-d⁶): δ 8.23 (br s, 2H), 6.96-6.92 (m, 4H), 4.58 (s, 4H), 3.79 (s, 6H), 3.16 (m, 4H). MS (ESI): m/z 401.05 (M+H)⁺.

Example 14

Methyl 2-oxo-2-piperazinylethyl (2E)but-2-ene-1,4-dioate Hydrochloride (14)

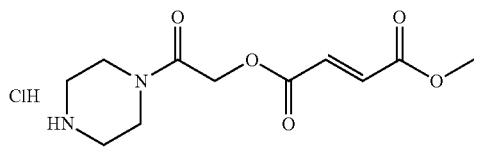 [SMILES: Cl ; COC(=O)/C=C/C(=O)OCC(=O)N1CCNCC1]

Following general procedure A, methyl hydrogen fumarate (MHF) (1.00 g, 7.68 mmol) dissolved in NMP was reacted at ca. 55° C. with 1-(tert-butyloxycarbonyl)-4-chloroacetyl piperazine (2.42 g, 9.22 mmol) in the presence of CsHCO₃ (1.78 g, 9.22 mmol). After work-up and removal of the solvent, the crude material was obtained as a white solid. The solid was reacted at room temperature with 15 mL of a 4 molar (4 M) solution of hydrogen chloride (HCl) in 1,4-dioxane. After removal of the solvents, the solid hydrochloride salt was further purified by mass-guided preparative HPLC to provide 0.93 g (41% yield) of the title compound (14) as a white solid after lyophilization of the solvents in the presence of an excess of aqueous 1 normal (1 N) hydrochloric acid. ¹H NMR (D₂O, 400 MHz): δ 6.93-6.86 (m, 2H), 4.92 (s, 2H), 3.70-3.63 (m, 7H), 3.23 (t, J=5.2 Hz, 2H), 3.17 (t, J=6 Hz, 2H). MS (ESI): m/z 257.13 (M+H)⁺.

Example 15

Methyl 2-(4-benzylpiperazinyl)-2-oxoethyl (2E) but-2-ene-1,4-dioate (15)

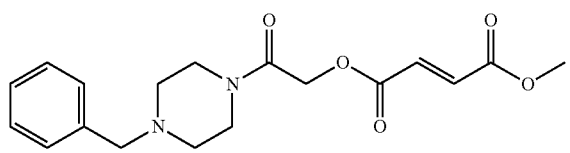 [SMILES: COC(=O)/C=C/C(=O)OCC(=O)N1CCN(Cc2ccccc2)CC1]

Methyl 2-oxo-2-piperazinylethyl (2E)but-2-ene-1,4-dioate hydrochloride (14) (0.50 g, 1.71 mmol) was reacted at ca. 0° C. with benzyl bromide (BnBr) (0.243 mL, 0.35 g, 2.05 mmol) and diisopropylethylamine (DIEA) (1.00 mL, 0.74 g, 5.76 mmol) in dichloromethane (DCM) followed by warming to room temperature. After aqueous work-up, the crude product was purified by mass-guided preparative HPLC to afford 0.18 g (27% yield) of the title compound (15) as a white solid. ¹H NMR (CDCl₃, 400 MHz): δ 7.08-7.01 (m, 5H), 6.72-6.71 (m, 2H), 4.60 (s, 2H), 3.58-3.57 (s, 3H), 3.23-3.19 (br S, 2H), 3.30 (s, 2H), 3.1.19-3.11 (br S, 2H), 2.23 (br S, 4H); MS (ESI) m/z 347.13 (M+H)⁺.

Example 16

2-(4-Acetylpiperazinyl)-2oxoethyl methyl (2E)but-2ene-1,4-dioate (16)

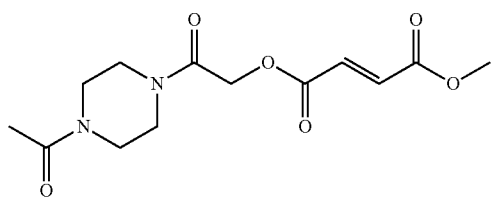 [SMILES: COC(=O)/C=C/C(=O)OCC(=O)N1CCN(C(C)=O)CC1]

Methyl 2-oxo-2-piperazinylethyl (2E)but-2-ene-1,4-dioate hydrochloride (14) (0.20 g, 0.68 mmol) was reacted with acetyl chloride (AcCl) (0.60 mL, 0.66 g, 0.84 mmol) and diisopropylethylamine (0.70 mL, 0.52 g, 4.0 mmol) in dichloromethane (DCM). Following aqueous work-up, the crude product was purified by silica gel flash chromatography to afford 0.12 g (54% yield) of the title compound (16) as a white solid. ¹H NMR (CDCl₃, 400 MHz): δ 6.98-6.93 (m, 2H), 4.86 (s, 2H), 3.83 (s, 3H), 3.66 3.63 (m, 4H), 3.50-3.40 (m, 4H), 2.14 (s, 3H). MS (ESI): m/z 299.12 (M+H)⁺.

Example 17

Methyl 2-oxo-2-(2-oxo(1,3-oxazolidin-3-yl)ethyl (2E) but-2ene-1,4-dioate (17)

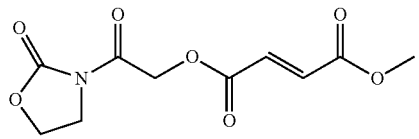 [SMILES: COC(=O)/C=C/C(=O)OCC(=O)N1CCOC1=O]

Following general procedure A, methyl hydrogen fumarate (MHF) (0.50 g, 3.84 mmol) dissolved in NMP was reacted at ca. 55° C. with 3-(chloroacetyl)-1,3-oxazolidine-2-one (0.75 g, 4.61 mmol) in the presence of CsHCO₃ (0.89 g, 4.61 mmol) to yield 0.30 g (30% yield) of the title compound (17) as a white solid after purification by mass-guided preparative HPLC and lyophilization. ¹H NMR (CDCl₃, 400 MHz): δ 6.97-6.92 (m, 2H), 5.32 (s, 2H), 4.53 (t, J=8 Hz, 2H), 4.05 (t, J=8.0 Hz, 2H), 3.82 (s, 3H). MS (ESI); m/z 258.20 (M+H)⁺.

Example 18

{N-[2-(Dimethylamino)ethyl]carbamoyl}methyl methyl (2E)but-gene-1,4 dioate (18)

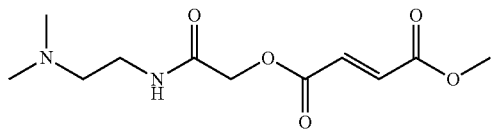

Following general procedure A, methyl hydrogen fumarate (MHF) (0.50 g, 3.84 mmol) dissolved in NMP was reacted at ca. 55° C. with N,N-dimethylethylenediamino chloroacetamide (0.75 g, 4.61 mmol) in the presence of CsHCO₃ (0.89 g, 4.61 mmol) to provide 0.02 g (2% yield) of the title compound

(18) as a white solid after purification by mass-guided preparative HPLC and lyophilization. $^1$H NMR (D$_2$O, 400 MHz): δ 8.27, (s, 1H), 6.87-6.78, (m, 2H), 4.63 (s, 2H), 3.68 (s, 3H), 3.51 (t, J=6.2 Hz, 2H), 3.17 (t, J=6.0 Hz, 2H), 2.76 (s, 6H). MS (ESI); m/z 259.14 (M+H)$^+$.

Example 19

Methyl {N-[(propylamino)carbonyl]carbamoyl}methyl (2E)but-gene-1,4-dioate (19)

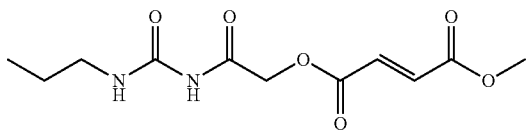 [SMILES: CCCNC(=O)NC(=O)COC(=O)/C=C/C(=O)OC]

Following general procedure A, methyl hydrogen fumarate (MHF) (0.50 g, 3.84 mmol) dissolved in NMP was reacted at ca. 55° C. with 1-(2-chloroacetyl)-3-propyl urea (0.82 g, 4.60 mmol) in the presence of CsHCO$_3$ (0.89 g, 4.61 mmol) to provide 0.02 g (2% yield) of the title compound (19) as a white solid. Addition of methanol (MeOH) afforded 0.49 g (48% yield) of white solid. $^1$H NMR (CDCl$_3$, 400 MHz): δ 6.90-6.99 (m, 2H), 4.77 (s, 2H), 3.82 (s, 3H), 3.25-3.24 (q, 2H, J=5.6 Hz), 1.57-1.55 (q, 2HJ=7.2 Hz), 0.95-0.91 (t, 3H, J=7.6 Hz). MS (ESI): m/z 273.08 (M+H)$^+$.

Example 20

2-{(2S)-2-[(tert-Butyl)oxycarbonyl]pyrrolidinyl}-2-oxoethyl methyl (2E)but-2ene-1,4-dioate (20)

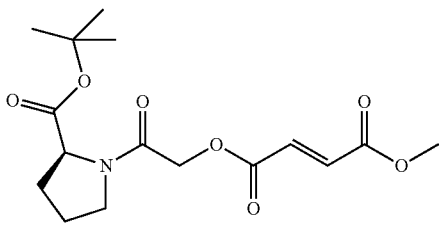 [SMILES: COC(=O)/C=C/C(=O)OCC(=O)N1CCC[C@H]1C(=O)OC(C)(C)C]

Following general procedure A, methyl hydrogen fumarate (MHF) (0.50 g, 3.84 mmol) dissolved in NMP was reacted at ca. 55° C. with tert-butyl (2S)-1-(2-chloroacetyl)pyrrolidine-2-carboxylate (0.82 g, 4.60 mmol) in the presence of CsHCO$_3$ (0.89 g, 4.61 mmol) to provide 0.44 g (34% yield) of the title compound (20) as a white solid after purification by mass-guided preparative HPLC and lyophilization. $^1$H NMR (CDCl$_3$, 400 MHz, all rotamers): δ 6.97-6.90 (m, 2H), 4.91-4.55 (m, 2H), 4.44-4.29 (m, 1H), 3.80 (s, 3H), 3.61-3.58 (m, 2H), 2.23-2.03 (br m, 4H), 1.54-1.46 (s, 9H). MS (ESI): m/z 342.16 (M+H)$^+$, 364.09 (M+Na$^+$)$^+$.

Example 21

(N-{[tert-Butyl)oxycarbonyl]methyl}-N-methylcarbamoyl)methyl methyl (2E)but-2ene-1,4-dioate (21)

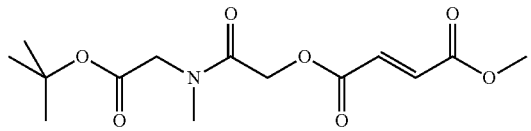 [SMILES: COC(=O)/C=C/C(=O)OCC(=O)N(C)CC(=O)OC(C)(C)C]

Following general procedure A, methyl hydrogen fumarate (MHF) (0.50 g, 3.84 mmol) dissolved in NMP was reacted at ca. 55° C. with tert-butyl 2-(2-chloro-N-methylacetylamino)acetate (1.02 g, 4.60 mmol) in the presence of CsHCO$_3$ (0.89 g, 4.61 mmol) to provide 0.24 g (21% yield) of the title compound (21) as a white solid after purification by silica gel flash chromatography (Biotage). $^1$H NMR (CDCl$_3$, 400 MHz, all rotamers): δ 7.00-6.93 (m, 2H), 4.90-4.79 (2s, 2H), 4.03-3.89 (2s, 2H), 3.80 (s, 3H), 3.04-2.99 (2S, 3H), 1.45 (S, 9H). MS (ESI): m/z 316.13 (M+H)$^+$.

Example 22

{N-(Ethoxycarbonyl)methyl]-N-methylcarbamoyl}methyl methyl (2E)but-2-ene-1,4-dioate (22)

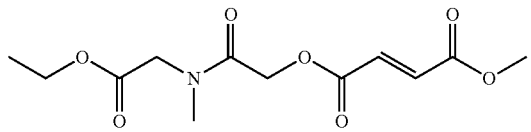 [SMILES: CCOC(=O)CN(C)C(=O)COC(=O)/C=C/C(=O)OC]

Following general procedure A, methyl hydrogen fumarate (MHF) (0.50 g, 3.84 mmol) dissolved in NMP was reacted at ca. 55° C. with ethyl 2-(2-chloro-N-methylacetylamino)acetate (0.89 g, 4.60 mmol) in the presence of CsHCO$_3$ (0.89 g, 4.61 mmol) to provide 0.30 g (27% yield) of the title compound (22) as a white solid after purification by silica gel flash chromatography (Biotage). $^1$H NMR (CDCl$_3$, 400 MHz, all rotamers): δ 7.00-6.93 (m, 2H), 4.90-4.79 (2s, 2H), 4.03-3.89 (2s, 2H), 3.80 (s, 3H), 3.04-2.99 (2s, 3H), 1.45 (s, 9H). MS (ESI): m/z 316.13 (M+H)$^+$.

Example 23

2-[(2E)-3-(Methoxycarbonyl)prop-2-enoyloxy]acetic acid (23)

Following general procedure A, methyl hydrogen fumarate (MHF) (6.91 g, 53.12 mmol) dissolved in NMP was reacted at ca. 55° C. with tert-butyl 2-chloroacetic acid (9.48 mL, 10.0 g, 66.4 mmol) in the presence of CsHCO$_3$ (15.41 g, 79.68 mmol) to provide 13.11 g (81% yield) of the intermediate ester as a white solid after precipitation from a concentrated diethyl ether (Et$_2$O) solution. The material was of sufficient purity to be used in the next step. $^1$H NMR (CDCl$_3$, 400 MHz): δ 6.95-6.92 (m, 2H), 4.61 (s, 2H), 3.81 (s, 3H), 1.47 (s, 9H). The material was dissolved in 50 mL of 50 vol.-% of trifluoroacetic acid (TFA) in dichloromethane (DCM) and reacted overnight at room temperature. After removal of the solvents, the crude material was precipitated from a mixture of acetone and hexanes (1:3) to afford 12.3 g (92% yield) of the title compound (23) as a white solid. $^1$H NMR (CDCl$_3$, 400 MHz): δ 7.02-6.90 (m, 2H), 4.79 (s, 2H), 3.82 (s, 3H). MS (ESI): m/z 189.07 (M+H)$^+$. MS (ESI): m/z 189.07 (M+H)$^+$.

Example 24 rac-2-[(2E)-3-(Methoxycarbonyl)prop-2-enoyloxy]propanoic acid (24)

Following general procedure A, methyl hydrogen fumarate (MHF) (4.68 g, 36.0 mmol) dissolved in NMP was reacted at ca. 55° C. with rac-tert-butyl 2-bromo propionic acid (4.98 mL, 6.27 g, 30.0 mmol) in the presence of CsHCO$_3$ (6.40 g, 33.0 mmol) to yield the intermediate ester. The material was of sufficient purity to be used in the next step. $^1$H NMR (CDCl$_3$, 400 MHz): δ 6.93-6.88 (m, 2H), 5.02 (q, J=7.2 Hz, 2H), 3.79 (s, 3H), 1.49 (d, J=7.2 Hz, 3H), 1.44 (s, 9H). The material was dissolved in 25 mL of 50 vol.-% of trifluoroacetic acid (TFA) in dichloromethane (DCM) and reacted overnight at room temperature. After removal of the solvents, the title compound (24) was obtained as a white solid that was of sufficient purity to be used in subsequent steps. $^1$H NMR (CDCl$_3$, 400 MHz): δ 6.97-6.92 (m, 2H), 5.22 (q, J=7.2 Hz, 2H), 3.82 (s, 3H), 1.60 (d, J=7.2 Hz, 3H).

Example 25

Methyl 2-(4-methylpiperazinyl)-2-oxoethyl (2E)but-2-ene-1,4-dioate (25)

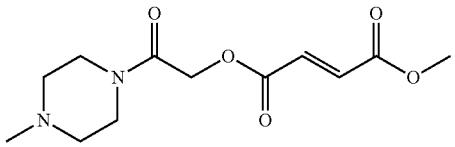

Following general procedure B2, 2-[(2E)-3-(methoxycarbonyl)prop-2-enoyloxy]acetic acid (23) (0.50 g, 2.65 mmol) was activated with N-(3-dimethylaminopropyl)-N'-ethylcarbodiimide hydrochloride (EDAC) (0.60 g, 3.18 mmol) in 10 mL of dichloromethane (DCM) at ca. 0° C. N-Methyl piperazine (0.353 mL, 0.31 g, 3.18 mmol) and 4-(N,N-dimethyl)aminopyridine (DMAP) (0.40 g, 3.18 mmol) were added to the activated carboxylic acid. After work-up and isolation, and purification by mass-guided preparative HPLC afforded 0.09 g (13% yield) of the title compound (25) as a white solid after lyophilization. $^1$H NMR (CDCl$_3$, 400 MHz): δ 6.93-6.78 (m, 2H), 4.77 (s, 2H), 3.73 (s, 3H), 3.56-3.54 (m, 2H), 3.35-3.25 (m, 2H), 2.37-2.33 (m, 4H), 2.31 (s, 3H). MS (ESI): m/z 271.13 (M+H)$^+$.

Example 26

{N,N-bis[2-(Methylethoxyethyl]carbamoyl}methyl methyl (2E)but-2-ene-1,4-dioate (26)

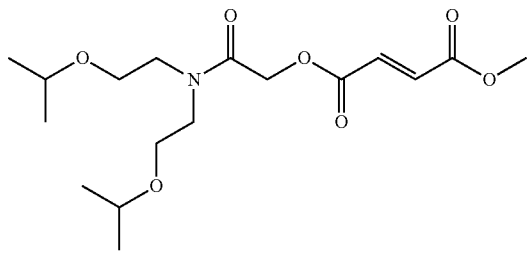 [SMILES: COC(=O)/C=C/C(=O)OCC(=O)N(CCOC(C)C)CCOC(C)C]

Following general procedure B2, 2-[(2E)-3-(methoxycarbonyl)prop-2-enoyloxy]acetic acid (23) (0.50 g, 2.65 mmol) was activated with N-(3-dimethylaminopropyl)-N'-ethylcarbodiimide hydrochloride (EDAC) (0.60 g, 3.18 mmol) in 10 mL of dichloromethane (DCM) at ca. 0° C. bis(2-Isopropoxyethyl)amine (0.60 g, 3.18 mmol) and 4-(N,N-dimethyl)aminopyridine (DMAP) (0.40 g, 3.18 mmol) were added to the activated carboxylic acid. After work-up and isolation, and purification by silica gel flash column chromatography (Biotage) using ethyl acetate (EtOAc) and hexanes (1:1) afforded 0.30 g (32% yield) of the title compound (26) as a white solid following refrigeration. $^1$H NMR (CDCl$_3$, 400 MHz): δ 6.95-6.86 (m, 2H), 4.98 (s, 2H), 3.76 (s, 3H), 3.50-3.47 (m, 10H), 1.10-1.05 (m, 12H). MS (ESI): m/z 360.16 (M+H)$^+$.

Example 27

[N,N-bis(2-Ethoxyethyl)carbamoyl]methyl methyl (2E)but-2-ene-1,4-dioate (27)

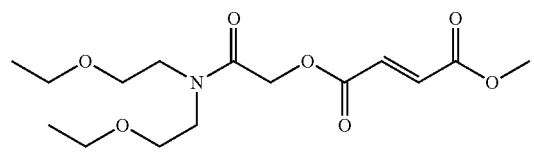 [SMILES: CCOCCN(CCOCC)C(=O)COC(=O)/C=C/C(=O)OC]

Following general procedure B2, 2-[(2E)-3-(methoxycarbonyl)prop-2-enoyloxy]acetic acid (23) (0.80 g, 6.14 mmol) was activated with N-(3-dimethylaminopropyl)-N'-ethylcarbodiimide hydrochloride (EDAC) (1.40 g, 7.37 mmol) in 20 mL of dichloromethane (DCM) at ca. 0° C. bis(2-Ethoxyethyl)amine hydrochloride (1.18 g, 7.37 mmol) (1.18 g, 7.37 mmol) and diisopropylethylamine (DIEA) (1.34 mL, 0.99 g, 7.67 mmol) were added to the activated carboxylic acid. After work-up and isolation, and purification by silica gel flash column chromatography (Biotage) using ethyl acetate (EtOAc) and hexanes (1:1) afforded 0.30 g (15% yield) of the title compound (27) as a white solid. $^1$H NMR (CDCl$_3$, 400 MHz): δ 6.97 (d, J=15.6 Hz, 1H), 6.94 (d, J=1.6 Hz, 1H), 5.01 (s, 2H), 3.80 (s, 3H), 3.56-3.43 (m, 12H), 1.19 (q, J=7.6 Hz, 6H). MS (ESI): m/z 332.20 (M+H)$^+$.

Example 28

Methyl 1-methyl-2-morpholin-4-yl-2-oxoethyl (2E)but-2-ene-1,4-dioate

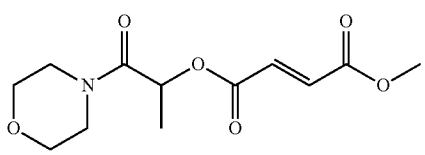 [SMILES: COC(=O)/C=C/C(=O)OC(C)C(=O)N1CCOCC1]

Following general procedure B2, 2-[(2E)-3-(methoxycarbonyl)prop-2-enoyloxy]propanoic acid (24) (0.48 g, 2.40 mmol) was activated with N-(3-dimethylaminopropyl)-N'-ethylcarbodiimide hydrochloride (EDAC) (0.64 g, 3.36 mmol) in 10 mL of dichloromethane (DCM) at ca. 0° C. Morpholine (0.25 mL, 0.25 g, 2.88 mmol) was added to the activated carboxylic acid. After work-up and isolation, and purification by mass-guided preparative HPLC afforded 0.22 g (33% yield) of the title compound (28) as a white solid after lyophilization. M.p.: 70-73° C. $^1$H NMR (CDCl$_3$, 400 MHz): δ 6.95-6.89 (m, 2H), 5.45 (q, J=6.8 Hz, 1H), 3.80 (s, 3H), 3.71-3.68 (m, 4H), 3.58-3.54 (m, 4H), 1.48 (d, J=7.2 Hz, 3H). MS (ESI): m/z 272.13 (M+H)+.

Example 29

[N,N-bis(2-Methoxyethyl)carbamoyl]ethyl methyl (2E)but-2-ene-1,4-dioate (29)

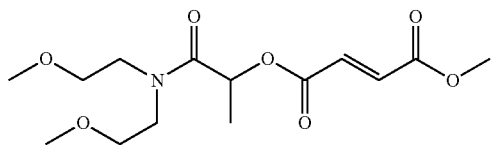

Following general procedure B2, 2-[(2E)-3-(methoxycarbonyl)prop-2-enoyloxy]propanoic acid (24) (0.48 g, 2.40 mmol) was activated with N-(3-dimethylaminopropyl)-N'-ethylcarbodiimide hydrochloride (EDAC) (0.64 g, 3.36 mmol) in 10 mL of dichloromethane (DCM) at ca. 0° C. bis(2-Methoxyethyl)amine (0.42 mL, 0.37 g, 2.88 mmol) was added to the activated carboxylic acid. After work-up and isolation, and purification by mass-guided preparative HPLC afforded 0.29 g (38% yield) of the title compound (29) as a white solid after lyophilization. $^1$H NMR (CDCl$_3$, 400 MHz): δ 6.94-6.88 (m, 2H), 5.52 (q, J=6.8 Hz, 1H), 3.80-3.79 (s, 3H), 3.57-3.49 (m, 8H), 3.33-3.31 (2s, 6H), 1.48 (d, J=6.4 Hz, 3H). MS (ESI): m/z 318.13 (M+H)+.

Example 30

(N,N-Dimethylcarbamoyl)ethyl methyl (2E)but-2-ene-1,4-dioate (30)

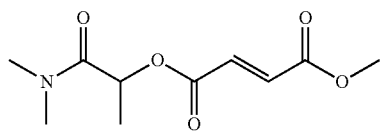

Following general procedure B2, 2-[(2E)-3-(methoxycarbonyl)prop-2-enoyloxy]propanoic acid (24) (0.48 g, 2.40 mmol) was activated with N-(3-dimethylaminopropyl)-N'-ethylcarbodiimide hydrochloride (EDAC) (0.64 g, 3.36 mmol) in 10 mL of dichloromethane (DCM) at ca. 0° C. N,N-Dimethylamine hydrochloride (0.23 g, 2.88 mmol) and diisopropylethylamine (DIEA) (0.63 mL, 0.467 g, 3.61 mmol) were added to the activated carboxylic acid. After work-up and isolation, and purification by mass-guided preparative HPLC afforded 0.25 g (46% yield) of the title compound (30) as a white solid after lyophilization. $^1$H NMR (CDCl$_3$, 400 MHz): δ 6.93-6.86 (m, 2H), 5.46 (q, J=6.8 Hz 1H), 3.79 (s, 3H), 3.06-2.97 (2s, 6H), 1.47 (d, J=6.4 Hz, 3H). MS (ESI): m/z 230.13 (M+H)+.

Example 31

(1S)-1-Methyl-2-morpholin-4-yl-2-oxoethyl methyl (2E)but-2-ene-1,4-dioate (31)

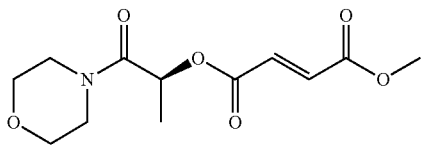 [SMILES: COC(=O)/C=C/C(=O)O[C@@H](C)C(=O)N1CCOCC1]

Following general procedure B2, (2E)-3-(methoxycarbonyl)prop-2-enoic acid (methyl hydrogen fumarate, MHF) (0.50 g, 3.84 mmol) was activated with N-(3-dimethylaminopropyl)-N'-ethylcarbodiimide hydrochloride (EDAC) (0.81 g, 4.20 mmol) in 10 mL of dichloromethane (DCM) at ca. 0° C. (2S)-2-Hydroxy-1-morpholin-4-yl-propan-1-one (0.48 g, 3.07 mmol) and 4-(N,N-dimethyl)aminopyridine (DMAP) (0.40 g, 3.18 mmol) were added to the activated carboxylic acid. After work-up and isolation, and purification by silica gel flash column chromatography (Biotage) using ethyl acetate (EtOAc) and hexanes (ca. 3:2) afforded 0.42 g (51% yield) of the title compound (31) as a white solid. M.p.: 79-82° C.; $^1$H NMR (CD$_3$CN, 400 MHz): δ 6.90-6.81 (m, 2H), 5.44 (q, J=6.8 Hz 1H), 3.78 (s, 3H), 3.65-3.60 (m, 4H), 3.51-3.50 (m, 4H), 1.42 (d, J=6.8 Hz 3H). MS (ESI): m/z 272.05 (M+H)+.

Example 32

(1S)-1-[N,N-bis(2-Methoxyethyl)carbamoyl]ethyl methyl (2E)but-2-ene-1,4-dioate (32)

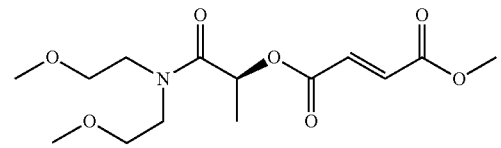

Following general procedure B2, (2E)-3-(methoxycarbonyl)prop-2-enoic acid (methyl hydrogen fumarate, MHF) (0.50 g, 3.84 mmol) was activated with N-(3-dimethylaminopropyl)-N'-ethylcarbodiimide hydrochloride (EDAC) (0.88 g, 4.60 mmol) in 20 mL of dichloromethane (DCM) at ca. 0° C. (2S)-2-Hydroxy-N,N-bis(2-methoxyethyl)propanamide (0.63 g, 3.07 mmol) and 4-(N,N-dimethyl)aminopyridine (DMAP) (0.40 g, 3.18 mmol) were added to the activated carboxylic acid. After work-up and isolation, and purification by silica gel flash column chromatography (Biotage) using ethyl acetate (EtOAc) and hexanes (2:1) afforded 0.16 g (14% yield) of the title compound (32) as a clear oil. $^1$H NMR (CDCl$_3$, 400 MHz): δ 6.93-6.77 (m, 2H), 5.53 (q, J=6.4 Hz, 1H), 3.80 (s, 3H), 3.58-3.50 (m, 8H), 3.47-3.32 (2s, 6H), 1.49 (d, J=6.8 Hz, 3H). MS (ESI): m/z 318.05 (M+H)+.

Example 33

(1S)-1-(N,N-Diethylcarbamoyl)ethyl methyl (2E) but-2-ene-1,4-dioate (33)

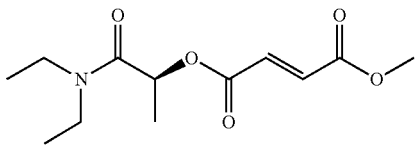 [SMILES: CCN(CC)C(=O)[C@H](C)OC(=O)/C=C/C(=O)OC]

Following general procedure B2, (2E)-3-(methoxycarbonyl)prop-2-enoic acid (methyl hydrogen fumarate, MHF) (0.50 g, 3.84 mmol) was activated with N-(3-dimethylaminopropyl)-N'-ethylcarbodiimide hydrochloride (EDAC) (0.88 g, 4.60 mmol) in 12 mL of dichloromethane (DCM) at ca. 0° C. (2S)—N,N-Diethyl-2-hydroxypropanamide (0.44 g, 3.07 mmol) (0.44 g, 3.07 mmol) and 4-(N,N-dimethyl)aminopyridine (DMAP) (0.40 g, 3.18 mmol) were added to the activated carboxylic acid. After work-up and isolation, and purification by mass-guided preparative HPLC/lyophilization and by silica gel flash column chromatography (Biotage) using ethyl acetate (EtOAc) and hexanes afforded 0.17 g (18% yield) of the title compound (33) as a clear oil. $^1$H NMR (CDCl$_3$, 400 MHz): δ 6.95-6.87 (m, 2H), 5.43 (q, J=6.8 Hz, 1H) 3.80 (s, 3H), 3.50-3.26 (m, 4H), 1.49 (d, J=6.4 Hz, 3H), 1.26 (t, J=6.8, 3H), 1.12 (t, J=7.6 Hz, 3H). MS (ESI): m/z 258.06 (M+H)$^+$.

Example 34

(N-{[(tert-Butyl)oxycarbonyl]methyl}carbamoyl) methyl methyl (2E)but-2-ene-1,4-dioate (34)

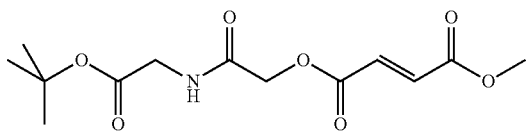 [SMILES: COC(=O)/C=C/C(=O)OCC(=O)NCC(=O)OC(C)(C)C]

Following general procedure B2, 2-[(2E)-3-(methoxycarbonyl)prop-2-enoyloxy]acetic acid (23) (0.50 g, 2.65 mmol) was activated with oxalyl chloride (0.30 mL, 0.40 g, 3.18 mmol) in dichloromethane (DCM) at ca. 0° C. and in the presence of a catalytic amount of N,N-dimethylformamide (DMF). A DCM solution of the freshly prepared crude acid chloride was reacted ca. 0° C. (ice bath) with glycine tert-butyl ester (H-GlyOtBu) (0.53 g, 3.18 mmol) in DCM and in the presence of 4-(N,N-dimethyl)aminopyridine (DMAP) (0.40 g, 3.18 mmol). After aqueous work-up and isolation, and purification by silica gel flash chromatography afforded 0.16 g (20% yield) of the title compound (34) as a semi-solid material. $^1$H NMR (CDCl$_3$, 400 MHz, all rotamers): δ 6.95-6.69 (m, 2H), 6.63 (br. m, 1H), 4.73 (s, 2H), 3.99 (d, J=4.8 Hz, 2H), 3.83 (s, 3H), 1.48 (s, 9H). MS (ESI): m/z 324.05 (M+Na$^+$)$^+$.

Example 35

Methyl (N-methyl-N-{[(methylethyl)oxycarbonyl] methyl}carbamoyl)methyl (2E)but-2-ene-1,4-dioate (35)

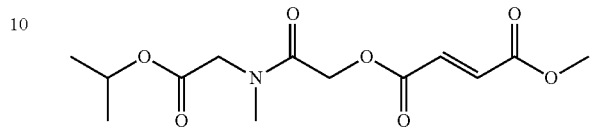

Following general procedure B2, 2-[(2E)-3-(methoxycarbonyl)prop-2-enoyloxy]acetic acid (23) (0.50 g, 2.65 mmol) was activated with oxalyl chloride (0.30 mL, 0.40 g, 3.18 mmol) in dichloromethane (DCM) at ca. 0° C. and in the presence of a catalytic amount of N,N-dimethylformamide (DMF). A DCM solution of the freshly prepared crude acid chloride was reacted ca. 0° C. (ice bath) with sarcosine isopropyl ester (H-Sar-OiPr) (0.41 g, 3.18 mmol) and diisopropylethylamine (DIEA) (0.41 mL, 0.304 g, 2.35 mmol) in DCM and in the presence of 4-(N,N-dimethyl)aminopyridine (DMAP) (0.10 g, 0.82 mmol). After aqueous work-up and isolation, and purification by silica gel flash chromatography afforded 0.214 g (27% yield) of the title compound (35) as a pale-yellow solid. $^1$H NMR (CDCl$_3$, 400 MHz, all rotamers): δ 6.94-6.90 (m, 2H), 5.09-4.99 (m, 1H), 4.89-4.79 (2s, 2H), 4.07-3.95 (2s, 2H), 3.78 (s, 3H), 3.04-2.98 (2s, 3H), 1.27-1.21 (m, 6H). MS (ESI): m/z 302.04 (M+H)$^+$.

Example 36

{N-[(Ethoxycarbonyl)methyl]-N-benzylcarbamoyl}methyl methyl (2E)but-2-ene-1,4-dioate (36)

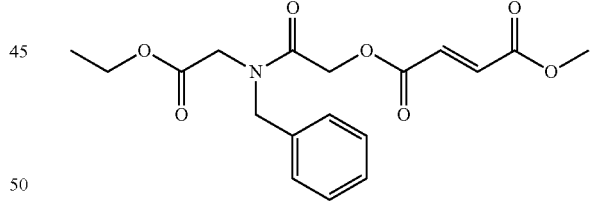

Following general procedure B2, 2-[(2E)-3-(methoxycarbonyl)prop-2-enoyloxy]acetic acid (23) (0.50 g, 2.65 mmol) was activated with oxalyl chloride (0.27 mL, 0.40 g, 3.15 mmol) in dichloromethane (DCM) at ca. 0° C. and in the presence of a catalytic amount of N,N-dimethylformamide (DMF). A DCM solution of the freshly prepared crude acid chloride was reacted ca. 0° C. (ice bath) with N-benzyl glycine ethyl ester (Bn-Gly-OEt) (0.61 g, 3.18 mmol) in DCM and an excess of diisopropylethylamine (DIEA) in the presence of a catalytic amount of 4-(N,N-dimethyl)aminopyridine (DMAP). After aqueous work-up and isolation, and purification by silica gel flash chromatography afforded 0.12 g (13% yield) of the title compound (36) as a white solid. $^1$H NMR (CDCl$_3$, 400 MHz, all rotamers): δ 7.37-7.20 (m, 5H), 6.97-6.86 (m, 2H), 4.94-4.83 (2s, 2H), 4.63-4.55 (2s, 2H), 4.18-4.14 (m, 2H), 4.04-3.88 (2s, 2H), 3.79 (s, 3H), 1.24-1.20 (m, 3H). MS (ESI): m/z 364.15 (M+H)⁺.

Example 37

{N-[(Ethoxycarbonyl)methyl]-N-benzylcarbamoyl}ethyl methyl (2E)but-2-ene-1,4-dioate (37)

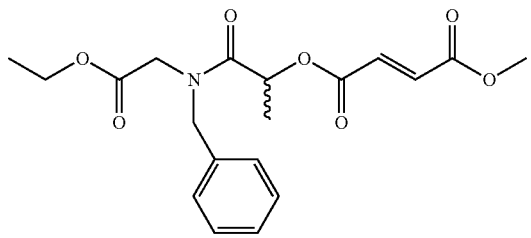 [SMILES: CCOC(=O)CN(Cc1ccccc1)C(=O)C(C)OC(=O)/C=C/C(=O)OC]

Following general procedure B2, 2-[(2E)-3-(methoxycarbonyl)prop-2-enoyloxy]propanoic acid (24) (0.50 g, 2.47 mmol) was activated with oxalyl chloride (0.25 mL, 0.35 g, 2.71 mmol) in dichloromethane (DCM) at ca. 0° C. and in the presence of a catalytic amount of N,N-dimethylformamide (DMF). A DCM solution of the freshly prepared crude acid chloride was reacted ca. 0° C. (ice bath) with N-benzyl glycine ethyl ester (Bn-Gly-OEt) (0.56 g, 2.90 mmol) in DCM and diisopropylethylamine (DIEA) (0.506 mL, 0.376 g, 2.90 mmol) in the presence of a catalytic amount of 4-(N,N-dimethyl)aminopyridine (DMAP). After aqueous work-up and isolation, and purification by silica gel flash chromatography afforded 0.31 g (33% yield) of the title compound (37) as a white solid. ¹H NMR (CDCl₃, 400 MHz, all rotamers): δ 7.37-7.17 (m, 5H), 6.88-6.77 (m, 2H), 5.49 (q, J=6.4 Hz, 0.75H), 5.33 (q, J=6.4 Hz, 0.25H), 4.7-4.27 (m, 3H), 4.16-4.13 (m, 2H), 3.83-3.63 (m, 4H), 1.53 (d, J=6.8 Hz, 3H), 1.21 (t, J=4.0 Hz, 3H). MS (ESI): m/z 378.10 (M+H)⁺.

Example 38

{N-[(Ethoxycarbonyl)methyl]-N-methylcarbamoyl}ethyl methy (2E)but-2-ene-1,4-dioate (38)

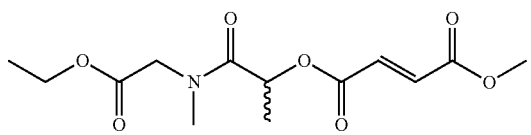 [SMILES: CCOC(=O)CN(C)C(=O)C(C)OC(=O)/C=C/C(=O)OC]

Following general procedure B2, 2-[(2E)-3-(methoxycarbonyl)prop-2-enoyloxy]propanoic acid (24) (0.50 g, 2.47 mmol) was activated with oxalyl chloride (0.25 mL, 0.35 g, 2.71 mmol) in dichloromethane (DCM) at ca. 0° C. and in the presence of a catalytic amount of N,N-dimethylformamide (DMF). A DCM solution of the freshly prepared crude acid chloride was reacted ca. 0° C. (ice bath) with sarcosine ethyl ester (H-Sar-OEt) (0.43 g, 2.90 mmol) and diisopropylethylamine (DIEA) (0.506 mL, 0.376 g, 2.90 mmol) in DCM and in the presence of a catalytic amount of 4-(N,N-dimethyl)aminopyridine (DMAP). After aqueous work-up and isolation, and purification by silica gel flash chromatography afforded 0.30 g (39% yield) of the title compound (38) as a white solid. ¹H NMR (CDCl₃, 400 MHz, all rotamers): δ 6.88-6.81 (m, 2H), 5.47 (q, 0.75H, J=6.8 Hz), 5.32 (q, 0.25H, J=6.8 Hz), 4.40-4.33 (m, 1H), 4.16-4.11 (m, 2H), 3.94-3.75 (m, 4H), 3.10 (s, 2.25H), 2.96 (s, 0.75H), 1.50-1.44 (dd, 3H), 1.26-1.20 (m, 3H). MS (ESI): m/z 302.09 (M+H)⁺.

Example 39

Ethoxycarbonyloxyethyl methyl (2E)but-2-ene-1,4-dioate (39)

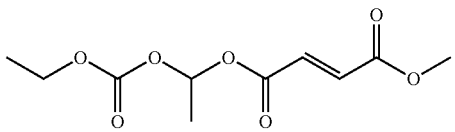 [SMILES: CCOC(=O)OC(C)OC(=O)/C=C/C(=O)OC]

Following general procedure A, methyl hydrogen fumarate (0.39 g, 3.0 mmol) in NMP (8 mL) was reacted with CsHCO₃ (0.69 g, 3.6 mmol) and ethyl (chloroethoxy)formate (0.64 g, 4.2 mmol) to afford 0.63 g (85% yield) of the title compound (39) after isolation and purification. ¹H NMR (CDCl₃, 400 MHz): δ 6.89 (d, J=15.6 Hz, 1H), 6.82 (d, J=15.6 Hz, 1H), 6.84 (q, J=5.6 Hz, 1H), 4.23 (q, J=7.2 Hz, 3H), 3.81 (s, 3H), 1.58 (d, J=5.6 Hz, 3H), 1.32 (t, J=7.2 Hz, 3H). MS (ESI): m/z 247.01 (M+H)⁺.

Example 40

Methyl (methylethoxycarbonyloxy)ethyl (2E)but-2-ene-1,4-dioate (40)

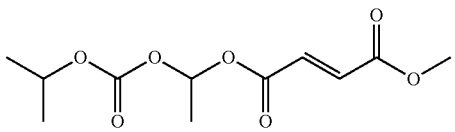 [SMILES: COC(=O)/C=C/C(=O)OC(C)OC(=O)OC(C)C]

Following general procedure A, methyl hydrogen fumarate (0.39 g, 3.0 mmol) in NMP (8 mL) was reacted with CsHCO₃ (0.69 g, 3.6 mmol) and methylethyl (chloroethoxy)formate (0.70 g, 4.2 mmol) to afford 0.71 g (91% yield) of the title compound (40) after isolation and purification. ¹H NMR (CDCl₃, 400 MHz): δ 6.89 (d, J=15.6 Hz, 1H), 6.84 (q, J=5.2 Hz, 1H, superimposed), 6.82 (d, J=15.6 Hz, 1H, superimposed), 4.90 (heptet, J=6.2 Hz, 3H), 3.81 (s, 3H), 1.57 (d, J=5.2 Hz, 3H), 1.32 (d, J=6.2 Hz, 3H), 1.31 (d, J=6.2 Hz, 3H). MS (ESI): m/z 261.02 (M+H)⁺.

Example 41

(Cyclohexyloxycarbonyloxy)ethyl methyl (2E)but-2-ene-1,4-dioate (41)

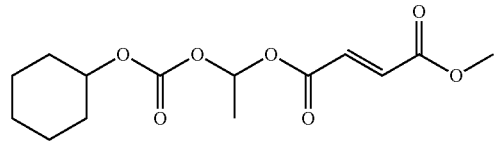 [SMILES: COC(=O)/C=C/C(=O)OC(C)OC(=O)OC1CCCCC1]

Following general procedure A, methyl hydrogen fumarate (0.50 g, 3.85 mmol) was reacted with CsHCO₃ (1.1 g, 5.71 mmol) and chloroethyl cyclohexanecarboxylate (1.03 g, 4.99 mmol) at ca. 55° C. to afford 0.94 g (82% yield) of the title compound (41) after purification by mass-guided preparatory HPLC and lyophilization. $^1$H NMR (CDCl$_3$, 400 MHz): δ 6.91-6.79 (m, 3H), 4.67-4.62 (m, 1H), 3.81 (s, 3H), 1.94-1.91 (m, 2H), 1.77-1.73 (m, 2H), 1.57 (d, J=5.6 Hz, 3H), 1.53-1.46 (m, 3H), 1.39-1.33 (m, 3H). MS (ESI); m/z 301.10 (M+H)$^+$.

Example 42

Methyl (2-methylpropanoyloxy)ethyl (2E)but-2-ene-1,4-dioate (42)

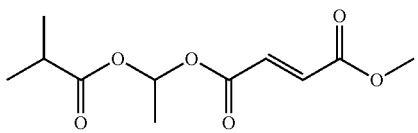 [SMILES: COC(=O)/C=C/C(=O)OC(C)OC(=O)C(C)C]

Following general procedure A, methyl hydrogen fumarate (0.39 g, 3.0 mmol) in NMP (8 mL) was reacted with CsHCO$_3$ (0.69 g, 3.6 mmol) and chloroethyl 2-methylpropanoate (0.63 g, 4.2 mmol) to afford 0.65 g (89% yield) of the title compound (42) after isolation and purification. $^1$H NMR (CDCl$_3$, 400 MHz): δ 6.93 (q, J=5.2 Hz, 1H), 6.88 (d, J=16.0 Hz, 1H), 6.81 (d, J=15.6 Hz, 1H), 3.81 (s, 3H), 2.55 (heptet, J=6.8 Hz, 3H), 1.54 (d, J=5.2 Hz, 3H), 1.18 (d, J=6.8 Hz, 6H). MS (ESI): m/z 245.05 (M+H)$^+$.

Example 43

Methyl phenylcarbonyloxyethyl (2E)but-2-ene-1,4-dioate (43)

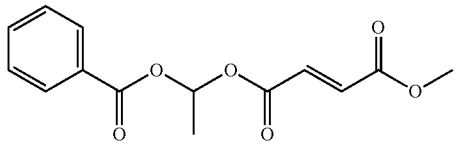 [SMILES: COC(=O)/C=C/C(=O)OC(C)OC(=O)c1ccccc1]

Following general procedure A, methyl hydrogen fumarate (0.42 g, 3.3 mmol) in NMP (6 mL) was reacted with CsHCO$_3$ (0.69 g, 3.6 mmol) and chloroethyl benzoate (0.55 g, 3.0 mmol) to afford 0.2 g (24% yield) of the title compound (43) after purification by silica gel flash column chromatography (Biotage) using a mixture of ethyl acetate (EtOAc) and hexanes (1:8) as eluent. $^1$H NMR (CDCl$_3$, 400 MHz): δ 8.08-8.02 (m, 2H), 7.63-7.56 (m, 1H), 7.49-7.42 (m, 2H), 7.21 (q, J=5.2 Hz, 1H), 6.92 (d, J=16.0 Hz, 1H), 6.85 (d, J=16.0 Hz, 1H), 3.81 (s, 3H), 1.69 (d, J=5.2 Hz, 3H). MS (ESI): m/z 278.99 (M+H)$^+$.

Example 44

Cyclohexylcarbonyloxybutyl methyl (2E)but-2-ene-1,4-dioate (44)

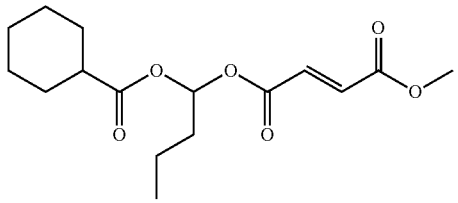 [SMILES: CCCC(OC(=O)/C=C/C(=O)OC)OC(=O)C1CCCCC1]

Following general procedure A, methyl hydrogen fumarate (1.00 g, 7.68 mmol) was reacted with CsHCO$_3$ (2.22 g, 11.52 mmol) and chlorobutyl cyclohexanecarboxylate (2.16 g, 9.98 mmol) at ca. 55° C. to afford 1.2 g (50% yield) of the title compound (44) as a clear oil after purification by mass-guided preparatory. HPLC and lyophilization. $^1$H NMR (CDCl$_3$, 400 MHz): δ 6.90-6.77 (m, 3H), 3.81 (s, 3H), 2.34-2.28 (m, 1H), 1.91-1.88 (m, 2H), 1.82-1.73 (m, 4H), 1.65-1.62 (m, 2H), 1.47-1.39 (m, 4H), 1.29-1.23 (m, 2H), 0.98-0.94 (t, 3H). MS (ESI): m/z 313.09 (M+H)$^+$.

Example 45

[(2E)-3-(Methoxycarbonyl)prop-2-enoyloxy]ethyl methyl (2E)but-2-ene-1,4-dioate (45)

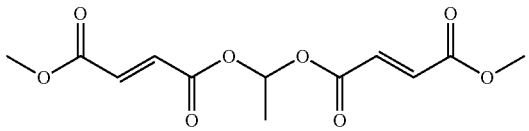

Adopting methods and procedures according to Iyer, et al., *Synth. Commun.* 1995, 25(18), 2739, chloroethyl methyl (2E) but-2-ene-1,4-dioate was prepared from methyl hydrogen fumarate (MHF), acetaldehyde, and anhydrous zinc(II) chloride in anhydrous dichloromethane (DCM). $^1$H NMR (CDCl$_3$, 400 MHz): δ 6.95 (d, J=16.0 Hz, 1H), 6.85 (d, J=16.0 Hz, 1H), 6.60 (q, J=5.2 Hz, 1H), 3.81 (s, 3H), 1.83 (d, J=5.2 Hz, 3H).

Following general procedure A, methyl hydrogen fumarate (0.22 g, 1.7 mmol) in NMP (4 mL) was reacted with CsHCO$_3$ (0.38 g, 1.9 mmol) and chloroethyl methyl (2E)but-2-ene-1,4-dioate (0.27 g, 1.4 mmol) to afford 0.068 g (17% yield) of the title compound (45) after purification by silica gel flash chromatography (Biotage) using a mixture of ethyl acetate (EtOAc) and hexanes (1:3). $^1$H NMR (CDCl$_3$, 400 MHz): δ 7.03 (q, J=5.2 Hz, 1H), 6.90 (d, J=16.0 Hz, 1H), 6.82 (d, J=16.0 Hz, 1H), 3.82 (s, 3H), 1.60 (d, J=5.2 Hz, 3H).

Example 46

Methyl 2-methyl-1-phenylcarbonyloxypropyl (2E) but-2-ene-1,4-dioate (46)

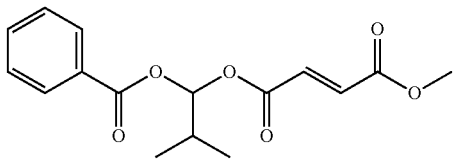 [SMILES: COC(=O)/C=C/C(=O)OC(OC(=O)c1ccccc1)C(C)C]

Following general procedure A, methyl hydrogen fumarate (0.50 g, 3.82 mmol) was reacted with CsHCO$_3$ (5.76 mmol) and chloroisobutyl benzoate (1.1 g, 5.17 mmol) at ca. 55° C. to afford 0.18 g (15% yield) of the title compound (46) after purification by silica gel flash chromatography (Biotage) using a mixture of ethyl acetate (EtOAc) and hexanes (1:7). $^1$H NMR (CDCl$_3$, 400 MHz): δ 8.04-8.01 (m, 2H), 7.58-7.55 (m, 1H), 7.45-7.41 (m, 2H) 6.98 (d, J=4.8 Hz, 1H), 6.90 (d, J=16.0 Hz, 1H), 6.84 (d, J=16.0 Hz, 1H), 3.78 (s, 3H), 2.25-2.21 (m, 1H), 1.10-1.07 (m, 6H); MS (ESI): m/z 307.11 (M+H)⁺.

Example 47

(2E)-3-[(2-Morpholin-4-yl-2-oxoethyl)oxycarbonyl]prop-2-enoic acid (47)

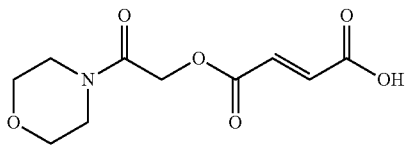 [SMILES: O=C(O)/C=C/C(=O)OCC(=O)N1CCOCC1]

Following general procedure A, fumaric acid (1.00 g, 8.60 mmol) was reacted with chloro acetyl morpholine (1.4 g, 8.6 mmol) and Ag₂O (4.2 g, 9.47 mmol) at ca. 100° C. in N-methylpyrrolidinone. The reaction mixture was cooled to room temperature, filtered over Celite®, and the filter cake was washed with ethylacetate (EtOAc). The combined organic filtrates were subjected to acidic aqueous work-up and the crude material was purified by mass-guided preparative HPLC to give 0.50 g (24% yield) of the title compound (47) as a white solid. ¹H NMR (CD₃CN, 400 MHz): δ 6.85-6.80 (m, 2H), 4.85 (s, 2H), 3.64-3.60 (m, 4H), 3.57-3.54 (t, J=4.8 Hz, 2H), 3.42-3.39 (t, J=5.2 Hz, 2H). MS (ESI): m/z 244.06 (M+H)⁺, 242.07 (M–H)⁻.

Example 48

(2E)-3-{[(N,N-Diethylcarbamoyl)methyl]oxycarbonyl}prop-2-enoic acid (48)

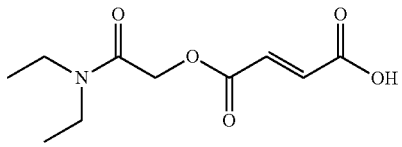 [SMILES: CCN(CC)C(=O)COC(=O)/C=C/C(=O)O]

Following general procedure A, mono tert-butyl fumaric acid (0.70 g, 4.06 mmol) was reacted with N,N-diethyl chloroacetamide (0.55 mL, 0.60 g, 4.06 mmol) and CsHCO₃ (0.93 g, 4.87 mmol) at ca. 55° C. in N-methylpyrrolidinone (NMP). After isolation and purification, the crude material was reacted in 50 vol-% trifluoroacetic acid (TFA) in dichloromethane (DCM). The free acid was purified by mass-guided preparative HPLC to afford 0.051 g (6% yield) of the title compound (48) as a white solid. ¹H NMR (CD₃CN, 400 MHz): δ 6.90-6.82 (m, 2H), 4.88 (s, 2H), 3.40-3.32 (q, J=6.8 Hz, 2H), 3.31-3.27 (q, J=6.8 Hz, 2H), 1.22-1.18 (t, J=7.6 Hz, 3H), 1.11-1.07 (t, J=6.8 Hz, 3H). MS (ESI): m/z=230.03 (M+H)⁺, 228.07 (M–H)⁻.

Example 49

(2E)-3-{[(2-Methylpropanoyloxy)ethyl]oxycarbonyl}prop-2-enoic acid (49)

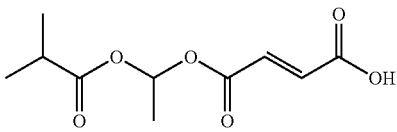 [SMILES: CC(OC(=O)/C=C/C(=O)O)OC(=O)C(C)C]

Following general procedure A, chloroethyl 2-methylpropanoate (0.24 g, 1.58 mmol) was reacted overnight with the pre-formed bis-dicyclohexylamine salt (DCHA) of fumaric acid (FA) (0.50 g, 1.26 mmol) in N-methylpyrrolidinone (NMP) at ca 100° C. The crude material was purified by mass-guided preparative HPLC to afford (0.035 g, 12% yield) of the title compound (49) as a white, waxy, semi-solid. ¹H NMR (CD₃CN, 400 MHz): δ 6.89-6.83 (q, J=5.6 Hz, 1H), 6.82-6.81 (d, J=16.0 Hz, 1H), 6.73-6.69 (d, J=16.0 Hz, 1H), 2.58-2.49 (heptet, J=6.8 Hz, 1H), 1.49-1.47 (d, J=5.6 Hz, 3H), 1.12 (d, J=7.2 Hz, 3H), 1.09 (d, J=6.8 Hz, 6H); MS (ESI): m/z=239.01 (M–H)⁻.

Example 50

(2E)-3-({[(Methylethyl)oxycarbonyloxy]ethyl}oxycarbonyl)prop-2-enoic acid (50)

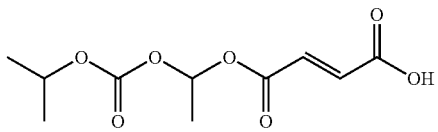 [SMILES: CC(C)OC(=O)OC(C)OC(=O)/C=C/C(=O)O]

Following general procedure A, chloroethyl (methylethoxy)formate (0.25 g, 1.50 mmol) was reacted overnight with the pre-formed bis-dicyclohexylamine salt (DCHA) of fumaric acid (FA) (0.50 g, 1.26 mmol) in N-methylpyrrolidinone (NMP) at ca. 100° C. The crude material was purified by mass-guided preparative HPLC to afford (0.030 g, 10% yield) of the title compound (50) as a white, waxy, semi-solid. ¹H NMR (CD₃CN, 400 MHz): δ 6.86 (q, J=5.6 Hz, 1H), 6.81 (d, J=16.0 Hz, 1H), 6.73 (d, J=16.0 Hz, 1H), 2.57-2.50 (heptet, J=7.2 Hz, 1H), 1.48 (d, J=5.6 Hz, 3H), 1.13 (m, 6H). MS (ESI): m/z=244.99 (M–H)⁻.

Example 51

Alkyloxy- and Aryloxy-Carbonyloxyalkyl Alkyl Hydrogen Fumarates

The following alkyloxy- and aryloxy-carbonyloxyalkyl hydrogen fumarates were prepared using the methods described in Examples 1-50 and adapting general synthetic procedures A, B1, and B2:
(2E)-3-({[N-benzylcarbamoyl]methyl}oxycarbonyl)prop-2-enoic acid;
(2E)-3-[(2-morpholin-4-yl-2-oxoethyl)oxycarbonyl]prop-2-enoic acid;
(2E)-3-{[(N-butylcarbamoyl)methyl]oxycarbonyl}prop-2-enoic acid;

(2E-3-{[N-methoxy-N-methylcarbamoyl)methyl] oxycarbonyl}prop-2-enoic acid;
bis-(2-methoxyethylamino)carbamoyl]methyl prop-2-enoic acid;
N,N-dimethylcarbamoyl)methyl pro-2-enoic acid;
2-[(2E)-3-(methoxycarbonyl)prop-2-enoyloxy]acetic acid;
(2E)-3-({[N-(3-carboxypropyl)carbamoyl] methyl}oxycarbonyl)prop-2-enoic acid;
methyl (N-(1,3,4-thiadiazol-2-yl)carbamoyl)methyl prop-2-enoic acid;
(2E)-3-[(2-{(2S)-2-[tert-butyl)oxycarbonyl]pyrrolidinyl}-2-oxoethyl)oxycarbonyl]prop-2enoic acid;
1-[2-((2E)-3-carboxyprop-2-enoyloxy)acetyl](2S) pyrrolidine-2-carboxylic acid;
(2E)-3-[([N-[(ethoxycarbonyl)methyl]-N-methylcarbamoyl}methyl)oxycarbonyl]prop-2-enoic acid;
(2E)-3-{[(N-{[(tert-butyl)oxycarbonyl]methyl}-N-methylcarbamoyl)methyl]oxycarbonyl}prop-2-enoic acid;
(2E)-3-[(1-methyl-2-morpholin-4-yl-2-oxoethyl)oxycarbonyl]prop-2-enoic acid;
(2E)-3-({[N,N-bis(2-methoxyethyl)carbamoyl] ethyl}oxycarbonyl)prop-2-enoic acid;
(2E)-3-{[(N,N-dimethylcarbamoyl)ethyl] oxycarbonyl}prop-2-enoic acid;
(2E)-3-[({N,N-bis[2-methylethoxy)ethyl] carbamoyl}methyl)oxycarbonyl]prop-2-enoic acid;
(2E)-3-({[N,N-bis(2-ethoxyethyl)carbamoyl] methyl}oxycarbonyl)prop-2-enoic acid;
(2E)-3-{[2-(4-acetylpiperazinyl)-2-oxoethyl] oxycarbonyl}prop-2-enoic acid;
(2E)-3-({2-oxo-2-[4-benzylpiperazinyl]ethyl}oxycarbonyl) prop-2-enoic acid;
(2E)-3-{[(N-{[(tert-butyl)oxycarbonyl]methyl}carbamoyl) methyl]oxycarbonyl}prop-2-enoic acid;
(2E)-3-{[(N-methyl-N-{[(methylethyl)oxycarbonyl] methyl}carbamoyl)methyl]oxycarbonyl}prop-2-enoic acid;
(2E)-3-[({N-[(ethoxycarbonyl)methyl]-N-benzylcarbamoyl}methyl)oxycarbonyl]prop-2-enoic acid;
(2E)-3-[({N-[(ethoxycarbonyl)methyl]-N-benzylcarbamoyl}ethyl)oxycarbonyl]prop-2-enoic acid; and
(2E)-3-[({N-[(ethoxycarbonyl)methyl]-N-methylcarbamoyl}ethyl)oxycarbonyl]prop-2-enoic acid.

Example 52

Methods for Determining Stability of Prodrugs In Vitro

For a prodrug, it can be desirable that the prodrug remains intact (i.e., uncleaved) while in the systemic circulation and be cleaved (i.e., to release the parent drug) in the target tissue. Alternatively, it can be desirable that the prodrug remains intact (i.e., uncleaved) while in the gastrointestinal tract and be cleaved (i.e., to release the parent drug) after being absorbed or taken up from the gastrointestinal lumen, e.g., in either the enterocytes lining the gastrointestinal lumen or in the blood. A useful level of stability can at least in part be determined by the mechanism and pharmacokinetics of the prodrug. In general, prodrugs that are more stable in pancreatin or colonic wash assay and are more labile in rat plasma, human plasma, rat liver S9, and/or human liver S9 preparations can be useful as an orally administered prodrug. In general, prodrugs that are more stable in rat plasma, human plasma, rat liver S9, and/or human liver S9 preparations and which are more labile in cell homogenate preparations, such CaCo2 S9 preparations, can be useful as systemically administered prodrugs and/or can be more effective in delivering a prodrug to a target tissue. In general, prodrugs that are more stable in a range of pH physiological buffers (pH 6.0 to pH 8.5) can be more useful as prodrugs. In general, prodrugs that are more labile in cell homogenate preparations, such CaCo2 S9 preparations, can be intracellularly cleaved to release the parent drug to a target tissue. The results of tests, such as those described in this example, for determining the enzymatic or chemical cleavage of prodrugs in vitro can be used to select prodrugs for in vivo testing.

The stabilities of prodrugs can be evaluated in one or more in vitro systems using a variety of preparations following methods known in the art. For example, methods used to determine the stability of prodrugs in Caco2 S9 homogenate, rat liver S9, rat plasma, porcine pancreatin, rat colonic wash, and pH 8.0 buffer are described herein.

CaCo2 S9 homogenate was prepared using the following procedure. CaCo2 cells were grown in culture for 21 days prior to harvesting. Culture medium was removed from the culture vessel and the monolayer was rinsed twice with 10-15 mL chilled PBS buffer. PBS buffer (7-10 mL) was added to the flask and the cells scraped from the growth surface and transferred to a centrifuge tube. The cells were pelleted by centrifugation at 1500 rpm for 5 min at 4° C. The supernatant was removed and the cell pellet washed with ice cooled PBS and repelleted by centrifugation. The supernatant was removed and the pellet resuspended in cell lysis buffer (0.15M KCl and 10 mM sodium phosphate buffer, pH 7.4). Cells were lysed by sonication at 4° C. using a probe sonicator. The lysed cells were then transferred to vials and centrifuged at 1600 rpm for 10 min at 4° C. to remove intact cells, nuclei, and large cellular debris. The supernatant was removed and transferred to a tube for centrifugation at 8600 rpm for 20 min at 4° C. After centrifugation, the resulting supernatant representing the CaCo2 cell homogenate S9 fraction was carefully removed and aliquoted into vials for storage at −80° C. until the time of use. At the time of use, CaCo2 S9 lysate was diluted to 0.5 mg/mL in 0.1M Tris buffer, pH 7.4.

Rat liver S9 (XenoTech, Lenexa, Kans.; R1000.59, 20 mg/mL) was diluted to 0.5 mg mL in 0.1 M potassium phosphate buffer at pH 7.4 and 1 mM NADPH cofactor.

Rat plasma (Pel-Freez® Biologicals, Rogers, Ark.; 36150) was used as obtained from the supplier.

Porcine pancreatin (Sigma Aldrich, St. Louis, Mo.; P1625-100G) was diled to 10 mg/mL in 0.1M Tris buffer, pH 7.4.

To prepare the rat colonic wash, the colon between the ceacum and rectum was resected from a euthanized rat. Five to 10 mL of PBS pH 7.4 buffer (depending on the weight of the rat) was flushed into the lumen of the large intestine and collected into a 250 mL glass beaker at 0° C. (ice bath). The colonic wash was transferred into 10 mL conical tubes using a 10 mL syringe fitted with a filter. Samples of 0.5 mL colonic wash are stored at −80° C. until the time of use. Colonic was used without dilution.

The enzymatic stability assays for prodrug in CaCo2 S9, rat liver S9, rat plasma, pig pancreatin, and rat colonic was were performed using the following procedure. Ninety (90) μL of lysate is aliquoted to designated tubes on a cluster plates. The lysate was preincubated for 10 min at 37° C. With the exception of the t(0) time point, 10 μL of a 400 μM solution of test compound in 0.1M Tris buffer, pH 7.4 was added to multiple wells representing different incubation times. The samples were incubated at 37° C. At each time point, the reaction was quenched by adding 300 µL of 100% ethanol. The samples were thoroughly mixed, the tubes transferred to a V-bottom plate, and stored at −20° C. For the t(0) time point, the lysate was quenched with 300 µL of ice cold 100% ethanol, thoroughly mixed, 10 µL of 400 µM test compound was added and mixed, and the sample tube transferred to a V-bottom plate and mixed, and stored at −20° C. For analysis, 180 µL from each sample was transferred to a 96 well V-bottom plate and sealed. After all time points were collected, the plate was centrifuged for 10 min at 5600 rpm at 4° C. One-hundred fifty (150) µL from each well was then transferred to a 96 well round bottom plate. Samples were analyzed using LC/MS/MS to determine the concentrations of prodrug and parent drug.

For the pH 8.0 stability studies, 190 µL of 150 mM $NaH_2PO_4$ buffer pH 8.0 was added to each sample tube. Ten (10) µL of 20 mM test compound was added to each tube and mixed. The samples were incubated for 60 min at 37° C. Following incubation, the samples were transferred to room temperature and 800 µL of 50% ACN in water was added to each tube. Samples were analyzed using LC/MS/MS to determine the concentrations of prodrug and parent drug.

LC-MS/MS analysis for MHF was performed using an API 4000 equipped with an Agilent 1100 HPLC and a Leap Technologies autosampler. A HPLC Phenomenex Onyx Monolithic C18 (CHO-7644) column at a temperature of 35° C., flow rate of 2.0 mL/min, injection volume of 30 µL, and a 3 min run time was used. Mobile phase AI was 0.1% formic acid in water and Mobile phase AII was 0.1% formic acid in acetonitrile. The gradient was 98% AI/2% AII at time 0; 98% AI/2% AII at time 0.1 mM; 5% AI/95% AII at time 1.4 mM; 5% AI/95% AII at time 2.2 min; 98% AI/2% AII at time 2.3 mM; and 98% AI/2% AII at time 3.0 min MHF content was determined using negative ion mode (Q1 128.94; Q2 71).

The stability of DMF and certain MHF prodrugs provided by the present disclosure in various media are presented Table 1.

TABLE 1

Stability of MHF prodrugs in biological media.
$T_{1/2}$ Parent Prodrug Cleavage (min)

| Cmpd | CaCo2 | rLiver | rPlasma | pPancreatin | rColonic Wash | pH 8.0[§] |
|------|-------|--------|---------|-------------|---------------|----------|
| DMF  | 2     | 1      | 2       | 0           | >60           | 0        |
| 10   | 3     | 1      | 1       | 4           | >60           | 42       |
| 4    | 5     | 2      | 1       | 2           | 33            | 40       |
| 2    | 4     | 9      | 9       | 1           | 25            | 17       |
| 9    | 8     | 6      | 1       | 4           | >60           | 47       |
| 1    | 8     | 2      | 1       | 8           | >60           | 63       |
| 5    | 30    | 10     | 2       | 3           | >60           | 53       |
| 3    | 56    | 22     | 1       | 8           | >60           | 53       |
| 8    | 52    | 23     | 6       | 15          | 27            | 141      |

[§]Percent DMF or prodrug remaining after 60 minutes.

Example 53

Methyl Hydrogen Fumarate Bioavailability Following Oral Administration of Methyl Hydrogen Fumarate Prodrugs Rats were obtained commercially and were pre-cannulated in the jugular vein. Animals were conscious at the time of the experiment. All animals were fasted overnight and until 4 hours post-dosing of a prodrug of Formula (I).

Rat blood samples (0.3 mL/sample) were collected from all animals prior to dosing and at different time-points up to 24 h post-dose into tubes containing EDTA. Two aliquots (100 µL each) were quenched with 300 µL methanol and stored at −20° C. prior to analysis.

To prepare analysis standards, 90 µL of rat blood was quenched with 300 µL methanol followed by 10 µL of spiking standard and/or 20 µL of internal standard. The sample tubes were vortexed for at least 2 min and then centrifuged at 3400 rpm for 20 min. The supernatant was then transferred to an injection vial or plate for analysis by LC-MS-MS.

To prepare samples for analysis, 20 µL of internal standard was added to each quenched sample tube. The sample tubes were vortexed for at least 2 min and then centrifuged at 3400 rpm for 20 mM The supernatant was then transferred to an injection vial or plate for analysis by LC-MS-MS.

LC-MS-MS analysis was performed using an API 4000 (MS12) equipped with Agilent 1100 HPLC and a Leap Technologies autosampler. The following HPLC column conditions were used: HPLC column: Onyx Monolithic C18 Phenomex (PN CHO-7644), 35 C; flow rate 2.0 mL/min; injection volume 30 µL; run time 3 min; mobile phase A: 0.1% formic acid in water; mobile phase B: 0.1% formic acid in acetonitrile (ACN); gradient: 98% A/2% B at 0.0 min; 98% A/2% B at 0.1 min; 5% A/95% B at 1.4 min; 5% A/95% B at 2.2 min; 98% λ/2% B at 2.3 min; and 98% A/2% B at 3.0 min MHF was monitored in negative ion mode.

Non-compartmental analysis was performed using WinNonlin software (v.3.1 Professional Version, Pharsight Corporation, Mountain View, Calif.) on individual animal profiles. Summary statistics on major parameter estimates was performed for $C_{max}$ (peak observed concentration following dosing), $T_{max}$ (time to maximum concentration is the time at which the peak concentration was observed), $AUC_{(0-t)}$ (area under the plasma concentration-time curve from time zero to last collection time, estimated using the log-linear trapezoidal method), $AUC_{(0-\infty)}$, (area under the plasma concentration time curve from time zero to infinity, estimated using the log-linear trapezoidal method to the last collection time with extrapolation to infinity), and $t_{1/2,z}$ (terminal half-life).

MHF, DMF or MHF prodrug was administered by oral gavage to groups of four to six adult male Sprague-Dawley rats (about 250 g) Animals were conscious at the time of the experiment. MHF, DMF or MHF prodrug was orally or colonically administered in 3.4% Phosal at a dose of 70 mg-equivalents MHF per kg body weight.

The percent relative bioavailability (F %) of MHF was determined by comparing the area under the MHF concentration vs time curve (AUC) following oral or colonic administration of DMF, MHF or MHF prodrug with the AUC of the MHF concentration vs time curve following intravenous administration of MHF on a dose normalized basis.

The MHF prodrugs (41), (3), (9), and (11), when administered perorally to rats at a dose of 30 mg/kg MHF-equivalents in 50 mM sodium acetate pH 4.6 exhibited an absolute oral bioavailability (relative to IV) ranging from about 43% to about 60% with an average bioavailability of about 51%.

Example 54

EAE Animal Model for Assessing Therapeutic Efficacy of MHF Prodrugs for Treating Multiple Sclerosis Animals and EAE Induction Female C57BL/6 mice, 8-10 weeks old (Harlan Laboratories, Livermore, Calif.), were immunized subcutaneously in the flanks and mid-scapular region with 200 µg of myelin oligodendrocyte glycoprotein peptide ($MOG_{35-55}$) (synthesized by Invitrogen) emulsified (1:1 volume ratio) with complete Freund's adjuvant (CFA) (containing 4 mg/mL *Mycobacterium tuberculosis*). Emulsion was prepared by the syringe-extrusion method with two glass Luer-Lock syringes connected by a 3-way stopcock. Mice were also given an intraperitoneal injection of 200 ng pertussis toxin (List Biological Laboratories, Inc, Campbell, Calif.) on the day of immunization and on day two post immunization. Mice were weighed and examined daily for clinical signs of experimental autoimmune encephalomyelitis (EAE). Food and water was provided ad libitum and once animals start to show disease, food was provided on the cage bottom. All experiments were approved by the Institutional Animal Care and Use Committee.

Clinical Evaluation

Mice were scored daily beginning on day 7 post immunization. The clinical scoring scale was as follows (Miller and Karplus, *Current Protocols in Immunology* 2007, 15.1.1-15.1.18): 0=normal; 1=limp tail or hind limb weakness (defined by foot slips between bars of cage top while walking); 2=limp tail and hind limb weakness; 3=partial hind limb paralysis (defined as no weight bearing on hind limbs but can still move one or both hind limbs to some extent); 4=complete hind limb paralysis; 5=moribund state (includes forelimb paralysis) or death.

Treatment

DMF or MHF prodrug are dissolved in 0.5% methocellulose/0.1% Tween80 in distilled water and administered by oral gavage twice daily starting from day 3 post-immunization until termination. Dexamethasone was dissolved in 1× PBS buffer and administered subcutaneously once daily. Treatment groups were as follows: vehicle alone, 15 mg/kg DMF, 20 mg/kg MHF prodrug, and 1 mg/kg dexamethasone.

Description 1

Use of an Animal Model to Assess Efficacy in Treating Psoriasis

The severe, combined immunodeficient (SCID) mouse model can be used to evaluate the efficacy of compounds for treating psoriasis in humans (Boehncke, *Ernst Schering Res Found Workshop* 2005, 50, 213-34; and Bhagavathula et al., *J Pharmacol Expt'l Therapeutics* 2008, 324(3), 938-947).

SCID mice are used as tissue recipients. One biopsy for each normal or psoriatic volunteer is transplanted onto the dorsal surface of a recipient mouse. Treatment is initiated 1 to 2 weeks after transplantation. Animals with the human skin transplants are divided into treatment groups Animals are treated twice daily for 14 days. At the end of treatment, animals are photographed and then euthanized. The transplanted human tissue along with the surrounding mouse skin is surgically removed and fixed in 10% formalin and samples obtained for microscopy. Epidermal thickness is measured. Tissue sections are stained with an antibody to the proliferation-associated antigen Ki-67 and with an anti-human CD3+ monoclonal antibody to detect human T lymphocytes in the transplanted tissue. Sections are also probed with antibodies to c-myc and β-catenin. A positive response to treatment is reflected by a reduction in the average epiderma thickness of the psoriatic skin transplants. A positive response is also associated with reduced expression of Ki-67 in keratinocytes.

Description 2

Animal Model for Assessing Therapeutic Efficacy of MHF Prodrugs for Treating Multiple Sclerosis Experiments are conducted on female mice aged 4-6 weeks belong to the C57BL/6 strain weighing 17-20 g. Experimental autoimmune encephalomyelitis (EAE) is actively induced using ≥95% pure synthetic myelin oligodendrocyte glycoprotein peptide 35-55 (MOG35-55, SEQ. ID NO. 1: MEVGWYRSPFSRVVHLYRNGK). Each mouse is anesthetized and receives 200 μg of MOG peptide and 15 μg of Saponin extract from Quilija bark emulsified in 100 μL of phosphate-buffered saline. A 25 μL volume is injected subcutaneously over four flank areas. Mice are also intraperitoneally injected with 200 ng of pertussis toxin in 200 μL of PBS. A second, identical injection of pertussis toxin is given after 48 h.

A MHF prodrug is administered at varying doses. Control animals receive 25 μL of DMSO. Daily treatment extends from day 26 to day 36 post-immunization. Clinical scores are obtained daily from day 0 post-immunization until day 60. Clinical signs are scored using the following protocol: 0, no detectable signs; 0.5, distal tail limpness, hunched appearance and quiet demeanor; 1, completely limp tail; 1.5, limp tail and hindlimb weakness (unsteady gait and poor grip with hindlimbs); 2, unilateral partial hindlimb paralysis; 2.5, bilateral hindlimb paralysis; 3, complete bilateral hindlimb paralysis; 3.5, complete hindlimb paralysis and unilateral forelimb paralysis; 4, total paralysis of hindlimbs and forelimbs (Eugster et al., *Eur J Immunol* 2001, 31, 2302-2312).

Inflammation and demyelination are assessed by histology on sections from the CNS of EAE mice. Mice are sacrificed after 30 or 60 days and whole spinal cords are removed and placed in 0.32 M sucrose solution at 4° C. overnight. Tissues are prepared and sectioned. Luxol fast blue stain is used to observe areas of demyelination. Haematoxylin and eosin staining is used to highlight areas of inflammation by darkly staining the nuclei of mononuclear cells Immune cells stained with H&E are counted in a blinded manner under a light microscope. Sections are separated into gray and white matter and each sector is counted manually before being combined to give a total for the section. T cells are immunolabeled with anti-CD3+ monoclonal antibody. After washing, sections are incubated with goat anti-rat HRP secondary antibody. Sections are then washed and counterstained with methyl green. Splenocytes isolated from mice at 30 and 60 days post-immunization are treated with lysis buffer to remove red blood cells. Cells are then resuspended in PBS and counted. Cells at a density of about $3 \times 10^6$ cells/mL are incubated overnight with 20 μg/mL of MOG peptide. Supernatants from stimulated cells are assayed for IFN-γ protein levels using an appropriate mouse IFN-γ immunoassay system.

Description 3

Use of an Animal Model to Assess Efficacy in Treating Inflammatory Bowel Disease Animal models of inflammatory bowel disease are described by Jurjus et al., *J Pharmaocol Toxicol Methods* 2004, 50, 81-92; Villegas et al., *Int'l Immunopharmacol* 2003, 3, 1731-1741; and Murakami et al., *Biochemical Pharmacol* 2003, 66, 1253-1261. For example, the following protocol can be used to assess the efficacy of a compound for treating inflammatory bowel disease.

Female ICR mice are used. Mice are divided into treatment groups. Groups are given either water (control), 5% DSS in tap water is given at the beginning of the experiment to induce colitis, or various concentrations of test compound. After administering test compound for 1 week, 5% DSS in tap water is also administered to the groups receiving test compound for 1 week. At the end of the experiment, all mice are killed and the large intestine is removed. Colonic mucosa samples are obtained and homogenized. Proinflammatory mediators (e.g., IL-1α, IL-1β, TNF-α, PGE2, and PGF2α) and protein concentrations are quantified. Each excised large intestine is histologically examined and the damage to the colon scored.

Description 4

Clinical Trial for Assessing Efficacy in Treating Asthma

Adult subjects (nonsmokers) with stable mild-to-moderate asthma are enrolled (see, e.g., Van Schoor and Pauwels, *Eur Respir J* 2002, 19, 997-1002). A randomized, double-blind, placebo-controlled, two-period crossover design is used. On screening day 1, patients undergo a methacholine challenge (<8 mg/mL). The baseline forced expiratory volume in one second (FEV1) prior to each subsequent challenge must be within 15% of the screening baseline FEV1 obtained at the first visit. A neurokinin challenge ($1 \times 10^{-6}$ mol/mL) on screening day 2 is performed 24-72 h later. Study-period one commences within 10 days after visit two. First, a methacholine and a neurokinin-A (NKA) challenge is performed on days 1 and 0, respectively. At visit four, test compound is administered at an appropriate dose and for an appropriate period of time. On the last 2 days of the treatment period, methacholine and NKA challenges are repeated. Following treatment-period one, there is a washout period of about 5 weeks, following which the patients crossed over to another medication or placebo in study period two, which is identical to period one. Pulmonary function tests are performed using a spirometer. The metacholine challenge is performed by inhaling doubling concentrations of methacholine until the FEV1 falls by >20% of the postdiluent baseline FEV1 of that day as described by Cockcroft et al., *Clin Allergy* 1977, 7, 235-243. NKA challenge is performed by inhaling increasing concentrations of NKA as described by Van Schoor et al., *Eur Respir J* 1998, 12, 17-23. The effect of a treatment on airway responsiveness is determined using appropriate statistical methods.

Description 5

Use of an Animal Model to Assess Efficacy in Treating Chronic Obstructive Pulmonary Disease An animal model using mice chronically exposed to cigarette smoke can be used for assessing efficacy in treating emphysema (see, e.g., Martorana et al., *Am J Respir Crit Care Med* 2005, 172, 848-835; and Cayarra et al., *Am J Respir Crit Care Med* 2001, 164, 886-890). Six-week old C57B1/6J male mice are used. In the acute study, the mice are exposed either to room air or to the smoke of five cigarettes for 20 minutes. In the chronic study, the mice are exposed to either room air or to the smoke of three cigarettes/day for 5 days/week for 7 months.

For the acute study, mice are divided into three groups of 40 animals each. These groups are then divided into four subgroups of 10 mice each as follows: (1) no treatment/air-exposed; (2) no treatment/smoke-exposed; (3) a first dose of test compound plus smoke-exposed; and (4) a second dose of test compound. In the first group, trolox equivalent antioxidant capacity is assessed at the end of the exposure in bronchoalveolar lavage fluid. In the second group, cytokines and chemokines are determined in bronchoalveolar lavage fluid using a commercial cytokine panel at 4 hours; and in the third group bronchoalveolar lavage fluid cell count is assessed at 24 hours.

For the chronic study, five groups of animals are used: (1) no treatment/air-exposed; (2) a first dose of a test compound plus air-exposed; (3) no treatment/smoke-exposed; (4) a second dose of the test compound plus smoke-exposed; and (5) the first dose of the test compound plus smoke exposed. Seven months after chronic exposure to room air or cigarette smoke, 5 to 12 animals from each group are killed an the lungs fixed intratracheally with formalin. Lung volume is measured by water displacement. Lungs are stained. Assessment of emphysema includes mean linear intercept and internal surface area. The volume density of macrophages, marked immunohistochemically with antimouse Mac-3 monoclonal antibodies is determined by point counting. A mouse is considered to have goblet cell metaplasia when at least one or more midsize bronchi/lung showed a positive periodic acid-Schiff staining. For the determination of desmosine, fresh lungs are homogenized, processed, and analyzed by high-pressure liquid chromatography.

Description 6

Animal Models for Assessing Therapeutic Efficacy of MHF Prodrugs for Treating Parkinson's Disease MPTP Induced Neurotoxicity MPTP, or 1-methyl-4-phenyl-1,2,3,6-tetrahydropyridine is a neurotoxin that produces a Parkinsonian syndrome in both man and experimental animals. Studies of the mechanism of MPTP neurotoxicity show that it involves the generation of a major metabolite, $MPP^+$, formed by the activity of monoamine oxidase on MPTP Inhibitors of monoamine oxidase block the neurotoxicity of MPTP in both mice and primates. The specificity of the neurotoxic effects of $MPP^+$ for dopaminergic neurons appears to be due to the uptake of $MPP^+$ by the synaptic dopamine transporter. Blockers of this transporter prevent $MPP^+$ neurotoxicity. $MPP^+$ has been shown to be a relatively specific inhibitor of mitochondrial complex I activity, binding to complex I at the retenone binding site and impairing oxidative phosphorylation. In vivo studies have shown that MPTP can deplete striatal ATP concentrations in mice. It has been demonstrated that $MPP^+$ administered intrastriatally to rats produces significant depletion of ATP as well as increased lactate concentration confined to the striatum at the site of the injections. Compounds that enhance ATP production can protect against MPTP toxicity in mice.

A prodrug of Formulae (I)-(IV) is administered to animals such as mice or rats for three weeks before treatment with MPTP. MPTP is administered at an appropriate dose, dosing interval, and mode of administration for 1 week before sacrifice. Control groups receive either normal saline or MPTP hydrochloride alone. Following sacrifice the two striate are rapidly dissected and placed in chilled 0.1 M perchloric acid. Tissue is subsequently sonicated and aliquots analyzed for protein content using a fluorometer assay. Dopamine, 3,4-dihydroxyphenylacetic acid (DOPAC), and homovanillic acid (HVA) are also quantified. Concentrations of dopamine and metabolites are expressed as nmol/mg protein.

Prodrugs of Formulae (I)-(IV) that protect against DOPAC depletion induced by MPTP, HVA, and/or dopamine depletion are neuroprotective and therefore can be useful for the treatment of Parkinson's disease.

Haloperidol-Induced Hypolocomotion

The ability of a compound to reverse the behavioral depressant effects of dopamine antagonists such as haloperidol, in rodents and is considered a valid method for screening drugs with potential antiparkinsonian effects (Mandhane, et al.,

*Eur. J. Pharmacol* 1997, 328, 135-141). Hence, the ability of prodrugs of Formulae (I)-(IV) to block haloperidol-induced deficits in locomotor activity in mice can be used to assess both in vivo and potential anti-Parkinsonian efficacy.

Mice used in the experiments are housed in a controlled environment and allowed to acclimatize before experimental use. One and one-half (1.5) hours before testing, mice are administered 0.2 mg/kg haloperidol, a dose that reduces baseline locomotor activity by at least 50%. A test compound is administered 5-60 min prior to testing. The animals are then placed individually into clean, clear polycarbonate cages with a flat perforated lid. Horizontal locomotor activity is determined by placing the cages within a frame containing a 3×6 array of photocells interfaced to a computer to tabulate beam interrupts. Mice are left undisturbed to explore for 1 h, and the number of beam interruptions made during this period serves as an indicator of locomotor activity, which is compared with data for control animals for statistically significant differences.

6-Hydroxydopamine Animal Model

The neurochemical deficits seen in Parkinson's disease can be reproduced by local injection of the dopaminergic neurotoxin, 6-hydroxydopamine (6-OHDA) into brain regions containing either the cell bodies or axonal fibers of the nigrostriatal neurons. By unilaterally lesioning the nigrostriatal pathway on only one-side of the brain, a behavioral asymmetry in movement inhibition is observed. Although unilaterally-lesioned animals are still mobile and capable of self maintenance, the remaining dopamine-sensitive neurons on the lesioned side become supersensitive to stimulation. This is demonstrated by the observation that following systemic administration of dopamine agonists, such as apomorphine, animals show a pronounced rotation in a direction contralateral to the side of lesioning. The ability of compounds to induce contralateral rotations in 6-OHDA lesioned rats has been shown to be a sensitive model to predict drug efficacy in the treatment of Parkinson's disease.

Male Sprague-Dawley rats are housed in a controlled environment and allowed to acclimatize before experimental use. Fifteen minutes prior to surgery, animals are given an intraperitoneal injection of the noradrenergic uptake inhibitor desipramine (25 mg/kg) to prevent damage to nondopamine neurons Animals are then placed in an anesthetic chamber and anesthetized using a mixture of oxygen and isoflurane. Once unconscious, the animals are transferred to a stereotaxic frame, where anesthesia is maintained through a mask. The top of the head is shaved and sterilized using an iodine solution. Once dry, a 2 cm long incision is made along the midline of the scalp and the skin retracted and clipped back to expose the skull. A small hole is then drilled through the skull above the injection site. In order to lesion the nigrostriatal pathway, the injection cannula is slowly lowered to position above the right medial forebrain bundle at −3.2 mm anterior posterior, −1.5 mm medial lateral from the bregma, and to a depth of 7.2 mm below the duramater. Two minutes after lowering the cannula, 6-OHDA is infused at a rate of 0.5 µL/min over 4 min, to provide a final dose of 8 µg. The cannula is left in place for an additional 5 min to facilitate diffusion before being slowly withdrawn. The skin is then sutured shut, the animal removed from the sterereotaxic frame, and returned to its housing. The rats are allowed to recover from surgery for two weeks before behavioral testing.

Rotational behavior is measured using a rotameter system having stainless steel bowls (45 cm dia×15 cm high) enclosed in a transparent Plexiglas cover around the edge of the bowl and extending to a height of 29 cm. To assess rotation, rats are placed in a cloth jacket attached to a spring tether connected to an optical rotameter positioned above the bowl, which assesses movement to the left or right either as partial (45°) or full (360°) rotations.

To reduce stress during administration of a test compound, rats are initially habituated to the apparatus for 15 min on four consecutive days. On the test day, rats are given a test compound, e.g., a prodrug of Formulae (I)-(IV). Immediately prior to testing, animals are given a subcutaneous injection of a subthreshold dose of apomorphine, and then placed in the harness and the number of rotations recorded for one hour. The total number of full contralatral rotations during the hour test period serves as an index of antiparkinsonian drug efficacy.

Description 7

Animal Model for Assessing Therapeutic Efficacy of MHF Prodrugs for Treating Alzheimer's Disease Heterozygous transgenic mice expressing the Swedish AD mutant gene, hAPPK670N, M671L (Tg2576; Hsiao, *Learning & Memory* 2001, 8, 301-308) are used as an animal model of Alzheimer's disease Animals are housed under standard conditions with a 12:12 light/dark cycle and food and water available ad libitum. Beginning at 9 months of age, mice are divided into two groups. The first two groups of animals receive increasing doses of a MHF prodrug, over six weeks. The remaining control group receives daily saline injections for six weeks.

Behavioral testing is performed at each drug dose using the same sequence over two weeks in all experimental groups: (1) spatial reversal learning, (2) locomotion, (3) fear conditioning, and (4) shock sensitivity.

Acquisition of the spatial learning paradigm and reversal learning are tested during the first five days of test compound administration using a water T-maze as described in Bardgett et al., *Brain Res Bull* 2003, 60, 131-142. Mice are habituated to the water T-maze during days 1-3, and task acquisition begins on day 4. On day 4, mice are trained to find the escape platform in one choice arm of the maze until 6 to 8 correct choices are made on consecutive trails. The reversal learning phase is then conducted on day 5. During the reversal learning phase, mice are trained to find the escape platform in the choice arm opposite from the location of the escape platform on day 4. The same performance criteria and inter-trial interval are used as during task acquisition.

Large ambulatory movements are assessed to determine that the results of the spatial reversal learning paradigm are not influenced by the capacity for ambulation. After a rest period of two days, horizontal ambulatory movements, excluding vertical and fine motor movements, are assessed in a chamber equipped with a grid of motion-sensitive detectors on day 8. The number of movements accompanied by simultaneous blocking and unblocking of a detector in the horizontal dimension are measured during a one-hour period.

The capacity of an animal for contextual and cued memory is tested using a fear conditioning paradigm beginning on day 9. Testing takes place in a chamber that contains a piece of absorbent cotton soaked in an odor-emitting solution such as mint extract placed below the grid floor. A 5-min, 3 trial 80 db, 2800 Hz tone-foot shock sequence is administered to train the animals on day 9. On day 10, memory for context is tested by returning each mouse to the chamber without exposure to the tone and foot shock, and recording the presence or absence of freezing behavior every 10 seconds for 8 minutes. Freezing is defined as no movement, such as ambulation, sniffing or stereotypy, other than respiration.

On day 11, the response of the animal to an alternate context and to the auditory cue is tested. Coconut extract is placed in a cup and the 80 dB tone is presented, but no foot shock is delivered. The presence or absence of freezing in response to the alternate context is then determined during the first 2 minutes of the trial. The tone is then presented continuously for the remaining 8 minutes of the trial, and the presence or absence of freezing in response to the tone is determined.

On day 12, the animals are tested to assess their sensitivity to the conditioning stimulus, i.e., foot shock.

Following the last day of behavioral testing, animals are anesthetized and the brains removed, post-fixed overnight, and sections cut through the hippocampus. The sections are stained to image β-amyloid plaques.

Data is analyzed using appropriate statistical methods.

Description 8

Animal Model for Assessing Therapeutic Efficacy of MHF Prodrugs for Treating Huntington's Disease Neuroprotective Effects in a Transgenic Mouse Model of Huntington's Disease Transgenic HD mice of the N171-82Q strain and non-transgenic littermates are treated with a prodrug of Formulae (I)-(IV) or a vehicle from 10 weeks of age. The mice are placed on a rotating rod ("rotarod"). The length of time at which a mouse falls from the rotarod is recorded as a measure of motor coordination. The total distance traveled by a mouse is also recorded as a measure of overall locomotion. Mice administered prodrugs of Formulae (I)-(IV) that are neuroprotective in the N171-82Q transgenic HD mouse model remain on the rotarod for a longer period of time and travel farther than mice administered vehicle.

Malonate Model of Huntington's Disease

A series of reversible and irreversible inhibitors of enzymes involved in energy generating pathways has been used to generate animal models for neurodegenerative diseases such as Parkinson's and Huntington's diseases. In particular, inhibitors of succinate dehydrogenase, an enzyme that impacts cellular energy homeostasis, has been used to generate a model for Huntington's disease.

To evaluate the effect of MHF prodrugs of Formulae (I)-(IV) in this malonate model for Huntington's disease, a prodrug of Formulae (I)-(IV) is administered at an appropriate dose, dosing interval, and route, to male Sprague-Dawley rats. A prodrug is administered for two weeks prior to the administration of malonate and then for an additional week prior to sacrifice. Malonate is dissolved in distilled deionized water and the pH adjusted to 7.4 with 0.1 M HCl. Intrastriatal injections of 1.5 µL of 3 µmol malonate are made into the left striatum at the level of the Bregma 2.4 mm lateral to the midline and 4.5 mm ventral to the dura Animals are sacrificed at 7 days by decapitation and the brains quickly removed and placed in ice cold 0.9% saline solution. Brains are sectioned at 2 mm intervals in a brain mold. Slices are then placed posterior side down in 2% 2,3,5-tiphenyltetrazolium chloride. Slices are stained in the dark at room temperature for 30 min and then removed and placed in 4% paraformaldehyde pH 7.3. Lesions, noted by pale staining, are evaluated on the posterior surface of each section. The measurements are validated by comparison with measurements obtained on adjacent Niss1 stain sections. Compounds exhibiting a neuroprotective effect and therefore potentially useful in treating Huntington's disease show a reduction in malonate-induced lesions.

Description 9

Animal Model for Assessing Therapeutic Efficacy of MHF Prodrugs for Treating Amyotrophic Lateral Sclerosis A murine model of SOD1 mutation-associated ALS has been developed in which mice express the human superoxide dismutase (SOD) mutation glycine→alanine at residue 93 (SOD1). These SOD1 mice exhibit a dominant gain of the adverse property of SOD, and develop motor neuron degeneration and dysfunction similar to that of human ALS. The SOD1 transgenic mice show signs of posterior limb weakness at about 3 months of age and die at 4 months. Features common to human ALS include astrocytosis, microgliosis, oxidative stress, increased levels of cyclooxygenase/prostaglandin, and, as the disease progresses, profound motor neuron loss.

Studies are performed on transgenic mice overexpressing human Cu/Zn-SOD G93A mutations (B6SJL-TgN(SOD1-G93A) 1 Gur) and non-transgenic B6/SJL mice and their wild litter mates. Mice are housed on a 12-hr day/light cycle and (beginning at 45 d of age) allowed ad libitum access to either test compound-supplemented chow, or, as a control, regular formula cold press chow processed into identical pellets. Genotyping can be conducted at 21 days of age as described in Gurney et al., *Science* 1994, 264(5166), 1772-1775. The SOD1 mice are separated into groups and treated with a test compound, e.g., an MHF prodrug, or serve as controls.

The mice are observed daily and weighed weekly. To assess health status mice are weighed weekly and examined for changes in lacrimation/salivation, palpebral closure, ear twitch and pupillary responses, whisker orienting, postural and righting reflexes and overall body condition score. A general pathological examination is conducted at the time of sacrifice.

Motor coordination performance of the animals can be assessed by one or more methods known to those skilled in the art. For example, motor coordination can be assessed using a neurological scoring method. In neurological scoring, the neurological score of each limb is monitored and recorded according to a defined 4-point scale: 0—normal reflex on the hind limbs (animal will splay its hind limbs when lifted by its tail); 1—abnormal reflex of hind limbs (lack of splaying of hind limbs weight animal is lifted by the tail); 2—abnormal reflex of limbs and evidence of paralysis; 3—lack of reflex and complete paralysis; and 4—inability to right when placed on the side in 30 seconds or found dead. The primary end point is survival with secondary end points of neurological score and body weight. Neurological score observations and body weight are made and recorded five days per week. Data analysis is performed using appropriate statistical methods.

The rotarod test evaluates the ability of an animal to stay on a rotating dowel allowing evaluation of motor coordination and proprioceptive sensitivity. The apparatus is a 3 cm diameter automated rod turning at, for example, 12 rounds per min. The rotarod test measures how long the mouse can maintain itself on the rod without falling. The test can be stopped after an arbitrary limit of 120 sec. Should the animal fall down before 120 sec, the performance is recorded and two additional trials are performed. The mean time of 3 trials is calculated. A motor deficit is indicated by a decrease of walking time.

In the grid test, mice are placed on a grid (length: 37 cm, width: 10.5 cm, mesh size: 1×1 cm$^2$) situated above a plane support. The number of times the mice put their paws through the grid is counted and serves as a measure for motor coordination.

The hanging test evaluates the ability of an animal to hang on a wire. The apparatus is a wire stretched horizontally 40 cm above a table. The animal is attached to the wire by its forepaws. The time needed by the animal to catch the string with its hind paws is recorded (60 sec max) during three consecutive trials.

Electrophysiological measurements (EMG) can also be used to assess motor activity condition. Electromyographic recordings are performed using an electromyography apparatus. During EMG monitoring mice are anesthetized. The measured parameters are the amplitude and the latency of the compound muscle action potential (CMAP). CMAP is measured in gastrocnemius muscle after stimulation of the sciatic nerve. A reference electrode is inserted near the Achilles tendon and an active needle placed at the base of the tail. A ground needle is inserted on the lower back of the mice. The sciatic nerve is stimulated with a single 0.2 msec pulse at supramaximal intensity (12.9 mA). The amplitude (mV) and the latency of the response (ms) are measured. The amplitude is indicative of the number of active motor units, while distal latency reflects motor nerve conduction velocity.

The efficacy of test compounds can also be evaluated using biomarker analysis. To assess the regulation of protein biomarkers in SOD1 mice during the onset of motor impairment, samples of lumbar spinal cord (protein extracts) are applied to ProteinChip Arrays with varying surface chemical/biochemical properties and analyzed, for example, by surface enhanced laser desorption ionization time of flight mass spectrometry. Then, using integrated protein mass profile analysis methods, data is used to compare protein expression profiles of the various treatment groups. Analysis can be performed using appropriate statistical methods.

Finally, it should be noted that there are alternative ways of implementing the embodiments disclosed herein. Accordingly, the present embodiments are to be considered as illustrative and not restrictive, and the claims are not to be limited to the details given herein, but may be modified within the scope and equivalents thereof.

What is claimed is:

1. A method of treating a patient suffering from a disease selected from psoriasis, multiple sclerosis, Huntington's disease, asthma, Parkinson's disease, amyotrophic lateral sclerosis, Alzheimer's disease, rheumatoid arthritis, Crohn's disease, ankylosing spondylitis, ulcerative colitis and psoriatic arthritis, comprising administering to a patient in need thereof a compound of Formula (I) or a pharmaceutically acceptable salt thereof:

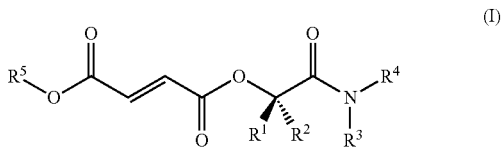

wherein:
R$^1$ and R$^2$ are independently chosen from hydrogen, C$_{1-6}$ alkyl, and substituted C$_{1-6}$ alkyl;
R$^3$ and R$^4$ are independently chosen from hydrogen, C$_{1-6}$ alkyl, substituted C$_{1-6}$ alkyl, C$_{1-6}$ heteroalkyl, substituted C$_{1-6}$ heteroalkyl, C$_{4-12}$ cycloalkylalkyl, substituted C$_{4-12}$ cycloalkylalkyl, C$_{7-12}$ arylalkyl, and substituted C$_{7-12}$ arylalkyl; or R$^3$ and R$^4$ together with the nitrogen to which they are bonded form a ring chosen from a C$_{5-10}$ heteroaryl, substituted C$_{5-10}$ heteroaryl, C$_{5-10}$ heterocycloalkyl, and substituted C$_{5-10}$ heterocycloalkyl; and
R$^5$ is methyl;
wherein each substituent group is independently chosen from halogen, —OH, —CN, —CF$_3$, =O, —NO$_2$, benzyl, —C(O)NR$^{11}$$_2$, —R$^{11}$, —OR$^{11}$, —C(O)R$^{11}$, —COOR$^{11}$, and —NR$^{11}$$_2$ wherein each R$^{11}$ is independently chosen from hydrogen and C$_{1-4}$ alkyl.

2. The method of claim 1 wherein the disease is selected from psoriasis and multiple sclerosis.

3. The method of claim 1 wherein the disease is psoriasis.

4. The method of claim 1 comprising administering a second therapeutic agent effective in treating psoriasis.

5. The method of claim 1 wherein the disease is multiple sclerosis.

6. The method of claim 1 comprising administering a second therapeutic agent effective in treating multiple sclerosis.

7. The method of claim 1 wherein the disease is selected from Huntington's disease, asthma, Parkinson's disease, amyotrophic lateral sclerosis, and Alzheimer's disease.

8. The method of claim 1 wherein the disease is selected from rheumatoid arthritis and Crohn's disease.

9. The method of claim 1 wherein the disease is selected from ankylosing spondylitis and ulcerative colitis.

10. The method of claim 1, wherein each of R$^1$ and R$^2$ is hydrogen.

11. The method of claim 1, wherein one of $R^1$ and $R^2$ is hydrogen and the other of $R^1$ and $R^2$ is chosen from methyl, ethyl, n-propyl, isopropyl, n-butyl, isobutyl, and sec-butyl.

12. The method of claim 1, wherein $R^3$ and $R^4$ are independently chosen from hydrogen and $C_{1-6}$ alkyl.

13. The method of claim 1, wherein $R^3$ and $R^4$ together with the nitrogen to which they are bonded form a $C_{5-10}$ heterocycloalkyl ring.

14. The method of claim 1, wherein one of $R^1$ and $R^2$ is hydrogen and the other of $R^1$ and $R^2$ is chosen from hydrogen and $C_{1-6}$ alkyl; and $R^3$ and $R^4$ together with the nitrogen to which they are bonded form a ring chosen from morpholine, piperazine, and N-substituted piperazine.

15. The method of claim 1, wherein one of $R^1$ and $R^2$ is hydrogen; and the other of $R^1$ and $R^2$ is chosen from hydrogen and $C_{1-6}$ alkyl; $R^3$ is hydrogen; and $R^4$ is chosen from hydrogen, $C_{1-6}$ alkyl, and benzyl.

16. The method of claim 1, wherein the compound is chosen from:

- (N,N-diethylcarbamoyl)methyl methyl (2E)but-2-ene-1,4-dioate;
- methyl [N-benzylcarbamoyl]methyl (2E)but-2-ene-1,4-dioate;
- methyl 2-morpholin-4-yl-2-oxoethyl (2E)but-2-ene-1,4-dioate;
- (N-butylcarbamoyl)methyl methyl (2E)but-2-ene-1,4-dioate;
- [N-(2-methoxyethyl)carbamoyl]methyl methyl (2E)but-2-ene-1,4-dioate;
- 2-{2-[(2E)-3-(methoxycarbonyl)prop-2-enoyloxy]acetylamino}acetic acid;
- 4-{2-[(2E)-3-(methoxycarbonyl)prop-2-enoyloxy]acetylamino}butanoic acid;
- (N,N-dimethylcarbamoyl)methyl methyl (2E)but-2-ene-1,4-dioate;
- bis-(2-methoxyethylamino)carbamoyl]methyl methyl (2E)but-2-ene-1,4-dioate;
- [N-(methoxycarbonyl)carbamoyl]methyl methyl (2E)but-2ene-1,4-dioate;
- methyl 2-oxo-2-piperazinylethyl (2E)but-2-ene-1,4-dioate;
- methyl 2-oxo-2-(2-oxo(1,3-oxazolidin-3-yl)ethyl (2E)but-2ene-1,4-dioate;
- {N-[2-(dimethylamino)ethyl]carbamoyl}methyl methyl (2E)but-2ene-1,4 dioate;
- methyl 2-(4-methylpiperazinyl)-2-oxoethyl (2E)but-2-ene-1,4-dioate;
- methyl {N-[(propylamino)carbonyl]carbamoyl}methyl (2E)but-2ene-1,4-dioate;
- 2-(4-acetylpiperazinyl)-2-oxoethyl methyl (2E)but-2ene-1,4-dioate;
- {N,N-bis[2-(methylethoxy)ethyl]carbamoyl}methyl methyl (2E)but-2-ene-1,4-dioate;
- methyl 2-(4-benzylpiperazinyl)-2-oxoethyl (2E)but-2-ene-1,4-dioate;
- [N,N-bis(2-ethoxyethyl)carbamoyl]methyl methyl (2E)but-2-ene-1,4-dioate;
- 2-{(2S)-2-[tert-butyl)oxycarbonyl]pyrrolidinyl}-2-oxoethyl methyl (2E)but-2ene-1,4-dioate;
- 1-{2-{(2E)-3-(methoxycarbonyl)prop-2-enoyloxy]acetyl}(2S)pyrrolidine-2-carboxylic acid;
- (N-{[tert-butyl)oxycarbonyl]methyl}-N-methylcarbamoyl)methyl methyl (2E)but-2-ene-1,4-dioate;
- {N-(ethoxycarbonyl)methyl]-N-methylcarbamoyl}methyl methyl (2E)but-2-ene-1,4-dioate;
- methyl 1-methyl-2-morpholin-4-yl-2-oxoethyl(2E)but-2-ene-1,4-dioate;
- [N,N-bis(2-methoxyethyl)carbamoyl]ethyl methyl (2E)but-2-ene-1,4-dioate;
- (N,N-dimethylcarbamoyl)ethyl methyl (2E)but-2-ene-1,4-dioate;
- 2-{2-[(2E)-3-(methoxy carbonyl)prop-2-enoyloxyl]-N-methylacetylamino}acetic acid;
- (N-{[(tert-butyl)oxycarbonyl]methyl}carbamoyl)methyl methyl (2E)but-2-ene-1,4-dioate;
- methyl (N-methyl-N-{[(methylethyl)oxycarbonyl]methyl}carbamoyl)methyl (2E)but-2-ene-1,4-dioate;
- {N-[(ethoxycarbonyl)methyl]-N-benzylcarbamoyl}methyl methyl (2E)but-2-ene-1,4-dioate;
- {N-[(ethoxycarbonyl)methyl]-N-benzylcarbamoyl}ethyl methyl (2E)but-2-ene-1,4-dioate;
- {N-[(ethoxycarbonyl)methyl]-N-methylcarbamoyl}ethyl methyl (2E)but-2-ene-1,4-dioate;
- (1S)-1-methyl-2-morpholin-4-yl-2-oxoethyl methyl (2E)but-2-ene-1,4-dioate;
- (1S)-1-[N,N-bis(2-methoxyethyl)carbamoyl]ethyl methyl (2E)but-2-ene-1,4-dioate;
- (1R)-1-(N,N-diethylcarbamoyl)ethyl methyl (2E)but-2-ene-1,4-dioate;
- (N-[(methoxycarbonyl)ethyl]carbamoyl)methyl methyl (2E)but-2-ene-1,4-dioate;
- 2-{2-[(2E)-3-(methoxycarbonyl)prop-2-enoyloxy]acetylamino}propanoic acid; and pharmaceutically acceptable salts of any of the foregoing.

17. The method of claim 1, wherein $R^3$ and $R^4$ are independently chosen from methyl, ethyl, methoxyethyl; or $R^3$ and $R^4$ together with the nitrogen to which they are bonded form a 4-morpholinyl group.

18. The method of claim 1, wherein the compound is (N,N-diethylcarbamoyl)methyl methyl (2E)but-2-ene-1,4-dioate.

19. The method of claim 18, wherein the disease is psoriasis.

20. The method of claim 18, wherein the disease is multiple sclerosis.

21. The method of claim 18, wherein the compound is in an oral formulation.

22. The method of claim 21, wherein the oral formulation is an oral sustained release formulation.

23. The method of claim 1, wherein the compound is methyl 2-morpholin-4-yl-2-oxoethyl (2E)but-2-ene-1,4-dioate.

24. The method of claim 23, wherein the disease is psoriasis.

25. The method of claim 23, wherein the disease is multiple sclerosis.

26. The method of claim 23, wherein the compound is in an oral formulation.

27. The method of claim 23, wherein the oral formulation is an oral sustained release formulation.

28. The method of claim 1, wherein the compound is bis-(2-methoxyethylamino)carbamoyl]methyl methyl (2E)but-2-ene-1,4-dioate.

29. The method of claim 28, wherein the disease is psoriasis.

30. The method of claim 28, wherein the disease is multiple sclerosis.

31. The method of claim 28, wherein the compound is in an oral formulation.

32. The method of claim 31, wherein the oral formulation is an oral sustained release formulation.

33. The method of claim 1, wherein the compound is (N,N-dimethylcarbamoyl)methyl methyl (2E)but-2-ene-1,4-dioate.

34. The method of claim 33, wherein the disease is psoriasis.

35. The method of claim 33, wherein the disease is multiple sclerosis.

36. The method of claim 33, wherein the compound is in an oral formulation.

37. The method of claim 36, wherein the oral formulation is an oral sustained release formulation.

38. The method of claim 1 wherein the compound is in an oral formulation.

39. The method of claim 38 wherein the oral formulation is an oral sustained release formulation.

40. The method of claim 1 comprising administering a second therapeutic agent effective in minimizing an adverse effect associated with the compound of Formula (I).

41. The method of claim 1 comprising administering a second therapeutic agent selected from a non-steroidal anti-inflammatory agent and a cox-2 inhibitor.

42. The method of claim 1 comprising administering a second therapeutic agent selected from vitamin E, paroxetine, gabapentin and pentoxifylline.

* * * * *

UNITED STATES PATENT AND TRADEMARK OFFICE
CERTIFICATE OF CORRECTION

PATENT NO. : 8,785,443 B2  Page 1 of 1
APPLICATION NO. : 13/274284
DATED : July 22, 2014
INVENTOR(S) : Gangakhedkar et al.

It is certified that error appears in the above-identified patent and that said Letters Patent is hereby corrected as shown below:

In the Claims

| Column | Line | PTO | Should Be |
|---|---|---|---|
| 83 | 43 | "methyl 2-oxo-2-(2-oxo(1,3-oxazolidin-3-yl)ethyl (2E)" | -- methyl 2-oxo-2-(2-oxo(1,3-oxazolidin-3yl)ethyl (2E) -- |
| 83 | 59 | "2-{(2S)-2-[tert-butyl)oxycarbonyl]pyrrolidinyl}-2-oxoet" | -- 2{(2S)-2-[(tert-butyl)oxycarbonyl]pyrrolidinyl}-2-oxoet -- |

Signed and Sealed this
Fourteenth Day of October, 2014

Michelle K. Lee
*Deputy Director of the United States Patent and Trademark Office*

SEQUENCE LISTING

<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: synthetic myelin oligodendrocyte glycoprotein
      peptide 35-55

<400> SEQUENCE: 1

Met Glu Val Gly Trp Tyr Arg Ser Pro Phe Ser Arg Val Val His Leu
1               5                   10                  15

Tyr Arg Asn Gly Lys
            20